United States Patent [19]

Brooks et al.

[11] Patent Number: 5,086,052

[45] Date of Patent: Feb. 4, 1992

[54] SUBSTITUTED 1,4,5,6-TETRAHYDRO-2H-PYRIDAZIN-3-ONE AND-3-THIONE COMPOUNDS HAVING LIPOXYGENASE INHIBITORY ACTIVITY

[75] Inventors: Dee W. Brooks, Libertyville; George W. Carter, Mundelein; Anwer Basha, Lake Forest; Bruce P. Gunn, Island Lake, all of Ill.; Richard D. Dyer, Ann Arbor, Mich.

[73] Assignee: Abbott Laboratories, Abbott Park, Ill.

[21] Appl. No.: 546,337

[22] Filed: Jun. 28, 1990

Related U.S. Application Data

[60] Division of Ser. No. 210,806, Jun. 28, 1988, Pat. No. 4,970,210, which is a continuation-in-part of Ser. No. 75,015, Jul. 17, 1987, abandoned.

[51] Int. Cl.$^5$ ............... A61K 31/535; A61K 31/50; C07D 237/02; C07D 265/30
[52] U.S. Cl. .................. 514/231.5; 514/225.8; 514/229.2; 514/247; 514/252; 544/37; 544/66; 544/68; 544/238; 544/239; 544/240; 544/241
[58] Field of Search ............ 514/225.8, 229.2, 247, 514/252, 259, 231.5; 544/37, 66, 68, 238, 239, 240, 241

[56] References Cited

PUBLICATIONS

Baloniak, S., Rocz. Chem., 42(11):1867–1872 (1968) as abstracted in Chemical Abstracts, 70:10645g(1969).
Baloniak, S., Rocz. Chem., 43(2): 315–318(1969) as abstracted in Chemical Abstracts, 70:115096y(1969).
Baloniak, S. Rocz. Chem., 48(3): 399–408(1974) as abstracted in Chemical Abstracts, 81:120559h(1974).
Baloniak, S. et al., Pol. J. Chem., 52(6): 1249–1253(1978) as abstracted in Chemical Abstracts, 89:215325h(1978).
Baloniak, S. et al., Acta Pol. Pharm. 36(2): 147–154(1979) as abstracted in Chemical Abstracts, 93:114428w(1980).
Baloniak, S. et al., Acta Pol. Pharm., 36(3): 295–300(1979) as abstracted in Chemical Abstracts, 93:168212q(1980).
Hladon, B. et al., Pol. J. Pharmacol. Pharm., 33(4): 445–452(1981) as abstracted in Chemical Abstracts, 96:115522w(1982).
Zyczynska-Baloniak, I. et al., Acta Pol. Pharm., 38(5):551–554(1981) as abstracted in Chemical Abstracts, 97:72315g(1982).
Baloniak, S. et al., Acta Pol. Pharm., 39(4):193–197 (1982) as abstracted in Chemical Abstracts, 98:197866q(1983).
Baloniak, S. Acta Pol. Pharm., 39(1–3):65–69(1982) as abstracted in Chemical Abstracts, 98:215554t(1983).
Jungstand, W. et al., Pol. J. Pharmacol. Pharm., 34(4):207–216(1983) as abstracted in Chemical Abstracts, 99:159c(1983).
Baloniak, S. et al., acta Pol. Pharm., 39(1–3):71–78(1982) as abstracted in Chemical Abstracts, 99:53681y(1983).
Baloniak, S. et al., Acta Pol. Pharm., 39(5–6):297–304(1982) as abstracted in Chemical Abstracts, 99:175692y(1983).
Baloniak et al., "Chemical Abstract", vol. 98, 1983 #215554t.
Baloniak et al., "Chemical Abstract", vol. 99, 1983, #53681y.
Baloniak et al., "Chemical Abstract", vol. 99, 1983, #175692y.

Primary Examiner—Nicholas S. Rizzo
Assistant Examiner—Yogendra N. Gupta
Attorney, Agent, or Firm—Jerry F. Janssen

[57] ABSTRACT

Pyridazinone, triazinone and oxapyridazinone compounds which are useful in inhibiting lipoxygenase enzymes, particularly 5-lipoxygenase.

5 Claims, No Drawings

SUBSTITUTED 1,4,5,6-TETRAHYDRO-2H-PYRIDAZIN-3-ONE AND-3-THIONE COMPOUNDS HAVING LIPOXYGENASE INHIBITORY ACTIVITY

CROSS-REFERENCE TO RELATED APPLICATIONS

This application is a divisional of copending application Ser. No. 210,806 filed June 28, 1988, now U.S. Pat. No. 4,970,210, issued Nov. 13, 1990 which is a continuation-in-part of application Ser. No. 075,015 filed July 17, 1987, now abandoned.

BACKGROUND OF THE INVENTION

This invention relates to compounds, compositions and methods for inhibiting lipoxygenase enzymes.

The lipoxygenases are a family of enzymes which catalyze the oxygenation of arachidonic acid. The enzyme 5-lipoxygenase converts arachidonic acid to 5-hydroperoxyeicosatetraenoic acid (5-HPETE). This is the first step in the metabolic pathway yielding 5-hydroxyeicosatetraenoic acid (5-HETE) and the important class of potent biological mediators, the leukotrienes (LTs).

A variety of biological effects are believed to be associated with these products from lipoxygenase metabolism of arachidonic acid, and they have been implicated as mediators in various disease states. For example, the LTs $C_4$ and $D_4$ are potent constrictors of human airways in vitro, and aerosol administration of these substances to non-asthmatic volunteers induces broncho-constriction. $LTB_4$ and 5-HETE are potent chemotactic factors for inflammatory cells such as polymorphonuclear leukocytes. They also have been found in the synovial fluid of rheumatoid arthritic patients. Leukotrienes have also been implicated as important mediators in allergic rhinitis, psoriasis, adult respiratory distress syndrome, Crohn's disease, endotoxin shock, and ischemia induced myocardial injury among others. The biological activity of the LTs has been reviewed by Lewis and Austen (*J. Clinical Invest.* 73,89, 1984 and by J. Sirois (*Adv. Lipid Res.* 21, 78, 1985).

Thus, lipoxygenase enzymes are believed to play an important role in the biosynthesis of mediators of asthma, allergy arthritis, psoriasis, and inflammation. Blocking the activity of these enzymes will likely interrupt the pathological pathways believed to be involved in these disease states.

SUMMARY OF THE INVENTION

The present invention relates to compounds, compositions and a method of inhibiting lipoxygenase enzymes, particularly 5-lipoxygenase, in a mammal in need of such treatment by administering to such mammals a composition that comprises a nontoxic pharmaceutically acceptable carrier and a compound of Formula I, or its pharmaceutically acceptable salt, in an amount effective to inhibit such activity. A compound of the invention has a structure that corresponds to general Formula I below:

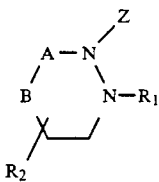

Formula I wherein A is selected from the group of C=O and C=S. B is selected from the group consisting of oxygen, $NR_4$ or $CR_5R_6$. $R_1$ is an optionally substituted aromatic carbocyclic or aromatic heterocyclic group having from one to three fused and non-fused ring systems, each ring having from five to seven atoms. The heteroatoms in the heterocyclic aromatics are selected from one or more of oxygen, nitrogen, and sulfur.

$R_2$ is a member selected independently at each occurrence from one or more substituents of hydrogen, $-NR_8R_9$, halogen, alkyl, $-COOR_7$, hydroxy, cyano, alkoxy, aryloxy, $-NHCOR_{10}$, alkenyl, aryl, arylalkyl, acyl, alkylthio, alkynyl, cycloalkyl, cycloalkenyl, deuterium, tritium, or an alkyl, cycloalkyl, alkenyl, cycloalkenyl or arylalkyl group which is substituted with a group selected independently at each occurence from a group of the formula: halogen, —OR, —CN, —NRCONRR, —NR—CSNRR, —NRCOOR, alkythioalkoxy, —OCONRR, —OCOR, $-(O(CHR)_n)_mOR$, —NRC(NR)NRR, —NRC(NCN)NRR, —C=NOR, —C=N—NRR, —COR, —CONRR, —CO₂R, —CSNRR, —SOR, —R, SR, —SO₂NRR, and —CF₃ where R is independently selected at each occurence from: hydrogen, hydroxy, alkoxy, aryloxy, alkenyl, alkyl, arylalkyl, cycloalkyl, aryl or an optionally substituted aromatic carbocyclic or heterocyclic group as defined above.

$R_4$ is a member selected from the group consisting of: hydrogen, alkyl, —COOR₇, hydroxy, alkoxy, aryloxy, arylalkyl, acyl, cycloalkyl, cycloalkenyl, deuterium, tritium, or an alkyl, cycloalkyl, alkenyl, cycloalkenyl or arylalkyl group which is substituted with a group selected independently from the group consisting of halogen, —OR, —CN, —NRCONRR, —NR—CSNRR, —NRCOOR, alkylthioalkoxy, —OCONRR, —OCOR, $-(O(CHR)_n)_mOR$, —NRC(NR)NRR, —NRC(NCN)NRR, —C=NOR, —C=N—NRR, —COR, —CONRR, —CO₂R, —CSNRR, —SOR, —SO₂R, SR, —SO₂NRR, and —CF₃ where R is independently selected from the group consisting of hydrogen, hydroxy, alkoxy, aryloxy, alkenyl, alkyl, arylalkyl, cycloalkyl, aryl or an optionally substituted aromatic carbocyclic or heterocyclic group as defined above;

m and n are numerals, each of which independently has a value of one to 11.

Z is hydrogen, a pharmaceutically acceptable cation, or a metabolically cleaveable group.

$R_5$ and $R_6$ are independently selected from the groups included in the definition for $R_2$ above.

$R_7$ is selected independently at each instance from alkyl, alkylaminoalkyl, alkylaryl, and aryl.

$R_8$ and $R_9$ are independently selected from hydrogen and alkyl.

$R_{10}$ is an alkyl group; with the proviso that when B=CH₂, A=CO, and $R_2$=Z=H, $R_1$ is other than phenyl.

Pharmaceutically acceptable salts of the above compounds are also contemplated.

A preferred embodiment of the present invention is where B=NR₄, and R₄=hydrogen, acyl and arylalkyl.

A more preferred group of the triazinone compounds are those of the formula:

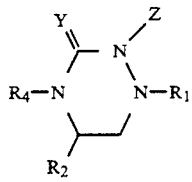

wherein Y=O or S. Z is hydrogen, a pharmaceutically acceptable salt or metabolically cleavable group.

R₁ is an unsubstituted or substituted phenyl having one or more substituents selected from the group consisting of alkyl, alkylthio, arylalkoxyoxy and halogen.

R₂ is selected from the group consisting of alkyl, alkanol, alkoxyalkoxyalkyl, and carboalkoxy.

R₄ is hydrogen, acyl, and arylalkyl.

The most preferred triazinone species are the following:

1-(3-chlorophenyl)-2H,4H-tetrahydro-1,2,4-triazin-3-one

D,L-5-methyl-1-phenyl-2H,4H-tetrahydro-1,2,4-triazin-3-one

D,L-5-methyl-1-(3-chlorophenyl)-2H,4H-tetrahydro-1,2,4-triazin-3-one.

1-phenyl-2H,4H-tetrahydro-1,2,4-triazin-3-one 1-(2-pyridyl)-2H,4H-tetrahydro-1,2,4-triazin-3-one 5-(2-methoxyethoxymethyl)-1-phenyl-2H,4H-tetrahydro-1,2,4-triazin-3-one 1-(3-methylphenyl)-2H,4H-tetrahydro-1,2,4-triazin-3-one 1-phenyl-2H,4H-tetrahydro-1,2,4-triazin-3-thione 1-(3-chlorophenyl)-2H,4H-tetrahydro-1,2,4-triazine-3-thione 4-acetyl-1-phenyl-2H,4H-tetrahydro-1,2,4-triazine-3-one The method of treatment for inhibiton of lipoxygenase enzymes, in a mammal in need of such treatment, also contemplates the use of compounds of Formula I wherein B=CH₂, A=CO, R₂=Z=H and R₁=phenyl.

DETAILED DESCRIPTION OF THE INVENTION

The present invention relates in one aspect to compounds and the process of making said compounds which are useful for inhibiting lipoxygenase enzymes and as chemical intermediates for pharmaceuticals. This invention particularly relates to compounds which inhibit 5-lipoxygenase. Another aspect of the invention relates to compositions and methods for inhibiting lipoxygenase enzymes in humans and animal hosts in need of such treatment.

A compound of the invention has a structure that corresponds to general Formula I, below:

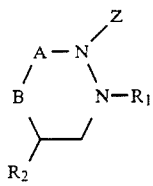

Formula I wherein A is selected from C=O and C=S; and B is a memeber selected from the group consisting of O, NR₄, and CR₅R₆.

R1 is an aromatic carbocyclic or heterocyclic group having from one to three fused or non-fused rings with each ring having from five to seven atoms. The heteroatoms in the heterocyclic group are selected from one or more of oxygen, nitrogen, and sulfur. Aromatic carbocycles are selected from such examples as, but not limited to: phenyl, naphthyl, biphenyl, anthracenyl, and biphenylene. Heterocyclic groups are selected from such examples as, but not limited to; pyridyl, pyrimidyl, pyridazinyl, thienyl, furyl, imidazolyl, thiazolyl, indolyl, oxazole, trazole, tetrazole, quinolinyl, isoquinolinyl, benzimidazolyl, benzothiazolyl, benzthienyl, phenothiazinyl, benzoxazolyl and naphthyridyl.

The aromatic carbocyclic or heterocyclic group can be unsubstituted or substituted with one or more substituents selected independently at each occurrence from the group consisting of hydrogen, deuterium, tritium, halogen, hydroxy, COOR₇, acyl, cyano, nitro, alkoxy, epoxy, aryl, aryloxy, arylalkoxy, alkyl, polyhaloalkyl, arylalkyl, alkenyl, alkynyl, cycloalkyl, cycloalkenyl, alkylthio, alkylsulfonyl, arylthio, carboxaldehyde, heterocyclic group or an alkyl, cycloalkyl, alkenyl, cycloalkenyl or arylalkyl group which is substituted with a group selected independently from the group consisting of —OR, —CN, halogen, —NRCONRR, —NRCSNRR, —NRCOOR, —OCONRR, —OCOR, —N(R)COR, —(O(CHR)ₙ)ₘOR, —NR—C(NR)NRR, —NRC(NCN)NRR, —C(R)=NOR, =NOR, =N(R)NRR, —C(R)=N—NRR, —COR, —CONRR, —CO₂R, —CSNRR, —SOR, —SO₂R, —SO₂NRR, —CF₃ where R is independently selected from the group consisting of hydrogen, hydroxy, alkoxy, aryloxy, alkenyl, alkyl, cycloalkyl or an optionally substituted carbocyclic or heterocyclic group as defined above; m and n are numerals each of which independently have values of 1-11.

R₂ is a member selected independently from the group consisting of hydrogen, halogen, deuterium, hydroxy, tritium, cyano, —NR₈R₉, NHCOR₁₀, COOR₇, —CONR₈R₉, acyl, —C(R)=NOR, aryl, heterocyclic group, alkylthio, arylthio, arylalkyl, alkoxy, alkoxy(hydroxy)alkyl, aryloxy, alkyl, alkenyl, alkynyl, cycloalkyl, cycloalkenyl or an alkyl, cycloalkyl, alkenyl, cycloalkenyl or arylalkyl group which is substituted with a group selected independently from the group consisting of halogen, —OR, —CN, —NR₈R₉, —NRCONRR, —NRCSNRR, —NRCOOR, alkylthioalkoxy, —OCONRR, —OCOR, —(O(CHR)ₙ)ₘOR, —NRC(NR)NRR, —NRCOR, —NRC(NCN)NRR, —C(R)=NOR, —C(R)=N—NRR, —COR, —CONRR, —CO₂R, CSNRR, —SOR, —SO₂R, SR, —SO₂NRR, —CF₃, —CH(NH₂)COOR, —O(CH₂)ₙCOOR, —NH(CH₂)ₙCOOR, alkenyloxy, alkynyloxy, where R is independently selected from the group consisting of hydrogen, hydroxy, alkoxy, aryloxy, alkenyl, alkyl, arylalkyl, cycloalkyl, aryl or an optionally substituted aromatic carbocyclic or heterocyclic group as defined above, with the proviso that when B is O or $NR_4$ then $R_2$ is not halogen, $-NR_8R_9$, alkylthio, alkoxy, aryloxy or arylthio.

$R_4$ is a member selected from the group consisting of: hydrogen, alkyl, $-COOR_7$, hydroxy, alkoxy, aryloxy, arylalkyl, arylalkoxyalkyl, acyl, cycloalkyl, cycloalkenyl, deuterium, tritium, or an alkyl, cycloalkyl, alkenyl, cycloalkenyl or arylalkyl group which is substituted with a group selected independently at each occurrence from the group consisting of halogen, $-OR$, $-CN$, $-NRCONRR$, $-NRCCSNRR$, $-NRCOOR$, alkylthioalkoxy, $-OCONRR$, $-OCOR$, $-N(R)COR$, $-(O(CHR)_n)_mOR$, $-NRC(NR)NRR$, $-NRC(NCN)NRR$, $-C(R)=NOR$, $-C(R)=N-NRR$, $-COR$, $-CONRR$, $-CO_2R$, $-CSNRR$, $-SOR$, $-SO_2R$, $SR$, $-SO_2NRR$, and $-CF_3$ where R is independently selected from the group consisting of hydrogen, hydroxy, alkoxy, aryloxy, alkenyl, alkyl, arylalkyl, cycloalkyl, aryl or an optionally substituted aromatic carbocyclic or heterocyclic group as defined above; m and n are as defined above.

$R_7$ is selected independently from the group consisting of alkyl, alkylaminoalkyl, alkylaryl, and aryl.

$R_8$ and $R_9$ are independently selected from hydrogen and alkyl.

Z is hydrogen, a pharmaceutically acceptable cation, or is metabolically cleaved to provide the corresponding hydrogen or salt compound.

$R_{10}$ is an alkyl group; and the pharmaceutically acceptable salts thereof; with the proviso that when $B=CH_2$, $A=CO$, and $R_2=Z=H$, $R_1$ is other than phenyl.

The term "metabolically cleaveable group" refers to groups which can be cleaved from the molecule by metabolic processes and be substituted with a hydrogen, a salt or form a group which yields an active enzyme inhibitor when the cleaveable group is removed from the molecule. Examples of metabolically cleaveable groups include acetyl, methoxycarbonyl, benzyl, benzoyl, COR, COOR, $-CH_2COOR$, CONRR, $-CH_2CONRR$, $-CH_2OR$, and $-CH_2SR$ where R is selected independently at each occurrence from alkyl, aryl, arylalkyl or an aryl substituted with one or more of alkyl, halogen, hydroxy or alkoxy.

A preferred embodiment of the present invention is the triazinone group of compounds, in which $B=NR_4$, and $R_4=$hydrogen, acyl and arylalkyl.

A more preferred group of the triazinone compounds are those of the formula:

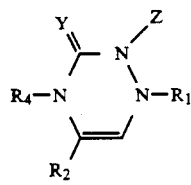

wherein Y=O or S. Z is hydrogen, a pharmaceutically acceptable salt or metabolically cleavable group.

$R_1$ is an unsubstituted or substituted phenyl having one or more substitutents selected from the group consisting of alkyl, alkylthio, arylalkyloxy and halogen.

$R_2$ is selected from the group consisting of alkyl, alkanol, alkoxyalkoxyalkyl, and carboalkoxy.

$R_4$ is hydrogen and acyl.

The most preferred group of triazinone compounds are the following species:

1-(3-chlorophenyl)-2H,4H-tetrahydro-1,2,4-triazin-3-one.

D,L-5-methyl-1-phenyl-2H,4H-tetrahydro-1,2,4-triazin-3-one.

D,L-5-methyl-1-(3-chlorophenyl)2H,4H-tetrahydro-1,2,4-triazin-3-one.

1-phenyl-2H,4H-tetrahydro-1,2,4-triazin-3-one.

1-(2-pyridyl)-2H,4H-tetrahydro-1,2,4-triazin-3-one.

5-(2-methoxyethoxymethyl)-1-phenyl-2H,4H-tetrahydro-1,2,4-triazin-3-one 1-(3-methylphenyl)-2H,4H-tetrahydro-1,2,4-triazin-3-one.

1-phenyl-2H,4H-tetrahydro-1,2,4-triazin-3-thione.

1-(3-chlorophenyl)-2H,4H-tetrahydro-1,2,4-triazine-3-thione.

4-acetyl-1phenyl-2H,4H-tetrahydro-1,2,4-triazine-3-one

The replacement of any carbon atom with carbon isotopes C13 or C14 as well as the replacement of any hydrogen by either deuterium or tritium, on the aromatic carbocylic or heterocyclic rings or the $R_2$ group, is also contemplated. Also within the scope of this invention are the optical isomers, enatiomers and racemic mixtures of the disclosed compounds herein, for use as lipoxygenase inhibitors.

Another aspect of this invention is a composition containing an effective amount of a compound of Formula I in combination with a pharmaceutically acceptable carrier, adjuvant or diluent. The present invention further contemplates a method of treatment. Here, an effective amount of an above-noted composition is administered to an animal or human host.

Examples of compounds which can be administered according to the method of this invention and/or are novel compounds of this invention include the following:

1-(3'-cyanophenyl)-2H-tetrahydropyridazin-3-one
1-(4'-cyanophenyl)-2H-tetrahydropyridazin-3-one
1-(3'-methoxyphenyl)-2H-tetrahydropyridazin-3-one
1-(4'-methoxyphenyl)-2H-tetrahydropyridazin-3-one
1-(4'-butoxyphenyl)-2H-tetrahydropyridazin-3-one
1-(4'-phenoxyphenyl)-2H-tetrahydropyridazin-3-one
1-(4'-trifluoromethylphenyl)-2H-tetrahydropyridazin-3-one
1-(3'-trifluoromethylphenyl)-2H-tetrahydropyridazin-3-one
1-(2'-ethylphenyl)-2H-tetrahydropyridazin-3-one
1-(3'-ethylphenyl)-2H-tetrahydropyridazin-3-one
1-(4'-ethylphenyl)-2H-tetrahydropyridazin-3-one
1-(4'-butylphenyl)-2H-tetrahydropyridazin-3-one
1-(4'-tert-butylphenyl)-2H-tetrahydropyridazin-3-one
1-(3'-pentylphenyl)-2H-tetrahydropyridazin-3-one
1-(4'-octylphenyl)-2H-tetrahydropyridazin-3-one
1-(3'-ethoxycarbonylphenyl)-2H-tetrahydropyridazin-3-one
1-(4'-ethoxycarbonylphenyl)-2H-tetrahydropyridazin-3-one
1-(3'-hydroxymethylphenyl)-2H-tetrahydropyridazin-3-one
1-(4'-methylsulfonylphenyl)-2H-tetrahydropyridazin-3-one
1-(3'-methanalphenyl)-2H-tetrahydropyridazin-3-one
1-(5'-indanyl)-2H-tetrahydropyridazin-3-one
1-(5'-tetrahydronaphthyl)-2H-tetrahydropyridazin-3-one
1-(3-dibenzofuranyl)-2H-tetrahydropyridazin-3-one 1-(3',5'-dimethylphenyl)-2H-tetrahydropyridazin-3-one
1-(2',6'-dimethylphenyl)-2H-tetrahydropyridazin-3-one
1-(3',5'-dichlorophenyl)-2H-tetrahydropyridazin-3-one
1-(2',3'-difluorophenyl)-2H-tetrahydropyridazin-3-one
1-(2',6'-difluorophenyl)-2H-tetrahydropyridazin-3-one
1-(2',5'-difluorophenyl)-2H-tetrahydropyridazin-3-one
1-(3',5'-difluorophenyl)-2H-tetrahydropyridazin-3-one
1-(4'-fluoro-3'-trifluoromethylphenyl)-2H-tetrahydropyridazin-3-one
1-(3'5'-bistrifluoromethylphenyl)-2H-tetrahydropyridazin-3-one
1-(4'-bromo-3'-methylphenyl)-2H-tetrahydropyridazin-3-one
1-(4'-(2-diethylaminoethyl)carboxyl)-2H-tetrahydropyridazin-3-one
1-(3,4,5-trichlorophenyl)-2H-tetrahydropyridazin-3-one
1-(N-ethyl-3-dibenzopyrolyl)-2H-tetrahydropyridazin-3-one
1-(3'-cyanophenyl)-4-methyl-2H-tetrahydropyridazin-3-one
1-phenyl-4-butyl-2H-tetrahydropyridazin-3-one
1-phenyl-4-benzyl-2H-tetrahydropyridazin-3-one
1-phenyl-5-butyl-2H-tetrahydropyridazin-3-one
1-(4'-phenoxyphenyl)-4-methyl-2H-tetrahydropyridazin-3-one
1-(3-methylphenyl)-2H-tetrahydropyridazin-3-one
1-(2'-methylphenyl)-2H-tetrahydropyridazin-3-one
1-(4'-methylphenyl)-2H-tetrahydropyridazin-3-one
1-(2'-chlorophenyl)-2H-tetrahydropyridazin-3-one
1-(3'-chlorophenyl)-2H-tetrahydropyridazin-3-one
1-(4'-chlorophenyl)-2H-tetrahydropyridazin-3-one
1-(3'-bromophenyl)-2H-tetrahydropyridazin-3-one
1-(2'-fluorophenyl)-2H-tetrahydropyridazin-3-one
1-(3'-fluorophenyl)-2H-tetrahydropyridazin-3-one
1-(4'-fluorophenyl)-2H-tetrahydropyridazin-3-one
1-(2-benzoxazole)-2H-tetrahydropyridazin-3-one
1-(2-pyrimidyl)-2H-tetrahydropyridazin-3-one
1-(2-pyridyl)-2H-tetrahydropyridazin-3-one
1-(2,4-dinitrophenyl)-2H-tetrahydropyridazin-3-one
1-phenyl-4-(2-propenyl)-2H-tetrahydropyridazin-3-one
1-phenyl-4-(2-methyl-2-propenyl)-2H-tetrahydropyridazone
1-phenyl-4-ethyloxymethyl-2H-tetrahydropyridazone
1-phenyl-4-benzyloxymethyl-2H-tetrahydropyridazone
1-phenyl-4-methylthiomethyl-2H-tetrahydropyridazone
1-phenyl-4-phenylthiomethyl-2H-tetrahydropyridazone
1-phenyl-4-(3-methyl-1-oxo-but-2-enyl)-2H-tetrahydropyridazin-3-one
1-phenyl-4-(hydroxymethylphenyl)-2H-tetrahydropyridazin-3-one
1-(3-chlorophenyl)-2H,4H-tetrahydro-1,2,4-triazin-3-one
D,L-5-methyl-1-phenyl-2H,4H-tetrahydro-1,2,4-triazin-3-one
D,L-5-methyl-1-(3-chlorophenyl)2H,4H-tetrahydro-1,2,4-triazin-3-one
1-phenyl-2H,4H-tetrahydro-1,2,4-triazin-3-one
5-(2-methoxyethoxymethyl)-1-phenyl-2H,4H-tetrahydro-1,2,4-triazin-3-one
1-(2-pyridyl)-2H,4H,tetrahydro-1,2,4-triazine-3-one
1-(4-methylphenyl)-2H,4H-tetrahydro-1,2,4-triazin-3-one
1-(2-methylphenyl)-2H,4H-tetrahydro-1,2,4-triazin-3-one
1-(3-methylphenyl)-2H,4H-tetrahydro-1,2,4-triazin-3-one
4-phenyl-3H-trihydro-1,3,4-oxadiazin-2-one
1-phenyl-2-benzyloxymethyl-2H-tetrahydropyridazin-3-one
1-phenyl-2-benzyl-2H-tetrahydropyridazin-3-one
1-phenyl-2-carbomethoxy-2H-tetrahydropyridazin-3-one
1-phenyl-2-propionyl-2H-tetrahydropyridazin-3-one
1-phenyl-2-benzoyl-2H-tetrahydropyridazin-3-one
1-phenyl-2-methoxycarbonylmethyl-2H-tetrahydropyridazin-3-one
1-(3'-benzyloxymethylphenyl)-2-benzyl-2H-tetrahydropyridazin-3-one
1-phenyl-2H,4H-tetrahydro-1,2,4-triazin-3-thione
1-(3-chlorophenyl)-2H,4H-tetrahydro-1,2,4-triazine-3thione
1-phenyl-2H-tetrahydropyridazin-3-thione
1-(3'-fluorophenyl)-2H-tetrahydropyridazin-3-thione
1-(3'-methylphenyl)-2H-tetrahydropyridazin-3-thione.

The term "alkyl" is used herein to mean straight and branched chain radicals of 1–12 carbon atoms, including but not limited to, methyl, ethyl, n-propyl, isopropyl, n-butyl, sec-butyl, isobutyl, tert-butyl, and the like.

The term "alkenyl" is used herein to mean straight and branched chain unsaturated radicals of 1–12 carbon atoms, including, but not limited to ethenyl, 1-propenyl, 2-propenyl, 2-methyl-1-propenyl, 1-butenyl, 2-butenyl, and the like.

The term "alkoxy" is used herein to mean straight and branched chained oxygen ether radicals of 1–12 carbon atoms, including, but not limited to methoxy, ethoxy, isopropoxy, n-butoxy, sec-butoxy, isobutoxy, tert-butoxy, and the like.

The term "carbonyl" or "alkoyl" or "acyl" is used herein to mean COM wherein M is a straight or branched radical, phenyl or benzyl including, but not limited to, formyl, acetyl, propionyl, butyryl, isobutyryl, pivaloyl, benzoyl, phenylacetyl, and the like.

The term "aryl" is used herein to mean substituted and unsubstituted aromatic radicals, including, but not limited to phenyl, 1-naphthyl, 2-naphthyl, and the like.

The terms "halo" and "halogen" as used herein refer to radicals derived from the elements fluorine, chlorine, bromine, and iodine.

The term "aryloxy" as used herein refers to substituted or unsubstituted aryl ethers including, but not limited to phenoxy, 1-naphthoxy, 2-naphthoxy, and the like.

The term "arylalkoxy" as used herein refers to an alkoxy radical substituted with an aryl group, including, but not limited to benzyloxy and the like.

The term "arylalkoxyalkyl" as used herein refers to an alkyl radical substituted by an arylalkoxy group.

The term "alkoxy(hydroxy)alkyl" as used herein refers to an alkyl radical substituted by an alkoxy group and a hydroxy group including, but not limited to 1-hydroxy-2-methoxy-ethyl and the like.

The term "arylalkyl" as used herein refers to substituted or unsubstituted aryl alkyl radicals including but not limited to phenylmethyl (benzyl), 1-phenylethyl, 2-phenylethyl, 1-naphthylethyl.

The term "pharmaceutically acceptable cation" or "salt" is used herein to mean the non-toxic cations based on the alkali and alkaline earth metals, such as sodium, lithium, potassium, magnesium, and the like, as well as those based on non-toxic ammonium, quaternary ammonium, and amine cations, including, but not limited to, ammonium, tetramethylammonium, tetraethylammonium, methylamine, dimethylamine, trimethylamine, triethylamine, ethylamine and the like.

The term "alkylthioalkoxy" as used herein refers to —$(CH_2)_sD(CH_2)_nG(CH_2)_pCH_3$ wherein D is O or S and G is S when D is O or G is O when D is S, and s and n are numerals independently having a value from 1 to about 11 and p is a numeral having a value from 0 to about 11.

The term "alkoxyalkoxyalkyl" as used herein refers to —$CH_2(O(CHR)_n)_mOR$ wherein R is as defined above and n and m are numerals independently having a value form 1 to about 11, including, but not limited to, methoxymethoxy and methoxyethoxyethoxy.

The term "alkylthioalkyl" as used herein refers to a sulfur ether, including groups of the formula —$S(CH_2)_nCH_3$ where n is as defined above.

The term "arylthio" as used herein refers to groups of the formula —$S(Ar)$ where Ar is an aryl group.

The term "arylsulfoxide" as used herein refers to a group of the formula —$SO(Ar)$ where Ar is an aryl group.

The term "polyhaloalkyl" as used herein refers to an alkyl radical in which two or more hydrogens are replaced by halogen, including but not limited to, trifluoromethyl, dichloroethyl and the like.

The terms "arylsulfonyl" and "alkylsulfonyl" as used herein refer to —$SO_2Q$ where Q is an aryl group or an alkyl group, respectively.

The term "alkylaminoalkyl" as used herein refers to an alkyl group substituted with an amino group mono- or disubstituted with an alkyl group. Alkylamino-alkyl groups include methylaminomethyl and the like.

The terms "alkenyloxy" and "alkynyloxy" as used herein refer to alkoxy radicals in which the chain of carbon atoms contains one or more double or triple bonds, respectively.

Formulation of the Pharmaceutical Composition

This invention also provides for compositions in unit dosage form for the inhibition of lipoxygenase activity in a human or lower animal host in need of such treatment, comprising a compound of this invention and one or more non-toxic pharmaceutically acceptable carriers, adjuvants or vehicles which are collectively referred to herein as carriers. The amount of active ingredient that may be combined with such materials to produce a single dosage form will vary depending upon various factors, as indicated above.

A variety of materials can be used as carriers in a composition of this invention, are available i the pharmaceutical arts. Injectable preparations, such as oleaginous solutions, suspensions or emulsions, may be formulated according to know art, using suitable dispersing or wetting agents and suspending agents, as needed. The sterile injectable preparation may employ a non-toxic parenterally acceptable diluent or solvent as, for example, sterile nonpyrogenic water or 1,3-butanediol. Among the other acceptable vehicles and solvents that may be employed are 5% dextrose injection, Ringer's injection and isotonic sodium chloride injection (as described in the USP/NF). In addition, sterile, fixed oils are conventionally employed as solvents or suspending media. For this purpose, any bland fixed oil may be used, including synthetic mono-, di- or triglycerides. Fatty acids such as oleic acid can also be used in the preparation of injectable compositions.

Suppositories for rectal administration of the compound of this invention can be prepared by mixing the drug with suitable non-irritating excipient such as cocoa butter and polyethylene glycols, which are solid at ordinary temperatures but liquid at body temperature and which, therefore, melt in the rectum and release the drug.

Solid dosage forms for oral administration include capsules, tablets, pills, troches, lozenges, powders and granules. In such solid dosage forms, the active compound may be admixed with at least one inert diluent such as sucrose, lactose or starch. Such dosage forms may also comprise, as is normal practice, pharmaceutical adjuvant substances, e.g., stearate lubricating agents. In the case of capsule, tablets and pills, the dosage forms may also comprise buffering agents. Solid oral preparations can also be prepared with enteric or other coatings which modulate release of the active ingredients.

Liquid dosage forms for oral administration include pharmaceutically acceptable emulsions, solutions, suspensions, syrups and elixirs containing inert nontoxic diluents commonly used in the art, such as water and alcohol. Such compositions may also comprise adjuvants, such as wetting agents, emulsifying, suspending, sweetening, flavoring and perfuming agents.

Method of Treatment

This invention provides a method of treatment of inhibiting lipoxygenase, in particular 5-lipoxygenase activity, in a human or lower animal host in need of such treatment which method comprises administration to the human or lower animal host of a previously described composition that contains a compound of Formula I and also the compounds wherein $B=CH_2$, $A=CO$, and $R_2=Z=H$ and $R_1=$phenyl, in an amount effective to inhibit lipoxygenase activity in the host. The compounds of the present invention may be administered orally, parenterally or topically in dosage unit formulations containing conventional nontoxic pharmaceutically acceptable carriers, adjuvants and vehicles as desired.

The term parenteral as used herein includes subcutaneous, intravenous, intraarterial injection or infusion techniques, without limitation. The term "topically" encompasses administration rectally and by inhalation spray, as well as by the more common routes of the skin and mucous membranes of the mouth and nose.

Total daily dose of the compounds of this invention administered to a host in single or divided doses maybe in amounts, for example, of from about 0.001 to about 100 mg/kg body weight daily and more usually 0.01 to 10 mg/kg/day. Dosage unit compositions may contain such amounts of such submultiples thereof as may be used to make up the daily dose. It will be understood, however, that the specific dose level for any particular patient will depend upon a variety of factors, including the body weight, general health, sex, diet, time and route of administration, rates of absorption and excretion, combination with other drugs and the severity of the particular disease being treated.

Synthesis of the Compounds

I) Pyridazinone Synthesis

Pyridazinone compounds of this invention can be prepared by reaction Schemes I-III below. In most cases, any one of the three schemes can be used to make any of the exemplary pyridazinone compounds below.

However, for some compounds, either only one of the specific Schemes I-III can be used, or one of the specific Schemes I-III produces the compound in a purer form or in a higher yield than the other Schemes. Thus, the Examples are grouped according to preferred synthetic scheme. The compounds of Examples following Scheme I are preferably made according to Scheme I, and so on. When not specified all temperature ranges are in degress centigrade.

a) Scheme I

Pyridazinones of the general Formula II are prepared by the sequence of reactions outlined in Scheme I. The meanings of $R_1$, $R_2$ and the like correspond to the definitions provided above. A primary amine (1) is condensed with a substituted ethyl bromobutyrate (2) using diisopropylethylamine (for example, EtN(iPr)$_2$) as a base to yield the secondary amine (3). N-Nitrosation yields the intermediate N-nitroso compound (4). Reduction of (4) with zinc powder produces the intermediate hydrazine (5) which is intramolecularly cyclized by treatment with an appropriate base (such as sodium methoxide, magnesium ethoxide, or potassium tert-butoxide) to produce the pyridazinone structure II. The application of substituted ethylbromobutyrates (2) is described in several of the specific examples which follow.

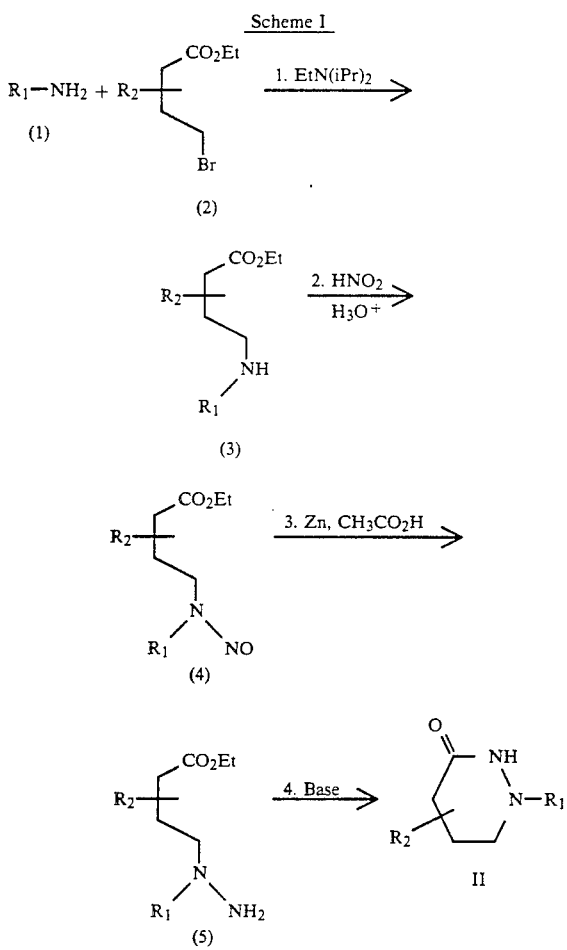

Scheme 1

EXAMPLE 1

1-(3'-cyanophenyl)-2H-tetrahydropyridazin-3-one
Formula II, $R_1$=3-cyanophenyl; $R_2$=H a) Ethyl 4-(3'-aminobenzonitrile) butyrate 3-Aminobenzonitrile (24.7 g, 0.21 mole), diisopropylethylamine (27.0 g, 0.21 mole) and ethyl 4-bromobutyrate (40.8 g, 0.21 mole) were dissolved in benzene (150 mL), and the mixture was refluxed with stirring under a nitrogen atmosphere for five days. The mixture was allowed to cool to room temperature and water (100 mL) was added. The organic layer was separated, dried over MgSO$_4$, filtered and evaporated to give a residue (50.7 g). A sample was crystallized from hexane to give colorless crystals, mp 62°-63° C.

Mass spectrum M+ =232.

b) Ethyl 4-(3'-cyano-N-nitosoaniline) butyrate.

The residue from part a (46 g) was suspended in a solution of water (200 mL) containing concentrated HCl (30 mL), and was cooled to 5° C. With efficient mechanical stirring, a solution of NaNO$_2$ (14.0 g) in water (50 mL) was added. The mixture was stirred for an additional one hour at 5° C. and then extracted with benzene (3×100 mL). The combined organic extract was evaporated to give an oily residue (47.5 g).

c) Ethyl 4-(3'-cyano-N-aminoaniline) butyrate.

The residue from part b (47 g) was dissolved in acetic acid (60 mL) and added dropwise to a mechanically stirred suspension of zinc dust (56.0 g) in water (90 mL). The temperature of the mixture was controlled not to exceed 22° C. by external cooling with an ice bath. After the addition was complete the mixture was warmed to 80° C. for 20 min. and then allowed to cool to room temperature. Water (200 mL) and dichloromethane (200 mL) was added and with stirring the pH of the mixture was adjusted to 6-7 with 6N NaOH. The solution was filtered (to remove excess zinc) and the solids were washed with dichloromethane (50 mL). The combined filtrate was transferred to a separatory funnel and the layers were separated. The aqueous layer was extracted with dichloromethane (2×50 mL). The combined organic extract was dried over MgSO$_4$, filtered and evaporated to provide a residue (41.6 g).

d) 1(3'-cyanopnenyl)-2H-tetrahydropyridazin-3-one

The residue from part c (41 g) was dissolved in tetrahydrofuran (90 mL) and with stirring under nitrogen potassium tert-butoxide (3.0 g) was added. The mixture was refluxed for two hours, allowed to cool, and water (100 mL) was added. The pH of the solution was adjusted to 6 with 3N HCl, and the mixture was extracted with dichloromethane (2×100 mL). The combined organic extract was dried over MgSO$_4$, filtered and evaporated to give a solid product (9.7 g), mp 148°-149° C.

$^1$H NMR (300 MHz, CDCl$_3$) 1.97-2.08 (2 H, m), 2.43 (2 H, t), 3.77 (2 H, t), 7.20-7.28 (3 H, m), 7.37-7.43 (1 H, m), 8.37 (1 H, br s).

Mass spectrum: M+ =201

Anal.Calc'd. for C11H11N30 : C, 65.66; H, 5.51; N, 20.88.

Anal. Found : C, 65.30; H,5.57; N, 20.54.

EXAMPLE 2

1-(4'-cyanophenyl)-2H-tetrahydropyridazin-3-one (Formula II, $R_1$=4-cyanophenyl; $R_2$=H)

The title compound was prepared according to the method of Scheme I as described for Example 1, except using 4-aminobenzonitrile instead of 3-aminobenzonitrile as $R_1$-$NH_2$.

mp 149°-154° C.

$^1$H NMR(300 MHz,CDCl$_3$)2.02-2.14 (2 H, m), 2.41 (2H, t), 3.80 (2H, t), 6.99-7.06 (2H, m), 7.54-7.61 (2H, m), 8.22 (1H, br s).

Mass spectrum: M+ =201

Anal.Calc'd. for $C_{11}H_{11}N_3O$ : C, 65.66; H, 5.51; N, 20.88.

Anal. Found : C, 65.84; H,5.56; N, 20.62.

EXAMPLE 3

1-(3'-methoxyphenyl)-2H-tetrahydropyridazin-3-one (Formula II, $R_1$=3-methoxyphenyl; $R_2$=H)

The title compound was prepared according to the method of Scheme I as described for Example 1, except using 3-methoxyaniline instead of 3-aminobenzonitrile as $R_1$-$NH_2$.

mp 95.5° C.

$^1$H NMR(300 MHz,CDCl$_3$) 1.97 (2H, m), 2.42 (2H, t, J=7.5 Hz), 3.69 (2H, t J=6.5 Hz), 3.79 (3H, s), 6.57 (3H, m), 7.22 (1H, t, J=8 Hz), 7.47 (1H, br s).

Mass spectrum: M+ =206

EXAMPLE 4

1-(4'-methoxyphenyl)-2H-tetrahydropyridazin-3-one (Formula II, $R_1$=4-methoxyphenyl; $R_2$=H)

The title compound was prepared according to the method of Scheme I as described for Example 1, except using 4-methoxyaniline instead of 3-aminobenzonitrile as $R_1$-$NH_2$.

mp 78° C.

$^1$H NMR (300 MHz,CDCl$_3$) 1.90 (2H, m), 2.46 (2H, t, J=7.5 Hz), 3.62 (2H, t, J=6.3 Hz), 3.78 (3H, s), 6.90 (4H, m), 7.62 (1H, br s).

Mass spectrum: M+ =206

Anal.Calc'd. for $C_{11}H_{14}N_2O_2$ : C, 64.06; H, 6.84; N, 13.58.

Found : C, 64.05; H,6.92; N, 13.60.

EXAMPLE 5

1-(4'-butoxyphenyl)-2H-tetrahydropyridazin-3-one (Formula II, $R_1$=4-butoxyphenyl; $R_2$=H)

The title compound was prepared according to the method of Scheme I as described for Example 1, except using 4-butoxyaniline instead of 3-aminobenzonitrile as $R_1$-$NH_2$.

mp 68°-69° C.

$^1$H NMR(300 MHz,CDCl$_3$) 0.97 (3H, t), 1.42-1.56 (2H, m), 1.70-1.80 (2H, m), 1.84-1.94 (2H, m), 2.46 (2H, t,), 3.61 (2H, t), 3.92 (2H, t), 6.81-6.88 (2H, m), 6.90-6.95 (2H,m), 7.43 (1H, s).

Mass spectrum: M+ =248

Anal.Calc'd. for $C_{14}H_{20}N_2O_2$ : C, 67.71; H, 8.12; N, 11.28.

Found : C, 67.51; H, 8.12; N, 11.16.

EXAMPLE 6

1-(4'-phenoxyphenyl)-2H-tetrahydropyridazin-3-one (Formula II, $R_1$=4-phenoxyphenyl; $R_2$=H)

The title compound was prepared according to the method of Scheme I as described for Example 1, except using 4-phenoxyaniline instead of 3-aminobenzonitrile as $R_1$-$NH_2$.

mp 160° C.

$^1$H NMR(300 MHz,CDCl$_3$) 1.96 (2H, m), 2.47 (2H, t), 3.67 (2H, t), 6.90-7.11 (7H, m), 7.27-7.37 (2H,m), 7.61 (1H,s).

Mass spectrum: M+ =268

Anal.Calc'd for $C_{16}H_{16}N_2O_2$ : C, 71.62; H, 6.01; N, 10.44.

Found : C, 71.49; H, 5.95; N, 10.16.

EXAMPLE 7

1-(4'-trifluoromethylphenyl)-2H-tetrahydropyridazin-3-one (Formula II, $R_1$=4-trifluoromethylphenyl; $R_2$=H)

The title compound was prepared according to the method of Scheme I as described for Example 1, except using 4-trifluoromethylaniline instead of 3-aminobenzonitrile as $R_1$-$NH_2$.

mp 89° C.

$^1$H NMR(300 MHz,CDCl$_3$) 1.98-2.11 (2H, m), 2.41 (2H, t), 3.78 (2H, t), 7.06 (2H, d), 7.55 (2H, d), 7.89 (1H, brs).

Mass spectrum: M+ =244

Anal.Calc'd. for $C_{11}H_{11}F_3N_2O$ : C, 54.10; H, 4.54; N, 11.47.

Found : C, 54.20; H, 4.57; N, 11.33.

EXAMPLE 8

1-(3'-trifluoromethylphenyl)-2H-tetrahydropyridazin-3-one (Formula II, $R_1$=3-trifluoromethylphenyl; $R_2$=H)

The title compound was prepared according to the method of Scheme I as described for Example 1, except using 3-trifluoromethylaniline instead of 3-aminobenzonitrile as $R_1$-$NH_2$.

mp 130° C.

$^1$H NMR(300 MH$_z$,CDCl$_3$) 2.0 (2H, m), 2.43 (2H, t, J=7.5 Hz), 3.76 (2H, t, J=6 Hz), 7.2 (3H, m), 7.4 (1H, m), 8.07 (1H, b rs).

Mass spectrum: M+ =244

EXAMPLE 9

1-(2'-ethylphenyl)-2H-tetrahydropyridazin-3-one (Formula II, $R_1$=2-ethylphenyl; $R_2$=H)

The title compound was prepared according to the method of Scheme I as described for Example 1, except using 2-ethylaniline instead of 3-aminobenzonitrile as $R_1$-$NH_2$.

mp 135° C.

$^1$H NMR(300 MHz,CDCl$_3$) 1.27 (3H, t), 1.78-1.87 (2H, 2), 2.60 (2H, t), 2.70 (2H, q), 3.33-3.40 (2H, m), 7.08-7.26 (4H, m), 7.32 (1H, s).

Mass spectrum: M+ =204

Anal.Calc'd for $C_{12}H_{16}N_2O$ : C, 70.56; H, 7.89; N, 13.71.

Found : C, 71.02; H, 7.95; N, 13.74.

EXAMPLE 10

1-(3'-ethylphenyl)-2H-tetrahydropyridazin-3-one (Formula II, $R_1$=3-ethylphenyl; $R_2$=H)

The title compound was prepared according to the method of Scheme I as described for Example 1, except using 3-ethylaniline instead of 3-aminobenzonitrile as $R_1$-$NH_2$.

mp 90° C.

$^1$H NMR(300 MHz,CDCl$_3$) 1.22 (3H, t), 1.90–2.00 (2H, m), 2.43 (2H, t), 2.58–2.66 (2H, m), 6.78–6.85 (3H, m), 7.17–7.25 (1H, m), 7.57 (1H, brs).

Mass spectrum: M+ =204

Anal.Calc'd. for $C_{12}H_{16}N_2O$ : C, 70.56; H, 7.89; N, 13.71.

Found : C, 70.38; H, 7.87; N, 13.33.

EXAMPLE 11

1-(4'-ethylphenyl)-2H-tetrahydropyridazin-3-one (Formula II, $R_1$=4-ethylphenyl; $R_2$=H)

The title compound was prepared according to the method of Scheme I as described for Example 1, except using 4-ethylaniline instead of 3-aminobenzonitrile as $R_1$-$NH_2$.

mp 76° C.

$^1$H NMR(300 MHz,CDCl$_3$) 1.22 (3H, t), 1.85–1.98 (2H, m), 2.43 (2H, t), 2.60 (2H, q), 3.67 (2H, t), 6.89–6.96 (2H, m), 7.09–7.16 (2H, m), 7.61 (1H, s).

Mass spectrum: M+ =204

Anal Calc'd. for $C_{12}H_{16}N_2O$ : C, 70.56; H 7.89; N, 13.71.

Found : C, 70.39; H, 8.06; N, 13.65

EXAMPLE 12

1-(4'-butylphenyl)-2H-tetrahydropyridazin-3-one (Formula II, $R_1$=4-butylphenyl; $R_2$=H)

The title compound was prepared according to the method of Scheme I as described for Example 1, except using 4-butylaniline instead of 3-aminobenzonitrile as $R_1$-$NH_2$.

mp 84° C.

$^1$H NMR(300 MHz,CDCl$_3$) 0.93 (3H, t, J=7 Hz), 1.35 (2H, m), 1.58 (2H, m), 1.93 (2H, m), 2.45 (2H, t, J=7 Hz), 2.57 (2H, t, J=8 Hz), 3.68 (2H, t, J=6 Hz), 6.92 (2H, d, J=8 Hz), 7.12 (2H, d, J=8 Hz), 7.48 (1H, br s).

Mass spectrum: M+ =232

EXAMPLE 13

1-(4'-tert-butylphenyl)-2H-tetrahydropyridazin-3-one (Formula II, $R_1$=4-tert-butylphenyl; $R_2$=H)

The title compound was prepared according to the method of Scheme I as described for Example 1, except using 4-tert-butylaniline instead of 3-aminobenzonitrile as $R_1$-$NH_2$.

mp 162° C.

$^1$H NMR(300 MHz,CDCl$_3$) 1.3 (9H, s), 1.87–1.97 (2H, m), 2.43 (2H, t, J=7.5 Hz), 3.67 (2H, t, J=6.5 Hz), 6.93 (2H, m), 7.28 (2H, m), 7.60 (1H, br s).

Mass spectrum: M+ =232

EXAMPLE 14

1-(3'-pentylphenyl)-2H-tetrahydropyridazin-3-one (Formula II, $R_1$=3-pentylphenyl; $R_2$=H)

The title compound was prepared according to the method of Scheme I as described for Example 1, except using 3-pentylaniline instead of 3-aminobenzonitrile as $R_1$-$NH_2$.

$^1$H NMR(300 MHz,CDCl$_3$) 0.85 (3H, t, J=7 Hz), 1.25 (6H, m), 1.65 (3H, m), 1.90 (1H, m), 2.18 (1H, m), 2.38 (1H, m), 3.75 (2H, m), 6.95 (2H, m), 7.15 (1H, br s), 7.25 (2H, m).

Mass spectrum: M+ =246

EXAMPLE 15

1-(4'-octylphenyl)-2H-tetrahydropyridazin-3-one (Formula II, $R_1$=4-octylphenyl; $R_2$=H)

The title compound was prepared according to the method of Scheme I as described for Example 1, except using 4-octylaniline instead of 3-aminobenzonitrile as $R_1$-$NH_2$.

mp 68° C.

$^1$H NMR(300 MHz,CDCl$_3$) 0.88 (3H, t, J=7 Hz), 1.28 (10H, m), 1.58 (2H, m), 1.94 (2H, m), 2.44 (2H, t, J=7.5 Hz), 2.54 (2H, t, J=7.5 Hz), 3.67 (2H, t, J=6 Hz), 6.92 (2H, m), 7.11 (2H, m), 7.32 (1H, br s).

Mass spectrum: M+ =288

EXAMPLE 16

1-(3'-ethoxycarbonylphenyl)-2H-tetrahydropyridazin-3-one (Formula II, $R_1$=3-ethoxycarbonylphenyl; $R_2$=H)

The title compound was prepared according to the method of Scheme I as described for Example 1, except using 3-ethoxycarbonylaniline instead of 3-aminobenzonitrile as $R_1$-$NH_2$.

mp 90° C.

$^1$H NMR(300 MHz,CDCl$_3$) 1.40 (2H, t, J=7.5 H$_z$), 1.95–2.05 (2H, m), 2.43 (2H, t, J=7.5 Hz), 3.78 (2H, t, J=6.5 Hz), 4.38 (2H, q, J=7.5 Hz), 7.22 (1H, m), 7.47 (1H, m), 7.54 (1H, br), 7.64 (1H, m).

Mass spectrum: M+ =248

EXAMPLE 17

1-(4'-ethoxycarbonylphenyl)-2H-tetrahydropyridazin-3-one (Formula II, $R_1$=4-ethoxycarbonylphenyl; $R_2$=H)

The title compound was prepared according to the method of Scheme I as described for Example 1, except using 4-ethoxycarbonylaniline instead of 3-aminobenzonitrile as $R_1$-$NH_2$.

mp 74° C.

$^1$H NMR(300 MHz,CDCl$_3$) 1.38 (3H, t), 1.98–2.10 (2H, m), 2.49 (2H, t), 3.79 (2H, t), 4.30–4.42 (2H, q), 6.97–7.04 (2H, m), 7.90–8.10 (3H, m).

Mass spectrum: M+ =248

Anal.Calc'd. for $C_{13}H_{16}N_2O_3$ : C, 62.89; H, 6.50; N, 11.28.

Found : C, 60.81; H, 6.39; N, 11.21

EXAMPLE 18

1-(3'-hydroxymethylphenyl)-2H-tetrahydropyridazin-3-one (Formula II, $R_1$=3-hydroxymethylphenyl; $R_2$=H)

The title compound was prepared according to the method of Scheme I as described for Example 1, except using 3-hydroxymethylaniline instead of 3-aminobenzonitrile as $R_1$-$NH_2$.

mp 128° C.

$^1$H NMR(300 MHz, DMSO-$d_6$) 1.81 (2H, m), 2.16 (2H, t, J=7.5 Hz), 3.65 (2H, t, J=6 Hz), 4.45 (2H, d, J=6 Hz), 5.17 (1H, t, J=6 Hz), 6.80–6.85 (2H, m), 6.95 (1H, s), 7.21 (1H, t, J=8 Hz), 9.73 (1H, s).

Mass spectrum: M+ =206

EXAMPLE 19

1-(4'-methylsulfonylphenyl)-2H-tetrahydropyridazin-3-one (Formula II, $R_1$=4-methylsulfonylphenyl; $R_2$=H)

The title compound was prepared according to the method of Scheme I as described for Example 1, except using 4-methylsulfonylaniline instead of 3-aminobenzonitrile as $R_1$-$NH_2$.

mp 147° C.

$^1$H NMR(300 MHz, CDCl$_3$) 1.09 (2H, m), 2.41 (2H, t, J=7.5 Hz), 3.05 (3H, s), 3.83 (2H, t, J=7 Hz), 7.09 (2H, m), 8.05 (1H, s).

Mass spectrum: (M+1)=255

EXAMPLE 20

1-(3'-methanalphenyl)-2H-tetrahydropyridazin-3-one (Formula II, $R_1$=3-methanalphenyl; $R_2$=H)

The title compound was prepared according to the method of Scheme I as described for Example 1, except using 3-aminobenzaldehyde instead of 3-aminobenzonitrile as $R_1$-$NH_2$.

mp 113° C.

$^1$H NMR(300 MHz, CDCl$_3$) 1.97–2.08 (2H, m), 2.43 (2H, t, J=7.8 Hz), 3.80 (2H, t, J=6.6 Hz), 7.25–7.33 (1H, m), 7.45–7.53 (3H, m), 7.84 (1H, br s), 9.99 (1H, s).

Mass spectrum: M+ =204

EXAMPLE 21

1-(5-indanyl)-2H-tetrahydropyridazin-3-one (Formula II, $R_1$=5-indanyl ; $R_2$=H)

The title compound was prepared according to the method of Scheme I as described for Example 1, except using aminoindane instead of 3-aminobenzonitrile as $R_1$-$NH_2$.

$^1$H NMR(300 MHz, CDCl$_3$) 1.9 (2H, m), 2.1 (2H, m), 2.45 (2H, t), 2.85 (4H, m), 3.65 (2H, t), 6.7–7.2 (3H, m), 7.5 (1H, br s).

Mass spectrum: M+ =216

EXAMPLE 22

1-(5-tetrahydronaphthyl)-2H-tetrahydropyridazin-3-one (Formula II, $R_1$=5-tetrahydronaphthyl; $R_2$=H)

The title compound was prepared according to the method of Scheme I as described for Example 1, except using aminotetrahydronaphthylene instead of 3-aminobenzonitrile as $R_1$-$NH_2$.

mp 153° C.

$^1$H NMR(300 MHz, CDCl$_3$) 1.72–1.90 (6H, m), 2.60 (2H, t, J=7.2 Hz), 2.63–2.71 (2H, m), 2.77–2.85 (2H, m), 3.31–3.38 (2H, m), 6.90 (1H, d, J=7.5 Hz), 6.9- (1H, d, J=7.5 Hz), 7.11 (1H, t, J=7.5 Hz), 7.20 (1H, br s).

Mass spectrum: M+ =230

EXAMPLE 23

1-(3-dibenzofuranyl)-2H-tetrahydropyridazin-3-one (Formula II, $R_1$=3-dibenzofuranyl; $R_2$=H)

The title compound was prepared according to the method of Scheme I as described for Example 1, except using aminodibenzofuran instead of 3-aminobenzonitrile as $R_1$-$NH_2$.

mp 149° C.

$^1$H NMR(300 MHz, CDCl$_3$) 2.02 (2H, m), 2.48 (2H, t, J=7.5 Hz), 3.82 (2H, t, J=6.5 Hz), 7.03 (1H, dd, J=8.5, 2.2 Hz), 7.22 (1H, d, J=2.2 Hz), 7.32 (1Hz, ddd, J=7.7, 7.4, 1.1Hz), 7.39 (1H, br s), 7.40 (1H, ddd, J=8.1 7.4, 1.5 Hz)7.53 (1H, d, J=7.7 Hz), 7.85 (1H, d, J=8.5 Hz), 7.87 (1H, m).

Mass spectrum: M+ =266

EXAMPLE 24

1-(3',5'-dimethylphenyl)-2H-tetrahydropyridazin-3-one (Formula II, $R_1$=3,5-dimethylphenyl; $R_2$=H)

The title compound was prepared according to the method of Scheme I as described for Example 1, except using 2,6-dimethylaniline instead of 3-aminobenzonitrile as $R_1$-$NH_2$.

mp 146° C.

$^1$H NMR(300 MHz, CDCl$_3$) 1.94 (2H, m), 2.29 (6H, s), 2.44 (2H, t, J=7 Hz), 3.69 (2H, t, J=6 Hz), 6.63 (3H, s), 7.29 (1H, br s).

Mass spectrum: M+ =204

EXAMPLE 25

1-(2',6'-dimethylphenyl)-2H-tetrahydropyridazin-3-one (Formula II, $R_1$=2,6-dimethylphenyl; $R_2$=H)

The title compound was prepared according to the method of Scheme I as described for Example 1, except using 3,5-dimethylaniline instead of 3-aminobenzonitrile as $R_1$-$NH_2$.

$^1$H NMR(300 MHz, CDCl$_3$) 2.02 (2H, m), 2.35 (6H, s), 2.56 (2H, t, J=6.5 Hz), 3.32 (2H, m), 7.01 (3H, s), 7.55 (1H, br s).

Mass spectrum: M+ =204

EXAMPLE 26

1-(3',5'-dichlorophenyl)-2H-tetrahydropyridazin-3-one (Formula II, $R_1$=3,5-dichlorophenyl; $R_2$=H)

The title compound was prepared according to the method of Scheme I as described for Example 1, except using 3,5-dichloroaniline instead of 3-aminobenzonitrile as $R_1$-$NH_2$.

$^1$H NMR(300 MHz, CDCl$_3$) 2.05 (2H, m), 2.42 (2H, t, J=7 Hz), 3.70 (2H, t,J=6.5 Hz), 6.88 (2H, m), 6.94 (1H, m), 7.43 (1H, br s).

Mass spectrum: M+ =245

EXAMPLE 27

1-(2',3'-difluorophenyl)-2H-tetrahydropyridazin-3-one (Formula II, $R_1$=2,3-difluorophenyl; $R_2$=H)

The title compound was prepared according to the method of Scheme I as described for Example 1, except using 2,3-difluoroaniline instead of 3-aminobenzonitrile as $R_1$-$NH_2$.

mp 170° C.

$^1$H NMR(300 MHz, CDCl$_3$) 1.90 (2H, m), 2.54 (2H, t), 3.67 (2H, t), 6.83–7.08 (3H, m), 7.50 (1H, br s).

Mass spectrum: M+ =212

Anal.Calc'd. for $C_{10}H_{10}F_2N_2O$ : C, 56.60; H, 4.75; N, 13.20.

Found : C, 55.55; H, 4.71; N, 13.42

EXAMPLE 28

1-(2',6'-difluorophenyl)-2H-tetrahydropyridazin-3-one (Formula II, $R_1$=2,6-difluorophenyl; $R_2$=H)

The title compound was prepared according to the method of Scheme I as described for Example 1, except using 2,6-difluoroaniline instead of 3-aminobenzonitrile as $R_1$-$NH_2$.

mp 156° C.

$^1$H NMR(300 MHz, CDCl$_3$) 2.0 (2H, m), 2.62 (2H, t), 3.47 (2H, t), 6.88 (2H, m), 7.03–7.13 (1H, m), 7.60 (1H, br s).

Mass spectrum: M+ =212

Anal Calc'd. for $C_{10}H_{10}F_2N_2O$ : C, 56.60; H, 4.75; N, 13.20.

Found : C, 56.45; H, 4.80; N, 13.13

EXAMPLE 29

1-(2',5'-difluorophenyl)-2H-tetrahydropyridazin-3-one (Formula II, $R_1$=2,5-difluorophenyl; $R_2$=H)

The title compound was prepared according to the method of Scheme I as described for Example 1, except using 2,5-difluoroaniline instead of 3-aminobenzonitrile as $R_1$-$NH_2$.

mp 169° C.

$^1$H NMR(300 MHz, CDCl$_3$) 1.85 (2H, m), 2.54 (2H, t), 3.64–3.70 (2H, m), 6.65–6.75 (1H, m), 6.85–6.93 (2H, m), 6.97–7.07 (2H, m), 7.83 (1H, br s).

Mass spectrum: (M+1)=213

Anal.Calc'd for $C_{10}H_{10}F_2N_2O$ : C, 56.60; H, 4.75; N, 13.20.

Found : C, 56.45; H, 4.80; N, 13.13

EXAMPLE 30

1-(3',5'-difluorophenyl)-2H-tetrahydropyridazin-3-one (Formula II, $R_1$=3,5-difluorophenyl; $R_2$=H)

The title compound was prepared according to the method of Scheme I as described for Example 1, except using 3,5-difluoroaniline instead of 3-aminobenzonitrile as $R_1$-$NH_2$.

mp 128° C.

$^1$H NMR(300 MHz, CDCl$_3$) 2.0 (2H, m), 2.41 (2H, t), 3.70 (2H, t), 6.38 (1H, m), 6.51 (2H, m), 7.50 (1H, br s).

Mass spectrum: M+ =212

Anal.Calc'd for $C_{10}H_{10}F_2N_2O$ : C, 56.60; H, 4.75; N, 13.20.

Found.

Found : C, 56.58; H, 4.72; N, 13.10

EXAMPLE 31

1-(4'-fluoro-3'-trifluoromethylphenyl)-2H-tetrahydropyridazin-3-one (Formula II, $R_1$=4-fluoro-3-trifluoromethylphenyl; $R_2$=H)

The title compound was prepared according to the method of Scheme I as described for Example 1, except using 4-fluoro-3-trifluoromethylaniline instead of 3-aminobenzonitrile as $R_1$-$NH_2$.

mp 143° C.

$^1$H NMR(300 MHz, CDCl$_3$) 1.99 (2H, m), 2.46 (2H, t), 3.72 (2H, t), 7.1–7.25 (3H, m), 8.04 (1H, br s.).

Mass spectrum: M+ =262

Anal.Calc'd. for $C_{11}H_{10}F_4N_2O$ : C, 50.39; H, 3.84; N, 10.68.

Found : C, 50.45; H, 3.87; N, 10.54

EXAMPLE 32

1-(3',5'-bis-trifluoromethylphenyl)-2H-tetrahydropyridazin-3-one (Formula II, $R_1$=3,5-bis-trifluoromethylphenyl; $R_2$=H)

The title compound was prepared according to the method of Scheme I as described for Example 1, except using 3,5-bis-trifluoromethylaniline instead of 3-aminobenzonitrile as $R_1$-$NH_2$.

mp 145° C.

$^1$H NMR(300 MHz, CDCl$_3$) 2.05 (2H, m), 2.45 (2H, t, J=7.5 Hz), 3.83 (2H, t, J=6.3 Hz), 7.36–7.47 (3H, m), 8.10 (1H, br s).

Mass spectrum: M+ =312

Anal.Calc'd for $C_{12}H_{10}F_6N_2O$ : C, 46.16; H, 3.73; N, 8.97.

Found : C, 46.24; H, 3.27; N, 8.75

EXAMPLE 33

1-(4'-bromo-3'-methylphenyl)-2H-tetrahydropyridazin-3-one (Formula II, $R_1$=4-bromo-3-methylphenyl; $R_2$=H)

The title compound was prepared according to the method of Scheme I as described for Example 1, except using 4-bromo-3-methylaniline instead of 3-aminobenzonitrile as $R_1$-$NH_2$.

mp 154° C.

$^1$H NMR(300 MHz, CDCl$_3$) 1.96 (2H, m), 2.37 (3H, s), 2.42 (2H, t, J=7.5 Hz), 3.68 (2H, t, J=6.8 Hz), 6.70 (1H, dd, J=8.7,3.3 Hz) 6.87 (1H, d, J=3.3 Hz), 7.41 (1H, d, J=8.7 Hz), 7.78 (1H, br s).

Mass spectrum: M+ =269

EXAMPLE 34

1-(4'-(2-diethylaminoethyl)carboxylphenyl)-2H-tetrahydropyridazin-3-one (Formula II, $R_1$=4-(2-diethylaminoethyl)-carboxylphenyl; $R_2$=H)

The title compound was prepared according to the method of Scheme I as described for Example 1, except using 4-(2-diethylaminoethyl) carboxylaniline instead of 3-aminobenzonitrile as $R_1$-$NH_2$.

mp 166° C.

$^1$H NMR(60 MHz, DMSOd$_6$) 1.0 (6H, t, J=7 Hz), 1.90–2.10 (2H, m), 2.35 (2H, t, J=7 Hz), 2.45 (2H, t, J=7 Hz), 2.50 (2H, t, J=7 Hz) 2.70 (4H, q, J=7 Hz), 3.70 (2H, t, J=7 Hz), 6.85–6.95 (2H, m), 7.25–7.35 (2H, m), 7.55 (1H, br s).

Mass spectrum: M+ =319

EXAMPLE 35

1-(3,4,5-trichlorophenyl)-2H-tetrahydropyridazin-3-one (Formula II, $R_1$ = 3,4,5-trichlorophenyl; $R_2$ = H)

The title compound was prepared according to the method of Scheme I as described for Example 1, except using 3,4,5-trichloroaniline instead of 3-aminobenzonitrile as $R_1$-$NH_2$.

mp 199° C.

$^1$H NMR(60 MHz, DMSOd$_6$) 1.85-1.95 (2H, m), 2.52 (2H, t, J=7 Hz), 3.68 (2H, t, J=7 Hz), 6.78 (2H, s), 7.50 (1H, br s).

Mass spectrum: M+ =279

EXAMPLE 36

1-(N-ethyl-3-dibenzopyrolyl)-2H-tetrahydropyridazin-3-one (Formula II, $R_1$ = N-ethyl-3-dibenzopyrolyl; $R_2$ = H)

The title compound was prepared according to the method of Scheme I as described for Example 1, except using N-ethyl-3-aminodibenzopyrole instead of 3-aminobenzonitrile as $R_1$-$NH_2$.

mp 182° C.

$^1$H NMR (60 MHz, DMSOd$_6$) 1.22 (3H, t, J=7 Hz), 1.85-1.95 (2H, m), 2.47 (2H, t, J=7 Hz), 3.75 (2H, t, J=7 Hz), 4.30 (2H, q, J=7 Hz), 6.87-7.00 (2H, m), 7.05-7.55 (5H, m), 7.60 (1H, br s).

Mass spectrum: M+ =293

The following compounds presented in Table 1 may be prepared using the methods according to Scheme I in an analogous manner as Example 1.

TABLE 1
Formula II Compounds 1-(3-cyano-4-phenoxyphenyl)-2H-tetrahydropyridazin-3-one
(Formula II, $R_1$ = 3-cyano-4-phenoxyphenyl, $R_2$ = H)
1-(3,5-dicyanophenyl)-2H-tetrahydropyridazin-3-one
Formula II, $R_1$ = 3,5-dicyanophenyl, $R_2$ = H
1-(3-cyano-5-ethylphenyl)-2H-tetrahydropyridazin-3-one
Formula II, $R_1$ = 3-cyano-5-ethylphenyl, $R_2$ = H
1-(3-cyano-5-isobutylphenyl)-2H-tetrahydropyridazin-3-one
Formula II, $R_1$ = 3-cyano-5-isobutylphenyl, $R_2$ = H
1-(3-cyano-5-dodecylphenyl)-2H-tetrahydropyridazin-3-one
Formula II, $R_1$ = 3-cyano-5-dodecylphenyl, $R_2$ = H
1-(3-cyano-5-chlorophenyl)-2H-tetrahydropyridazin-3-one
Formula II, $R_1$ = 3-cyano-5-chlorophenyl, $R_2$ = H
1-(3-cyano-5-fluorophenyl)-2H-tetrahydropyridazin-3-one
Formula II, $R_1$ = 3-cyano-5-fluorophenyl, $R_2$ = H
1-(3-methylmercaptophenyl)-2H-tetrahydropyridazin-3-one
Formula II, $R_1$ = 3-methylmercaptophenyl, $R_2$ = H
1-(4-benzylphenyl)-2H-tetrahydropyridazin-3-one
Formula II, $R_1$ = 4-benzylphenyl, $R_2$ = H 1-(2-(7-bromofluorenyl))-2H-tetrahydropyridazin-3-one

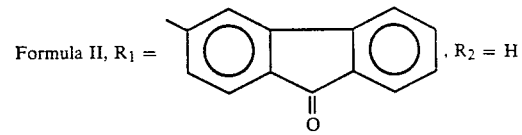

Formula II, $R_1$ = (structure shown), $R_2$ = H 1-(6-(3,4-benzocoumarinyl))-2H-tetrahydropyridazin-3-one

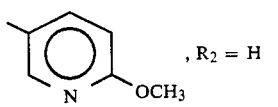

Formula II, $R_1$ = (structure shown), $R_2$ = H 1-(3-(9-fluorenonyl))-2H-tetrahydropyridazin-3-one

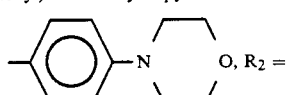

Formula II, $R_1$ = (structure shown), $R_2$ = H 1-(5-(2-methoxypyridyl))-2H-tetrahydropyridazin-3-one

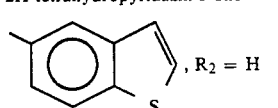

Formula II, $R_1$ = (structure shown), $R_2$ = H 1-(4-morpholinophenyl)-2H-tetrahydropyridazin-3-one

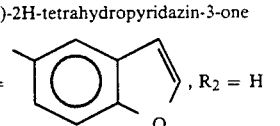

Formula II, $R_1$ = (structure shown), $R_2$ = H 1-(5-thianaphthyl)-2H-tetrahydropyridazin-3-one

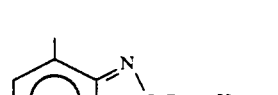

Formula II, $R_1$ = (structure shown), $R_2$ = H 1-(5-benzofuranyl)-2H-tetrahydropyridazin-3-one

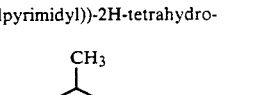

Formula II, $R_1$ = (structure shown), $R_2$ = H 1-(4-(2,1,3-benzothiadiazole))-2H-tetrahydropyridazin-3-one

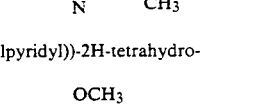

Formula II, $R_1$ = (structure shown), $R_2$ = H 1-(2-(4,6-dimethylpyrimidyl))-2H-tetrahydropyridazin-3-one

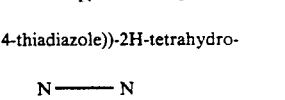

Formula II, $R_1$ = (structure shown), $R_2$ = H 1-(2-(4,6-dimethylpyridyl))-2H-tetrahydropyridazin-3-one

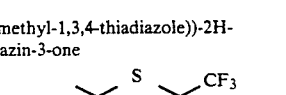

Formula II, $R_1$ = (structure shown), $R_2$ = H 1-(2-(5-ethyl-1,3,4-thiadiazole))-2H-tetrahydropyridazin-3-one Formula II, $R_1$ = (structure shown), $R_2$ = H 1-(2-(5-trifluoromethyl-1,3,4-thiadiazole))-2H-tetrahydropyridazin-3-one Formula II, $R_1$ = $R_1$ = (structure shown), $R_2$ = H

EXAMPLE 37

1-(3'-cyanophenyl)-4-methyl-2H-tetrahydropyridazin-3-one

Formula II, $R_1$ = 3'-cyanophenyl; $R_2$ = 4-methyl

The title compound can be prepared according to Scheme I in an analogous manner using the methods described for Example 1, substituting ethyl 4-bromo-2-methyl-butyrate for ethyl 4-bromobutyrate.

mp 147° C.

$^1$H NMR(300 MHz, CDCl$_3$) 1.17 (3H, d), 1.66 (1H, m), 2.37 (2H, ml), 3.64 (1H, m), 3.90 (1H, m), 7.18–7.25 (3H, m), 7.35–7.43 (1H, m), 7.67 (1H, br s).

Mass spectrum: M+ = 215

Anal.Calc'd. for $C_{12}H_{13}N_3O$ : C, 66.96; H, 6.09; N, 19.52.

Found : C, 67.17; H, 6.17; N, 18.83

EXAMPLE 38

1-phenyl-4-butyl-2H-tetrahydropyridazin-3-one

Formula II, $R_1$ = phenyl; $R_2$, = 4-butyl.

The title compound can be prepared in a manner analogous to Example 1, substituting ethyl-4-bromo-2-butyl-butyrate for ethyl-4-bromo-2-butyl-butyrate for ethyl-4-bromobutyrate, and aniline for 3-aminobenzonitrile.

Mass spectrum: M+ = 232

EXAMPLE 39

1-phenyl-4-benzyl-2H-tetrahydropyridazin-3-one

Formula II, $R_1$ = phenyl; $R_2$, = 4-benzyl.

The title compound can be prepared in a manner analogous to Example 1, substituting ethyl 4-bromo-2-benzyl-butyrate for ethyl-4-bromobutyrate and aniline for 3-aminobenzonitrile.

$^1$H NMR(300 MHz, CDCl$_3$) 1.65 (1H, m), 1.88 (1H, m), 2.70 (2H, m), 3.30 (1H, m), 3.65 (2H, m), 6.95 (2H), 7.25 (9H).

Mass spectrum: M+ = 266

EXAMPLE 40

1-phenyl-5-butyl-2H-tetrahydropyridazin-3-one

Formula II, $R_1$ = phenyl; $R_2$, = 5-butyl.

The title compound can be prepared in a manner analogous to Example 1, substituting ethyl 3-butyl-4-bromobutyrate for ethyl-4-bromobutyrate and aniline for 3-aminobenzonitrile.

Mass spectrum: M+ = 232

EXAMPLE 41

1-(4'-phenoxyphenyl)-4-methyl-2H-tetrahydropyridazin-3-one

Formula II, $R_1$ = 4'-phenoxyphenyl; $R_2$ = 4-methyl.

The title compound can be prepared in a manner analogous to Example 1, substituting 4-phenoxyaniline instead of 3-aminobenzonitrile and ethyl-2-methyl-4-bromobutyrate for ethyl-4-bromobutyrate.

mp 128° C.

$^1$H NMR(300 MHz, CDCl$_3$) 1.21 (3H, d), 1.56–1.70 (1H, m), 2.16–2.29 (1H, m), 2.41–2.56 (1H, m), 3.55–3.67 (1H, m), 3.74–3.85 (1H, m), 6.93–7.11 (7H, m), 7.28–7.40 (3H, m).

Mass spectrum: M+ = 282

The following compounds shown in Table 2 may be prepared according to the method of Scheme I in an analogous manner as Example 1, substituting the appropriately substituted ethyl 4-bromobutyrate and primary amine $R_1$-NH$_2$ for ethyl 4-bromobutyrate and 3-aminobenzonitrile respectively.

TABLE 2

Formula II Compounds 1-(3'-cyanophenyl)-4-ethyl-2H-tetrahydropyridazin-3-one
Formula II, $R_1$ = 3-cyanophenyl, $R_2$ = 4-ethyl
1-(3'-cyanophenyl)-4-isobutyl-2H-tetrahydropyridazin-3-one
Formula II, $R_1$ = 3-cyanophenyl, $R_2$ = 4-isobutyl
1-(3'-cyanophenyl)-4-butyl-2H-tetrahydropyridazin-3-one
Formula II, $R_1$ = 3-cyanophenyl, $R_2$ = 4-butyl
1-(3'-cyanophenyl)-4-benzyl-2H-tetrahydropyridazin-3-one
Formula II, $R_1$ = 3-cyanophenyl, $R_2$ = 4-benzyl
1-(3'-cyanophenyl)-4-phenyl-2H-tetrahydropyridazin-3-one
Formula II, $R_1$ = 3-cyanophenyl, $R_2$ = 4-phenyl
1-(3'-cyanophenyl)-4-methoxy-2H-tetrahydropyridazin-3-one
Formula II, $R_1$ = 3-cyanophenyl, $R_2$ = 4-methoxy
1-(3'-cyanophenyl)-4,5-dimethyl-2H-tetrahydropyridazin-3-one
Formula II, $R_1$ = 3-cyanophenyl, $R_2$ = 4,5-dimethyl
1-(3'-cyanophenyl)-4-(3-oxobutyl)-2H-tetrahydropyridazin-3-one
Formula II, $R_1$ = 3-cyanophenyl, $R_2$ = oxobutyl
1-(3'-cyanophenyl)-4-(3-hydroxybutyl)-2H-tetrahydropyridazin-3-one
Formula II, $R_1$ = 3-cyanophenyl, $R_2$ = 3-hydroxybutyl
1-(3'-cyanophenyl)-4-(2-diethylaminoethyl)-2H-tetrahydropyridazin-3-one
Formula II, $R_1$ = 3-cyanophenyl, $R_2$ = 2-diethylaminoethyl
1-(3'-cyanophenyl)-5-thiophenyl-2H-tetrahydropyridazin-3-one
Formula II, $R_1$ = 3-cyanophenyl, $R_2$ = thiophenyl
1-(3'-cyanophenyl)-5-thioethyl-2H-tetrahydropyridazin-3-one
Formula II, $R_1$ = 3-cyanophenyl, $R_2$ = thioethyl
1-(3'-cyanophenyl)-5-cyano-2H-tetrahydropyridazin-3-one
Formula II, $R_1$ = 3-cyanophenyl, $R_2$ = cyano
1-(3'-cyanophenyl)-5-dimethylamino-2H-tetrahydropyridazin-3-one
Formula II, $R_1$ = 3-cyanophenyl, $R_2$ = dimethylamino
1-(3'-cyanophenyl)-4,5-dihydroxy-2H-tetrahydropyridazin-3-one
Formula II, $R_1$ = 3-cyanophenyl, $R_2$ = 4,5-dihydroxy
1-phenyl-4-dodecyl-2H-tetrahydropyridazin-3-one
Formula II, $R_1$ = phenyl, $R_2$ = dodecyl
1-phenyl-5-phenoxy-2H-tetrahydropyridazin-3-one
Formula II, $R_1$ = phenyl, $R_2$ = 5-phenoxy
1-phenyl-4-butoxy-2H-tetrahydropyridazin-3-one
Formula II, $R_1$ = phenyl, $R_2$ = 4-butoxy b) Scheme II Certain pyridazinone compounds of this invention (e.g. the compounds of Examples 42–44) are preferably made according to Scheme II below. Reaction of a hydrazine (6) or a hydrazine salt with acetic anhydride in the presence of an appropriate base yields the corresponding acetyl anhydride (7). Condensation of (7) with an appropriately substituted ethylbromobutyrate (8) using diisopropylethylamine produces the disubstituted hydrazine (9). The hydrazine (9) is treated with a suitable base to effect intramolecular cyclization to the pyridazinone structure Formula II.

Scheme II

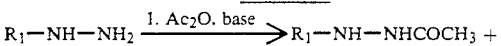

(6)    (7)

-continued

Scheme II

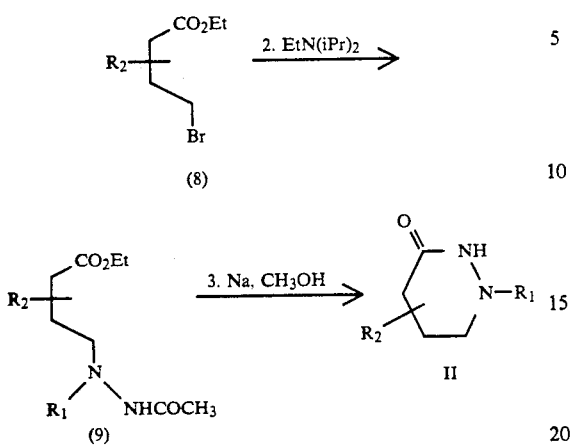

Further details of this scheme are provided in the following examples.

EXAMPLE 42

3-methylphenyl-2H-tetrahydropyridazin-3-one

Formula II, $R_1$=3-methylphenyl; $R_2$=H a) Acetyl 3-methylphenylhydrazide

Meta-tolylhydrazine hydrochloride salt (20 g, 0.13 mole) was dissolved in 1N NaOH (250 mL) and tetrahydrofuran (60 mL). With stirring, acetic anhydride (13 g, 0.13 mL) was added dropwise, and after stirring for 30 min the mixture was extracted with ether (3×100 mL). The combined ether extract was evaporated to afford a solid residue.

Recrystallization from a mixture of pentane and dichloromethane (1:1) gave the hydrazide (18.0 g), mp 101°–103° C.

b) Ethyl 4-(2-(acetyl 3-methylphenyl hydrazine)) butyrate

A mixture of hydrazide from part a (17.0 g, 0.1 mole), diisopropylethylamine (14.2 g, 0.11 mole) and ethyl 4-bromobutyrate (21.5 g, 0.11 mole) in toluene (100 mL) was refluxed under nitrogen for three days. The mixture was allowed to cool after which water (75 mL) and dichloromethane:ether (1:1, 100 mL) was added. The organic layer was separated, washed with water (65 mL), dried over MgSO$_4$, filtered and evaporated to give a residue (34.4 g).

c) 3-Methylphenyl-2H-tetrahydropyridazin-3-one.

The residue from part b (34.4 g) was dissolved in dry ethanol (100 mL) and with stirring under nitrogen, sodium (2.3 g, 0.1 mole) was added in small portions and the mixture was refluxed for 15 h. The mixture was allowed to cool and water (60 mL) was added. The mixture was concentrated in vacuo and the residue was partitioned in a mixture of water (50 mL) and dichloromethane (100 mL). The organic extract was dried over MgSO$_4$, filtered and evaporated to give a solid residue (18.6 g). Recrystallization from benzene gave the desired product (4.8 g, 25%), mp 114°–115° C. NMR (300 MHz, CDCl$_3$) 1.95(2 H, m), 2.34 (3 H, s), 2.43 (2H, t, J=7.5 Hz), 3.70 (2 H, t, J—7.5 Hz), 6.75–6.85 (3 H, m), 7.19 (1 H, m), 7.42 (1 H, br s).

EXAMPLE 43

1-(2'-methylphenyl)-2H-tetrahydropyridazin-3-one

Formula II, $R_1$=2-methylphenyl; $R_2$, Z=H

The title compound was prepared according to Scheme II in a manner analogous to Example 42 except ortho-tolylhydrazine hydrochloride salt was used instead of the meta-analog.

mp 169° C.

$^1$H NMR (300 MHz, CDCl$_3$) 1.85 (2H, m), 2.32 (3H, s), 2.61 (2H, t, J=7 Hz), 3.38 (2H, m), 7.0–7.2 (5H, m)

Mass spectrum: M+=190

EXAMPLE 44

1-(4'-methylphenyl)-2H-tetrahydropyridazin-3-one

Formula II, $R_1$=4-methylphenyl; $R_2$, Z=H

The title compound was prepared according to Scheme II in a manner analogous to Example 42 except para-tolylhydrazine hydrochloride salt was used instead of the meta-analog.

mp 131° C.

$^1$H NMR (300 MHz, CDCl$_3$) 1.93 (2H, m), 2.30 (3H, s), 2.43 (2H, t, J=7 Hz), 3.68 (2H, t, J=7 Hz), 6.92 (2H, m), 7.10 (2H, m), 7.55 (1H, br s).

Mass spectrum: M+=190

EXAMPLE 45

1-(2'-chlorophenyl)-2H-tetrahydropyridazin-3-one

Formula II, $R_1$=2-chlorophenyl; $R_2$=H)

The title compound was prepared according to Scheme II in a manner analogous to Example 42 except ortho-chlorophenylhydrazine hydrochloride salt was used instead of the meta-tolylhydrazine hydrochloride salt.

mp 191° C.

$^1$H NMR (300 MHz, CDCl$_3$) 1.85 (2H, m), 2.60 (2H, t, J=7 Hz), 3.65 (2H, m), 7.08 (1H, m), 7.23 (2H, m), 7.38 (1H, m), 8.28 (1H, br s).

Mass spectrum: M+=210

EXAMPLE 46

1-(3'-chlorophenyl)-2H-tetrahydropyridazin-3-one

Formula II, $R_1$=3-chlorophenyl; $R_2$=H

The title compound was prepared according to Scheme II in a manner analogous to Example 42 except meta-chlorophenylhydrazine hydrochloride salt was used instead of the meta-tolylhydrazine hydrochloride salt.

mp 114° C.

$^1$H NMR (300 MHz, CDCl$_3$) 2.02 (2H, m), 2.42 (2H, t, J=7 Hz), 3.70 (2H, t, J=7 Hz), 6.90 (2H, m), 7.0 (1H, t, J=2 Hz), 7.25 (1H, t, J=7 Hz), 7.65 (1H, br s).

Mass spectrum: M+=210

EXAMPLE 47

1-(4'-chlorophenyl)-2H-tetrahydropyridazin-3-one

Formula II, $R_1$=4-chlorophenyl; $R_2$=H

The title compound was prepared according to Scheme II in a manner analogous to Example 42 except para-chlorophenylhydrazine hydrochloride salt was used instead of the meta-tolylhydrazine hydrochloride salt.

mp 138° C.

$^1$H NMR (300 MHz, CDCl$_3$) 1.98 (2H, m), 2.45 (2H, t, J=7 Hz), 3.70 (2H, t, J=7 Hz), 6.95 (2H, m), 7.27 (2H, m), 7.55 (1H, br s).

Mass spectrum: M+ =210

EXAMPLE 50

1-(3'-bromophenyl)-2H-tetrahydropyridazin-3-one

Formula II, R$_1$ = 3-bromophenyl; R$_2$=H

The title compound was prepared according to Scheme II in a manner analogous to Example 42 except meta-bromophenylhydrazine hydrochloride salt was used instead of the meta-tolylhydrazine hydrochloride salt.

mp 123° C.

$^1$H NMR (300 MHz, CDCl$_3$) 2.00 (2H, m), 2.42 (2H, t, J=7 Hz), 3.70 (2H, t, J=7 Hz), 6.93 (1H, m), 7.05–7.2 (3H, m), 7.54 (1H, br s).

Mass spectrum: M+ =256, 254

EXAMPLE 51

1-(2'-fluorophenyl)-2H-tetrahydropyridazin-3-one

Formula II, R$_1$ = 2-fluorophenyl; R$_2$=H

The title compound was prepared according to Scheme II in a manner analogous to Example 42 except ortho-fluorophenylhydrazine hydrochloride salt was used instead of the meta-tolylhydrazine hydrochloride salt.

$^1$H NMR (300 MHz, CDCl$_3$) 1.88 (2H, m), 2.55 (2H, t, J=7 Hz), 3.65 (2H, t, J=7 Hz), 7.05–7.15 (4H, m), 7.35 (1H, s).

Mass spectrum: M+ =194

EXAMPLE 52

1-(3'-fluorophenyl)-2H-tetrahydropyridazin-3-one

Formula II, R$_1$ = 3-fluorophenyl; R$_2$=H)

The title compound was prepared according to Scheme II in a manner analogous to Example 42 except meta-fluorophenylhydrazine hydrochloride salt was used instead of the meta-tolylhydrazine hydrochloride salt.

mp 131° C.

$^1$H NMR (300 MHz, CDCl$_3$) 2.00 (2H, m), 2.42 (2H, t, J=7 Hz), 3.72 (2H, t, J=7 Hz), 6.70 (3H, m), 7.25 (1H, m), 7.55 (1H, br s).

Mass spectrum: M+ =194

EXAMPLE 53

1-(4'-fluorophenyl)-2H-tetrahydropyridazin-3-one

Formula II, R$_1$ = 4-fluorophenyl; R$_2$=H

The title compound was prepared according to Scheme II in a manner analogous to Example 42 except para-fluorophenylhydrazine hydrochloride salt was used instead of the meta-tolylhydrazine hydrochloride salt.

mp 148° C.

$^1$H NMR (300 MHz, CDCl$_3$) 1.92 (2H, m), 2.45 (2H, t, J=7 Hz), 3.65 (2H, t, J=7 Hz), 7.0 (4H, m), 7.55 (1H, br s).

Mass spectrum: M+ =194

The methods of Scheme II can be applied to substituted ethyl bromobutyrates (8) as exemplified by the following example.

EXAMPLE 54

1-phenyl-5-methyl-2H-tetrahydropyridazin-3-one

Formula II, R1 = phenyl, R2 = 5-methyl

The title compound was prepared according to Scheme II, where part a describes the synthesis of a substituted bromobutyrate (8). Condensation of (8) with acetyl phenylhydrazide provided the corresponding intermediate (9) which was reduced by catalytic hydrogenation and then treated with base to effect cyclization to the pyridazinone structure II.

a) To a solution of ethyl 3-methyl-2-butenoate (26 g, 0.2 mole) in tetrachloromethane (200 mL) was added N-bromosuccinimide (0.2 mole) and benzoyl peroxide (0.1 g), and the mixture was heated at reflux under a nitrogen atmosphere for 3 hours. The mixture was allowed to cool to room temperature. Water (100 mL). was added, and the organic layer was separated, washed with aqueous saturated NaCl, dried over MgSO$_4$, filtered and evaporated to provide a residue (38 g).

b) The residue from part a (20 g, 0.1 mole) was added to a solution of acetyl phenylhydrazide (15 g, 0.1 mole), diisopropylethylamine (0.1 mole) in benzene (200 mL) and heated at reflux for 3 days. The mixture was allowed to cool to room temperature. Water (100 mL) was added, and the organic layer was separated, washed with aqueous saturated NaCl, dried over MgSO$_4$, filtered and evaporated to provide a solid residue, which was washed with ether (2×10 mL) to give a pale yellow solid (10 g).

c) A solution of intermediate from part b (5.4 g, 0.02 mole) in ethanol (100 mL) was stirred with PtO$_2$ (0.4 g) under a hydrogen atmosphere for 3 hours. The mixture was filtered and evaporated to provide a residue (5.5 g).

d) To a solution of sodium (0.025 mole) in ethanol (50 mL) was added the residue from part c (5.5 g) and the mixture was refluxed under nitrogen for 16 hours. The mixture was allowed to cool at room temperature, water (50 mL) was added, and 1N HCl was added to adjust the solution to pH 7. The mixture was concentrated by evaporating the ethanol and then extracted with dichloromethane (2×50 mL). The organic extract was dried over MgSO$_4$, filtered and evaporated to provide a residue. Purification by column chromatography (silica gel, 10% ethylacetate in dichloromethane) gave the desired product (1.1 g), mp 132.

$^1$H NMR (300 MHz, CDCl$_3$) 0.97 (3H, d, J=6.5 Hz), 2.08 (1H, dd, J=14,8 Hz), 2.27 (1H, m), 2.56 (1H, dd, J=15,7 Hz), 3.17 (1H, dd, J=12, 10 Hz), 3.89 (1H, dd, J=13, 5 Hz), 6.98 (3H, m), 7.29 (2H, m), 7.37 (1H, br s).

Mass spectrum: M+ =190

Scheme III

Certain pyridazinone compounds of this invention (e.g. those in Example 55–58) of Formula III can be prepared by Scheme III below. 1H, 2H-pentahydropyridazin-3-one (10) is prepared according to the procedure outlined in Gut, et al, Coll. Czech Chem. Commun. 1968 Vol. 33 p 2087. The pyridazinone (10) is condensed with an appropriate electrophylic unit R1 - X (11) (where X is a leaving group such as a halogen) in the presence of an appropriate base or catalyst to yield the pyridazinone III.

Scheme III (structure 10): piperidinone-like ring with C=O, NH, NH  +  R₁—X  —Base→  III

(10)     III

EXAMPLE 55

1-(2-benzoxazole)-2H-tetrahydropyridazin-3-one

Formula III, R₁=2-benzoxazole; R₂=H

To a stirred mixture of 1H,2H-pentahydropyridazin-3-one (549 mg, 5.48 mmol) and tetra-n-butylammonium bromide (catalytic amount) in tetrahydrofuran (0.5 mL) was added 2-chlorobenzoxazole (1.0 mL) and toluene (5 mL). Aqueous 20% sodium hydroxide (0.5 ml) was added dropwise to the mixture which was stirred at room temperature for four days. The organic layer was separated and evaporated to yield the desired product (217 mg), mp 141° C.

$^1$H NMR (300 MHz, CDCl₃) 2.21 (2H, m), 2.52 (2H, t, J=7.0 Hz), 4.01 (2H, t, J=7.0 Hz), 7.22 (1H, m), 7.30 (1H, m), 7.38 (1H, d, J=8.0 Hz), 7.58 (1H, d, 8.0 Hz), 8.6 (1H, br s).

Mass spectrum: M+ =217.0842

EXAMPLE 56

1-(2-pyrimidyl)-2H-tetrahydropyridazin-3-one

Formula III, R₁=2-pyrimidyl; R₂=H

A stirred mixture of 1H,2H-pentahydropyridazin-3-one (200 mg, 2.0 mmol) and 2-chloropyrimidine (110 mg, 0.96 mmol) was heated at 80° C. under nitrogen for 24 hours. The melt was allowed to cool to room temperature, and purification by column chromotography (silica gel, hexane-ethyl acetate gradient, 1:1 to 0.1:1) gave the desired product (20 mg), mp 132.

$^1$H NMR (300 MHz, CDCl₃) 2.08 (2H, m), 2.54 (2H, t, J=7.1 Hz), 4.07 (2H, t, J=6.7 Hz), 6.67 (1H, t, J=4.8 Hz), 8.39 (2H, d, J=4.8 Hz), 8.80 (1H, br s).

Mass spectrum: M+ =178

EXAMPLE 57

1-(2-pyridyl)-2H-tetrahydropyridazin-3-one

Formula III, R₁=2-pyridyl; R₂=H

The title compound was prepared according to Scheme III in a manner analogous to Example 56 except substituting 2-chloropyridine for 2-chloropyrimidine and heating at 100° C.

$^1$H NMR (300 MHz, CDCl₃) 2.10 (2H, m), 2.36 (2H, t, J=7.3 Hz), 4.01 (2H, t, J=6.6 Hz), 6.81 (1H, ddd, J=7.1, 4.9, 0.7 Hz), 6.92 (1H, dt, J=8.5, 0.7 Hz), 7.59 (1H, ddd, J=8.5, 7.1, 1.8 Hz), 7.72 (1H, br s), 8.24 (1H, ddd, J=4.9, 1.8, 0.7 Hz).

Mass spectrum: M+ =177

EXAMPLE 58

1-(2,4-dinitrophenyl)-2H-tetrahydropyridazin-3-one

Formula III R₁=2,4-dinitrophenyl; R₂, Z=H

The title compound was prepared according to Scheme III in a manner analogous to Example 56 except substituting 1-fluoro-2,4-dinitrobenzene for 2-chloropyrimidine and heating at 100° C.

mp 185° C. (dec)

$^1$H NMR (300 MHz, CDCl₃) 2.19 (2H, m), 2.44 (2H, t, J=7.2 Hz), 3.68 (2H, t, J=7.0 Hz), 7.39 (1H, d, J=9.2 Hz), 7.69 (1H, br s), 8.35 (1H, dd, J=9.2, 2.6 Hz), 8.72 (1H, d, J=2.6 Hz).

Mass spectrum: M+ =266

The following compounds may be prepared according to Scheme III, Formula III, in an analogous fashion as Example 56, heating 1H, 2H-pentahydropyridazin-3-one with the corresponding electrophile (R'-X) with or without an appropriate solvent and base catalysis, as summarized in Table 3.

TABLE 3

Formula III compounds 1-(2-benzothiazoyl)-2H-tetrahydropyridazin-3-one

Formula III, R₁ = (benzothiazol-2-yl)

1-(3,5-dinitropyridyl)-2H-tetrahydropyridazin-3-one

Formula III, R₁ = (3,5-dinitropyridin-2-yl, O₂N...NO₂)

1-(2,5-dimethylpyrazyl)-2H-tetrahydropyridazin-3-one

Formula III, R₁ = (2,5-dimethylpyrazin-3-yl, CH₃ substituents)

1-(1,3-dimethyluracyl)-2H-tetrahydropyridazin-3-one

Formula III, R₁ = (1,3-dimethyluracil-6-yl)

1-(5-nitrothiazolyl)-2H-tetrahydropyridazin-3-one

Formula III, R₁ = (5-nitrothiazol-2-yl)

1-(4-methylquinolinyl)-2H-tetrahydropyridazin-3-one

Formula III, R₁ = (4-methylquinolin-2-yl)

1-(4-methyl-5-nitropyridyl)-2H-tetrahydropyridazin-3-one

Formula III, R₁ = (methyl, NO₂-substituted phenyl/pyridyl)

1-(3-nitropyridyl)-2H-tetrahydropyridazin-3-one

Formula III, R₁ = (3-nitropyridin-2-yl, O₂N)

1-(2-quinolinyl)-2H-tetrahydropyridazin-3-one

TABLE 3-continued

Formula III compounds

Formula III, R₁ = [quinoline structure]

1-(1,3-dimethyl-2,6(1H, 3H)-purindionyl)-2H-tetrahydropyridazin-3-one

Formula III, R₁ = [dimethyl purindionyl structure]

d) Scheme IV

Certain pyridazinones of this invention (e.g. those of Examples 59-66) of the general Formula IV can be prepared by reaction Scheme IV. A pyridazinone (12) is made according to reaction Schemes I-III above with the appropriate "R1" substitution. The pyridazinone (12) is treated with two equivalents of a strong base such as tert-butyllithium or a combination of potassium hydride and tert-butyllithium, followed by condensation with an electrophile, R2-X (13) (for example when X is halogen, carbonyl, acylchloride and the like), yields the 4-substituted compounds of Formula IV.

Scheme IV

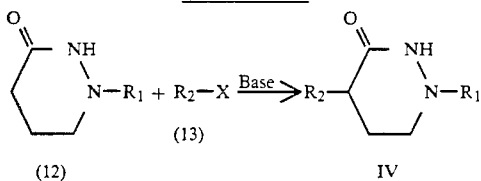

EXAMPLE 59

1-phenyl-4-(2-propenyl)-2H-tetrahydropyridazin-3-one

Formula IV, $R_1$=phenyl; $R_2$=allyl.

To a solution of 1-phenyl-2H-tetrahydropyridazin-3-one (1.76 g, 0.01 mole) in tetrahydrofuran (50 mL) at 5° C. under nitrogen and with stirring was added a suspension of KH (0.015 mole) in tetrahydrofuran (10 mL). Gas evolution (H₂) occurred. After 15 minutes the mixture was cooled to −78° C. and tert-butyllithium (7.5 mL of 1.5 M solution in pentane) was added dropwise. After stirring 5 minutes, CuCN (0.45 g, 0.005 mole) was added, and the mixture was allowed to warm to 5° C. for 20 minutes after which 3-bromopropene (0.011 mole) was added. The mixture was stirred for 30 minutes at 5° C. then 10% aqueous ammonium chloride (40 mL) and dichloromethane (50 mL) was added. The organic layer was dried over MgSO4, filtered and evaporated to give a residue. Purification by column chromatography (silica gel, 30% ether in dichloromethane) gave the desired product, mp 71° C.

¹H NMR (300 MHz, CDCl₃) 1.64 (1H, m), 2.15 (2H, m), 2.43 (1H, m), 2.59 (1H, m), 3.66 (1H, m), 3.81 (1H, m), 5.01 (2H, m), 5.73 (1H, m), 6.96 (3H, m), 7.3 (2H, m), 7.5 (1H, br s).

Mass spectrum: M+ =216

EXAMPLE 60

1-phenyl-4-(2-methyl-2-propenyl)-2H-tetrahydropyridazinone

Formula IV, $R_1$=phenyl; $R_2$=CH₂C(CH₃)=CH₂

The title compound was prepared according to Scheme IV in a manner analogous to Example 59 except 3-bromo-2-methylpropene was used instead of 3-bromopropene.

mp 108° C.

¹H NMR (300 MHz, CDCl₃) 1.57 (4H, m), 2.06 (2H, m), 2.55 (1H, m), 2.71 (1H, dd, J=15, 4.5 Hz), 3.77 (2H, m), 4.62 (1H, m), 4.75 (1H, m), 6.98 (3H, m), 7.21 (1H, br s), 7.30 (2H, m).

Mass spectrum: M+ =230

EXAMPLE 61

1-phenyl-4-ethoxymethyl-2H-tetrahydropyridazinone

Formula IV, $R_1$=phenyl; $R_2$=CH₂OCH₂CH₃.

The title compound was prepared according to Scheme IV in a manner analogous to Example 59 except chloromethylethylether was used instead of 3-bromopropene.

mp 83° C.

¹H NMR (300 MHz, CDCl₃) 1.14 (3H, t, J=7.5 Hz), 1.80 (1H, m), 2.12 (1H, m), 3.46 (2H, q, J=7.5 Hz), 3.74 (4H, m), 7.0 (3H, m), 7.28 (3H, m).

Mass spectrum: M+ =234

EXAMPLE 62

1-phenyl-4-benzyloxymethyl-2H-tetrahydropyridazinone

Formula IV, $R_1$=phenyl; $R_2$=CH₂OCH₂C₆H₅.

The title compound was prepared according to Scheme IV in a manner analogous to Example 59 except benzyl chloromethylether was used instead of 3-bromopropene.

mp 86° C.

¹H NMR (300 MHz, CDCl₃) 1.93 (1H, m), 2.13 (1H, m), 2.66 (1H, m), 3.75 (4H, m), 4.49 (2H, q), 6.97 (3H, m), 7.26 (7H, m), 7.6 (1H, br s).

Mass spectrum: M+ =296

EXAMPLE 63

1-phenyl-4-methylthiomethyl-2H-tetrahydropyridazinone

Formula IV, $R_1$=phenyl; $R_2$=CH₂SCH₃.

The title compound was prepared according to Scheme IV in a manner analogous to Example 59 except chloromethylmethylsulfide was used instead of 3-bromopropene.

mp 70° C.

¹H NMR (300 MHz, CDCl₃) 1.80 (1H, m), 2.08 (3H, s), 2.30 (1H, m), 2.62 (2H, m), 3.04 (1H, m), 3.77 (2H, m), 7.0 (3H, m), 7.28 (3H, m).

Mass spectrum: M+ =236

EXAMPLE 64

1-phenyl-4-phenylthiomethyl-2H-tetrahydropyridazinone

Formula IV, $R_1$=phenyl; $R_2$=CH₂SC₆H₅

The title compound was prepared according to Scheme IV in a manner analogous to Example 59 except chloromethylphenyl sulfide was used instead of 3-bromopropene.

$^1$H NMR (300 MHz, CDCl$_3$) 1.80 (1H, m), 2.4 (1H, m), 2.63 (1H, m), 2.90 (1H, dd, J=13, 3 Hz), 3.57 (1H, dd, J=13, 3 Hz), 3.67 (1H, m), 3.80 (1H, m), 6.97 (3H, m), 7.23 (8H, m).

Mass spectrum: M+ =298

EXAMPLE 65

1-phenyl-4-(3-methyl-1-oxo-but-2-enyl)-2H-tetrahydropyridazin-3-one

Formula IV, R$_1$=phenyl; R$_2$=COCHC(CH$_3$)$_2$

The title compound was prepared according to Scheme IV in a manner analogous to Example 59 except 3-methyl-but-2-enoyl chloride was used instead of 3-bromopropene.

mp 158° C.

$^1$H NMR (300 MHz, CDCl$_3$) 1.86 (3H, s), 2.07 (3H, s), 2.45 (2H, m), 3.71 (2H, m), 5.73 (1H, br s), 7.0 (5H, m), 7.3 (2H, m).

Mass spectrum: M+ =258

EXAMPLE 66

1-phenyl-4-(hydroxymethylphenyl)-2H-tetrahydropyridazin-3-one

Formula IV, R$_1$=phenyl; R$_2$=CHOHC$_6$H$_5$

The title compound was prepared according to Scheme IV in a manner analogous to Example 59 except benzaldehyde was used instead of 3-bromopropene.

$^1$H NMR (300 MHz, CDCl$_3$) 1.50 (2H, m), 2.68 (1H, q), 3.56 (1H, m), 3.71 (1H, m), 4.78 (1H, d), 5.00–5.50 (1H, br s), 6.92–7.05 (3H, m) 7.26–7.36 (7H, m), 7.72 (1H, s).

Mass spectrum: M+ =282

Anal.Calc'd. for C$_{17}$H$_{18}$N$_2$O$_2$ : C, 72.32; H, 6.43; N, 9.92.

Anal. Found : C, 71.90; H, 6.40; N, 9.59.

Following the method used for Example 59, substituting 3-bromopropene as R$_2$-X for an equivalent amount of an alternate electrophile R$_2$-X including halides, ketones, aldehydes, chloroformates, and acid chlorides, compounds of the Formula IV may be prepared as summarized in Table 4.

TABLE 4

Formula IV compounds 1-phenyl-4-ethyl-2H-tetrahydropyridazin-3-one
Formula IV, R$_1$ = phenyl, R$_2$ = —CH$_2$CH$_3$ 1-phenyl-4-hexyl-2H-tetrahydropyridazin-3-one
Formula IV, R$_1$ = phenyl, R$_2$ = —(CH$_2$)$_5$CH$_3$ 1-(3'-ethylphenyl)-4-methoxymethyl-2H-tetrahydropyridazin-3-one
Formula IV, R$_1$ = 3-ethylphenyl, R$_2$ = —CH$_2$OCH$_3$ 1-(3'-ethylphenyl)-4-(2-hydroxyethyl)-2H-tetrahydropyridazin-3-one
Formula IV, R$_1$ = 3-ethylphenyl, R$_2$ = —CH$_2$CH$_2$OH 1-(3'-ethylphenyl)-4-(2-diethylaminoethyl)-2H-tetrahydropyridazin-3-one
Formula IV, R$_1$ = 3-ethylphenyl, R$_2$ = —CH$_2$CH$_2$N(CH$_2$CH$_3$)$_2$ 1-(3'-ethylphenyl)-4-benzoyl-2H-tetrahydropyridazin-3-one
Formula IV, R$_1$ = 3-ethylphenyl, R$_2$ = —COC$_6$H$_5$ 1-(3'-ethylphenyl)-4-(1-hydroxyethyl)-2H-tetrahydropyridazin-3-one
Formula IV, R$_1$ = 3-ethylphenyl, R$_2$ = —CHOHCH$_3$

TABLE 4-continued

Formula IV compounds 1-(3'-ethylphenyl)-4-(1-hydroxybutyl)-2H-tetrahydropyridazin-3-one
Formula IV, R$_1$ = 4-phenoxyphenyl, R$_2$ = —CHOH(CH$_2$)$_2$CH$_3$ 1-(4'-phenoxyphenyl)-4-propionyl-2H-tetrahydropyridazin-3-one
Formula IV, R$_1$ = 4-phenoxyphenyl, R$_2$ = —COCH$_2$CH$_3$ 1-(2-pyridyl)-4-butyl-2H-tetrahydropyridazin-3-one
Formula IV, R$_1$ = 2-pyridyl, R$_2$ = —(CH$_2$)$_3$CH$_3$ 1-(3'-methylphenyl)-4-methylcyano-2H-tetrahydropyridazin-3-one
Formula IV, R$_1$ = 3-methylphenyl, R$_2$ = CH$_2$CN 1-(3'-methylphenyl)-4-ethoxycarbonyl-2H-tetrahydropyridazin-3-one
Formula IV, R$_1$ = 3-methylphenyl, R$_2$ = COOCH$_2$CH$_3$ 1-(4'-phenoxyphenyl)-4-(6-(2-oxotetrahydropyranyl))-2H-tetrahydropyridazin-3-one Formula IV, R$_1$ = 4'-phenoxyphenyl, R$_2$ = (2-oxotetrahydropyranyl group)

1-phenyl-4-(5-(2-oxotetrahydrofuranyl))-2H-tetrahydropyridazin-3-one

Formula IV, R$_1$ = phenyl, R$_2$ = (2-oxotetrahydrofuranyl group)

1-phenyl-4-(1-hydroxy-2-methoxyethyl)-2H-tetrahydropyridazin-3-one
Formula IV, R$_1$ = phenyl, R$_2$ = —CHOHCH$_2$OCH$_3$ 1-phenyl-4-(6-(2,2-dimethyldioxolanyl))-2H-tetrahydropyridazin-3-one Formula IV, R$_1$ = phenyl, R$_2$ = (2,2-dimethyldioxolanyl group)

II. Triazinone Synthesis a) Scheme V

Triazinone compounds of this invention of Formula V can be prepared according to general reaction Scheme V. Treatment of a substituted bromoethylamine salt 14, such as hydrobromide, with ethyl-chloroformate (or an alternate alkyl or arylchloroformate, ClCO$_2$R) in the presence of an appropriate base, such as triethylamine, provides the bromocarbamate intermediate 15. The bromocarbamate 15 is condensed With an amine 1 in the presence of an appropriate base to provide the carbamate intermediate 16. The intermediate 16 is then treated with sodium nitrite in the presence of an acid to yield the N-nitroso intermediate 17, which is reduced with zinc powder in the presence of acetic acid to provide the hydrazine intermediate 18. The hydrazine intermediate 18 is then cyclized with a suitable base such as ethylmagnesium bromide to provide triazinone compounds of Formula V.

Scheme V

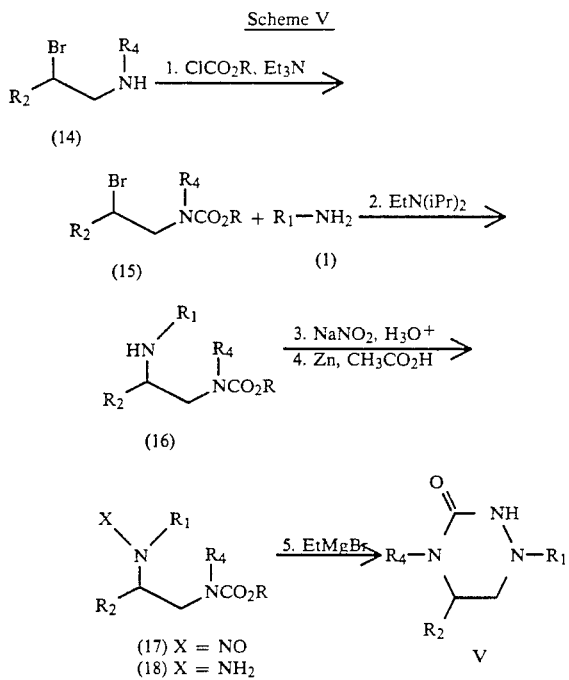

A preferred embodiment of this reaction scheme is illustrated by the following:

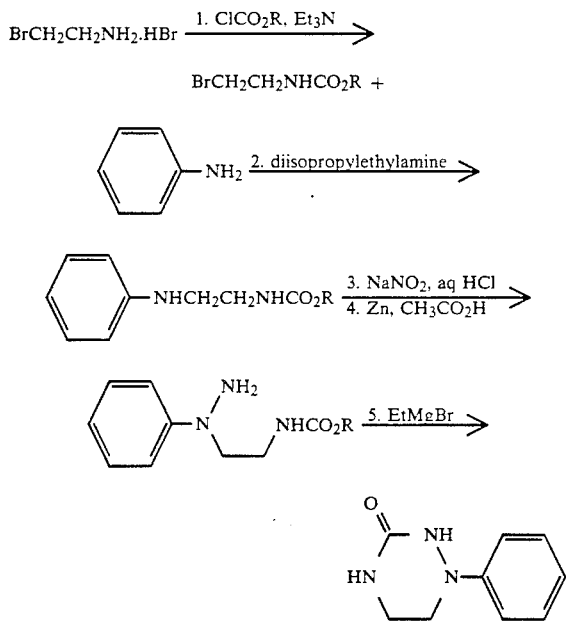

EXAMPLE 68

1-(phenyl)-2H,4H-tetrahydro-1,2,4-triazin-3-one

Formula V, $R_1$=phenyl, $R_2$=$R_4$=Z=H a) To a suspension of bromoethylamine hydrobromide salt (255 g, 1.25 mole) in dichloromethane (700 mL) was added triethylamine (252 g, 2.5 mole) at 0° C. under nitrogen while stirring. A solution of ethyl chloroformate (135.3 g, 1.25 mole) in dichloromethane (200 mL) was added to the mixture dropwise maintaining the temperature of the reaction between 0°-4° C. After the addition, the mixture was stirred for one hour. Water (500 mL) was added, and the organic layer was separated, washed with saturated aqueous NaCl, dried over MgSO$_4$, filtered and evaporated to give a residue (218 g) as a colorless oil.

b) A solution of aniline (83.7 g, 0.9 mole), bromocarbamate from part a (146.0 g, 0.92 mole) and diisopropylethylamine (90.3 g, 0.7 mole) in benzene (700 mL) was heated at reflux for 24 hours. The reaction mixture was allowed to cool to room temperature and water (500 mL) was then added, and the organic layer was separated, washed with saturated aqueous NaCl, dried over MgSO$_4$, filtered and evaporated to give a residue (118 g).

c) To the residue from part b (118 g, 0.57 mole) was added an ice cold solution of concentrated HCl (120 mL) dissolved in water (200 mL). With mechanical stirring and cooling at 0° C., a solution of sodium nitrite (41.4 g, 0.6 mole) in water (100 mL) was added dropwise. The mixture was stirred for two hours at 0° C. and a solid precipitate formed. The solid was collected by filtration, washed with water (2×100 mL), and dried in vacuo to provide a greenish yellow solid (115 g).

d) To a suspension of zinc dust (115 g, 0.48 mole) in water (350 mL) with mechanical stirring was added dropwise a solution of the product of part c (115 g) in acetic acid (230 mL). The temperature of the mixture was controlled between 5°-15° C. during the addition after which the cooling bath was removed and the mixture was stirred at 30° for 45 minutes. Dichloromethane (700 mL) was added and the mixture was filtered. The organic layer was separated and washed with 10% aqueous sodium carbonate (2×350 mL), saturated aqueous NaCl, dried over MgSO$_4$, filtered and evaporated to give a residue (93 g). e) The residue of part d (93 g, 0.42 mole) was dissolved in dichloromethane (350 mL) and cooled to −40° C. while stirring, a solution of ethylmagnesium bromide (225 mL, 2.0 M in tetrahydrofuran) was added dropwise maintaining the temperature below −30° C. After the addition, the mixture was allowed to warm to room temperature and then was heated at 40° C. for two days. Ice chips (500 g) were added with stirring, and the mixture was acidified with 3N HCl to pH 3. The phases were separated, and the aqueous phase was extracted with 5% methanol in dichloromethane (2×300 mL). The combined organic solutions were washed with saturated aqueous NaCl, dried over MgSO$_4$, filtered and evaporated to give a solid residue. The solid was suspended in 2% MeOH in dichloromethane (100 mL) and filtered to provide the desired product (28.7 g).

m.p. =219° C.

NMR (300 MHz, DMSO-d$_6$) 3.07-3.01 (2 H, m), 3.63 (2 H, t, J=5.5 Hz), 6.64 (1 H, br s), 6.87 (1 H, t, J=7.5 Hz), 7.03 (2 H, d, J=8 Hz), 7.27 (2 H, t, J=8 Hz), 8.42 (1 H, br s).

Mass spectrum: M$^+$=177

Analysis Calc'd for C$_9$H$_{11}$N$_3$O : C, 61.00; H, 6.26; N, 23.71.

Found: C, 60.83, H, 6.29; N, 23.72.

EXAMPLE 69

1-(2'-methylphenyl)-2H,4H-tetrahydro-1,2,4-triazin-3-one

Formula V, $R_1$=2-methylphenyl, $R_2$=$R_4$=H

The title compound was prepared according to Scheme V in an analogous manner as Example 68 except ortho-toluidine was used in part b instead of aniline. m.p.=>230° C.

NMR (300 MHz, DMSO-$d_6$), 2.23 (3 H, s), 2.99–2.93 (2 H, m), 3.22 (2 H, t, J=5 Hz), 6.78 (1 H, br s), 6.99 (1 H, dt, J=6 Hz, 1 Hz), 7.04 (1 H, d, J=7 Hz), 7.16 (2 H, d, J=7 Hz),8.19 (1 H, br s).

Mass spectrum: $M^+$=191

Analysis Calc'd for $C_{10}H_{13}N_3O$ : C, 62.8; H, 6.85; N, 21.97.

Found: C, 63.09; H, 6.95; N, 22.0

EXAMPLE 70

1-(3'-methylphenyl)-2H,4H-tetrahydro-1,2,4-triazin-3-one

Formula V, $R_1$=3-methylphenyl, $R_2$=$R_4$=H

The title compound was prepared according to Scheme V in an analogous manner as Example 68 except meta-toluidine was used in part b instead of aniline.

H NMR (300 MHz, DMSO-$d_6$). 2.26 (3 H, s), 3.05–2.98 (2 H, m), 3.61 (2 H, t, J=5 Hz), 6.63 (1 H, br s), 6.68 (1 H, d, J=7.0 Hz), 6.87–6.80 (2 H, m), 7.14 (1 H, t, J=7.5 Hz), 8.38 (1 H, br s).

m.p.=235°–236° C.

Mass spectrum: $M^+$=191

Analysis Calc'd for $C_{10}H_{13}N_3O$ : C, 62.8; H, 6.85; N, 21.97.

Found: C, 62.01; H, 6.91; N, 22.01

EXAMPLE 71

1-(4'-methylphenyl)-2H,4H-tetrahydro-1,2,4-triazin-3-one

Formula V, $R_1$=4-methylphenyl, $R_2$=$R_4$=H

The title compound was prepared according to Scheme V in an analogous manner as example 68 except para-toluidine was used in part b instead of aniline.

H NMR=(300 MHz, $CDCl_3$, $CD_3OD$), 2.22 (3 H, s), 3.14 (2 H, t, J=5 Hz), 3.52 (2 H, t, J=5 Hz), 6.87 (2 H, d, J=9 Hz), 7.03 (2 H, d, J=9 Hz), the two exchangeable NH protons are not observed under these conditions)

m.p.=218°–220° C.

Mass spectrum: $M^+$=191

Analysis Calc'd for $C_{10}H_{13}N_3O$ : C, 62.8; H, 6.85, N, 21.97.

Found: C, 59.5; H, 6.75; N, 21.09

EXAMPLE 72

1-(3'-cyanophenyl)-2H,4H-tetrahydro-1,2,4-triazin-3-one

Formula V, $R_1$=3-cyanophenyl, $R_2$=$R_4$=H

The title compound was prepared according to Scheme V in an analogous manner as Example 68 except 3-amino-benzonitrile was used in part b instead of aniline.

H NMR (300 MHz $CDCl_3$), 3.36–3.30 (2 H, m), 3.75 (2 H, t, J=6 Hz), 5.14 (1 H, br s), 6.51 (1 H, br s), 7.37–7.27 (3 H, m), 7.40 (1 H, q, J=7.5 Hz)

m.p.=>220° C.

Mass spectrum: $M^+$=202

EXAMPLE 73

1-(3'-bromophenyl)-2H,4H-tetrahydro-1,2,4-triazin-3-one

Formula V, $R_1$=3-bromophenyl, $R_2$=$R_4$=H

The title compound was prepared according to Scheme V in an analogous manner as Example 68, except 3-bromo-aniline was used in part b instead of aniline.

H NMR (300 MHz, DMSO-$d_6$) 3.03–3.09 (2 H, m), 3.67 (2 H, t, J=6 Hz), 6.77 (1 H, br s), 7.01–7.07 (2 H, m), 7.22 (2 H, t, J=7.5 Hz), 8.54 (1 H, br s)

m.p.=260°–262° C.

Mass spectrum: $M^+$=256

Analysis Calc'd for $C_9H_{10}BrN_3O$: C, 42.21; H,3.94; N, 16.41; Br 31.2.

Found: C, 41.48; H, 3.89; N, 16.11; Br, 31.18.

EXAMPLE 74

1-(3'-ethylphenyl)-2H,4H-tetrahydro-1,2,4-triazin-3-one

Formula V, $R_1$=3-ethylphenyl, $R_2$=$R_4$=H

The title compound was prepared according to Scheme V in an analogous manner as Example 68, except 3-ethylaniline was used in part b instead of aniline.

$^1$H NMR (300 MHz, DMSO-$d_6$), 1.16 (3 H, t, J=7.5 Hz), 2.56 (2 H, q, J=7 Hz), 3.01–3.07 (2 H, m), 3.62 (2 H, t, J=5 Hz), 6.63 (1 H, br s), 6.73 (1 H, d, J=7.5 Hz), 6.82–6.9 (2 H, m), 7.16 (1 H, t, J=7.5 Hz), 8.38 (1 H, br s)

m.p.=204°–205° C.

Mass spectrum: $M^+$=206

Analysis Calc'd for $C_{11}H_{15}N_3O$: C, 64.37; H, 7.37; N, 20.47.

Found: C, 63.54; H, 7.28; N, 20.33

EXAMPLE 75

1-(3'-methylthiophenyl)-2H,4H-tetrahydro-1,2,4-triazin-3-one

Formula V, $R_1$=3-methylthiophenyl, $R_2$=$R_4$=H

The title compound was prepared according to Scheme V in an analogous manner as Example 68, except 3-methylthioaniline was used instead of aniline.

$^1$H NMR (300 MHz, DMSO-$d_6$), 2.45 (3 H, s), 3.01–3.07 (2 H, m), 3.63 (2 H, t, J=6 Hz), 6.67 (1 H, br s), 6.76 (1 H, d, J=7 Hz), 6.82 (1 H, dd, J=9 Hz, 1.5 Hz), 6.9 (1 H, t, J=1.5 Hz), 7.21 (1 H, t, J=8 Hz), 8.56 (1 H, br s)

m.p.=179°–180° C.

Mass spectrum: $M^+$=224

Analysis Calc'd for $C_{10}H_{13}N_3OS$: C, 53.79; H, 5.87; N, 18.82.

Found: C, 52.69; H, 5.82; N, 18.52

EXAMPLE 76

1-(3'-trifluoromethylphenyl)-2H,4H-tetrahydro-1,2,4-triazin-3-one

Formula V, $R_1$=3-trifluoromethylphenyl $R_2$=$R_4$=H

The title compound was prepared according to Scheme V in an analogous manner as Example 68, except 3-trifluoromethylaniline was used in part b instead of aniline.

$^1$H NMR (300) MHz, DMSO-$d_6$, 3.04–3.11 (2 H, m), 3.76 (2 H, t, J=5.5 Hz), 6.79 (1 H, br s), 7.20 (1 H, d,

J=7 Hz), 7.36 (2 H, d, J=10 Hz), 7.5 (1 H, t, J=7.5 Hz), 8.63 (1 H,d, J=1.5 Hz)

m.p.=239°-241° C.

Mass spectrum: M+=246

Analysis Calc'd for $C_{10}H_{10}F_3N_3O$: C, 48.98; H, 4.11; N, 17.14.

Found: C, 48.84; H, 4.20; N, 17.04

EXAMPLE 77

1-(3'-methoxyaniline)-2H,4H-tetrahydro-1,2,4-triazin-3-one

Formula V, $R_1$=3-methoxyaniline, $R_2$=$R_4$=H

The title compound was prepared according to Scheme V in an analogous manner as Example 68, except 3-methoxyaniline was used in part b instead of aniline.

1H NMR (300 MHz, DMSO-d$_6$), 3.01-3.09 (2 H, m), 3.62 (2 H, t, J=6 Hz), 3.73 (3 H, s), 6.47 (1 H, dd, J=9, 2 Hz), 6.58 (1 H, t, J=2.5 Hz), 6.63 (1 H, dd, J=9, 1 Hz), 6.75 (1 H , br s), 7.16 (1 H, t, J=8 Hz), 8.46 (1 H, br s)

m.p.=183° C.

Mass spectrum: M+=208

Analysis Calc'd for $C_{10}H_{13}N_3O_2$: C, 57.96; H, 6.32; N, 20.28.

Found: C-57.56; H, 6.15; N, 20.18

EXAMPLE 78

1-(3'-chlorophenyl)-2H,4H, tetrahydro-1,2,4-triazin-3-one

Formula V, $R_1$=3-chlorophenyl, $R_2$=$R_4$=H

The title compound was prepared according to Scheme V in an analogous manner as Example 68, except 3-chloroaniline was used in part b instead of aniline.

1H NMR (300 MHz, DMSO-d$_6$), 3.03-3.09 (2 H, m), 3.67 (2 H, t, J=5 Hz), 6.72 (1H, br s), 6.9 (1 H, dd, J=9, 1.5 Hz), 7.01 (1 H, dd, J=9, 1.5 Hz), 7.07 (1 H, t , J=2.5 Hz), 7.27 (1 H, t, J=8 Hz), 8.53 (1 H, br s)

m.p.=244°-245° C.

Mass spectrum: M+=212

Analysis Calc'd for $C_9H_{10}ClN_3O$: C, 51.07; H, 4.76; N, 19.85.

Found: C-50.28; H, 4.79; N, 19.47

EXAMPLE 79

1-(3'-benzyloxyphenyl)-2H,4H-tetrahydro-1,2,4-triazin-3-one

Formula V, $R_1$=3-benzyloxyphenyl, $R_2$=$R_4$=H

The title compound was prepared according to Scheme V in an analogous manner as Example 68, except 3-benzyloxyaniline was used in part b instead of aniline.

1H NMR (300 MHz, DMSO-d$_6$), 3.01-3.07 (2 H, m), 3.62 (2 H, t, J=6 Hz), 5.06 (2H, s), 6.54 (1 H, dd, J=9, 1.5 Hz), 6.61-6.66 (2 H, m), 6.68 (1 H, t, J=2 Hz), 7.17 (1 H t J=8 Hz), 7.28-7.47 (5 H, m), 8.42 (1 H, d, J=1 Hz)

m.p.=169° C.

Mass spectrum: M+=284

EXAMPLE 80

1-(3',5'-dimethylphenyl)-2H,4H-tetrahydro-1,2,4-triazin-3-one

Formula V, $R_1$=3',5'- dimethylphenyl, $R_2$=$R_4$=H

The title compound was prepared according to Scheme V in an analogous manner as Example 68, except 3,5-dimethylaniline was used in part b instead of aniline.

1H NMR (300 MHz, DMSO-d$_6$), 2.20 (6 H, s), 2.99-3.06 (2 H, m), 3.58 (2 H, t, J=5 Hz), 6.51 (1 H, s), 6.6 (1 H, brs), 6.65 (2 H, s), 8.33 (1 H, d, 1.5 Hz)

m.p=255°-257° C.

Mass spectrum: M+=206

Analysis Calc'd for $C_{11}H_{15}N_3O$: C, 64.37; H, 7.37; N, 20.47.

Found: C-63.67; H, 7.47; N, 20.21

The following compounds shown in Table 5 may be prepared according to the method of Scheme V in an analogous manner as Example 68 except substituting the appropriate substituted analine (1).

TABLE 5

Phenyl substituted triazinones of Formula V,

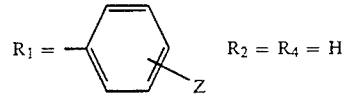

$R_2 = R_4 = H$

| Example | Z = |
|---|---|
| a | meta-2-furanyl |
| b | para-2-furanyl |
| c | meta-3-furanyl |
| d | meta-2-thiophenyl |
| e | para-2-thiophenyl |
| f | meta-3-thiophenyl |
| g | meta-2-thiazolyl |
| h | meta-2-oxazolyl |
| i | meta-2-benzothiophenyl |
| j | meta-2-pyridinyl |
| k | meta-3-pyridinyl |
| k | meta-4-pyridinyl |
| l | meta-5-pyrimidinyl |
| k | meta-phenoxy |
| l | meta-COCH$_3$ |
| m | para-COCH$_2$CH$_2$CH$_3$ |
| n | meta-COCH$_2$CH$_2$CO$_2$H |
| o | meta-CH$_2$CH$_2$CH$_2$CO$_2$H |
| p | meta-CH$_2$CH$_2$CN |
| q | meta-CH$_2$CH$_2$CONH$_2$ |
| r | meta-CH$_2$OCH$_3$ |
| s | meta-CH$_2$CH$_2$OH |
| t | meta-CH$_2$CH$_2$OCH$_2$CH$_2$OCH$_3$ |
| u | meta-CH(CH$_3$)N(OH)COCH$_3$ |
| v | meta-CH(CH$_3$)N(OH)CONH$_2$ |
| w | meta-CH=CHCH(CH$_3$)N(OH)COCH$_3$ |
| x | meta-CH=CHCH(CH$_3$)N(OH)CONH$_2$ |
| y | meta-CH(CH$_3$)CO$_2$H |
| z | meta-CH(CH$_3$)NHCONH$_2$ |
| aa | meta-C(CH$_3$)=NOCH$_3$ |
| bb | meta-C(CH$_3$)=N—N(CH$_3$)$_2$ |
| cc | meta-C(CH$_3$)NHCO$_2$CH$_3$ |
| dd | meta-C(CH$_3$)NHCSNH$_2$ |
| ee | meta-CH$_2$CH$_2$CH$_2$NHC(=NH)NH$_2$ |
| ff | meta-CH$_2$CH$_2$CH$_2$NHC(=NCN)NH$_2$ |

| | Formula V compounds | | |
|---|---|---|---|
| example | $R_1$ | $R_2$ | $R_4$ |
| gg | phenyl | 5-methyl | H |
| hh | phenyl | 5-butyl | H |
| ii | phenyl | 5-benzyl | H |
| jj | phenyl | 5-isobutyl | H |
| kk | phenyl | phenyl | H |
| ll | phenyl | cyano | H |
| mm | phenyl | H | CH3 |

TABLE 5-continued

| | | | |
|---|---|---|---|
| nn | phenyl | H | benzyl |
| oo | 3-ethylphenyl | ethyl | H | b) Scheme VI

Triazinone compounds of this invention of Formula V can be prepared according to Scheme VI. Treatment of a substituted hydroxyamine 19 with ethylchloroformate (or an alternate alkyl or arylchloroformate, $ClCO_2R$) in the presence of an appropriate base such as potassium carbonate provides the hydroxycarbamate intermediate 20. Then 20 is oxidized to the corresponding aldehyde 21. The aldehyde intermediate 21 is subjected to reductive amination with the amine 1 to provide the intermediate 22. Nitrosation to the nitroso compound 23 is followed by reduction to the hydrazine intermediate 24 which is then cyclized by treatment with a base such as ethylmagnesium bromide to provide the substituted triazinone compounds of Formula V.

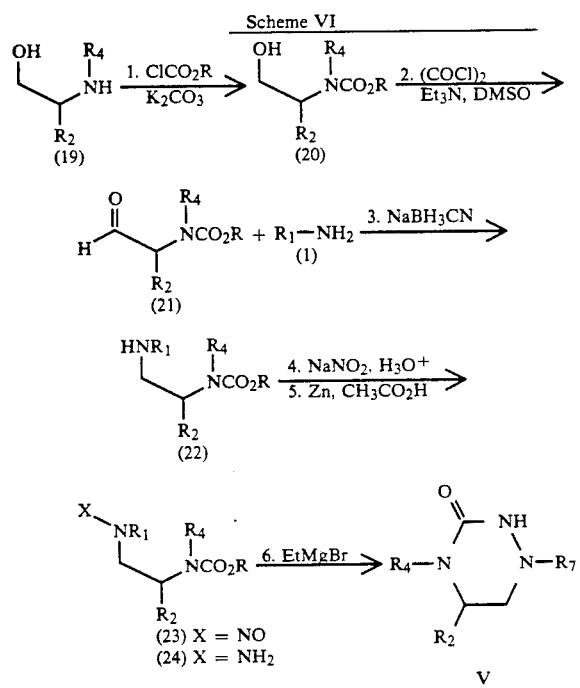

EXAMPLE 81

D,L-5-methyl-1-phenyl-2H,4H-tetrahydro-1,2,4-triazin-3-one

Formula V, $R_1$=phenyl, $R_2$=methyl; $R_4$=H a) A solution of D,L-2-amino-1-propanol (7.51 g, 0.10 mol) in dry acetonitrile (100 ml) containing solid anhydrous potassium carbonate (27.6 g, 0.20 mol) was vigorously stirred by a mechanical stirrer and chilled to −20° C. while a solution of methylchloroformate (9.45 g, 0.10 mol) in dry acetonitrile (20 mL) was introduced over a period of 30 min. The reaction mixture was stirred overnight at room temperature, filtered and the filtrate concentrated in vacuo to give the crude urethane, which was used directly without further purification.

b) To a stirred solution of oxalyl chloride (4.36 g, 34.0 mmol) in methylene chloride (30 mL) at −78° C. was added, dropwise, a solution of dimethylsulfoxide (5.28 g, 68.0 mmol) in methylene chloride (10 mL) over a 15 min. period and the mixture was stirred for another 15 min. at −78° C. To this mixture was added a solution of the urethane prepared in part a (3.01 g,22.6 mmol) in methylene chloride (30 mL) and the mixture was stirred for one hour at −78° C. Triethylamine (7.26 g, 72.0 mmol) was introduced and the reaction mixture was allowed to warm to room temperature, filtered and the filtrate concentrated in vacuo at 30° C. The residue was used directly in the next step.

c) The residue from part b was dissolved in methanol (100 mL), treated with aniline (2.05 g, 22.0 mmol) and the mixture adjusted to pH 5-6 with 10% ethanolic HCl. Sodium cyanoborohydride (1.57 g, 25 mmol) was added and the mixture stirred under a nitrogen atmosphere at room temperature. Enough additional 10% ethanolic HCl was added to keep the pH near 5-6. After stirring overnight at room temperature, the reaction mixture was rendered acidic with 10% ethanolic HCl and concentrated in vacuo at 30° C. The residue was taken up in methylene chloride (100 mL) and washed twice with 10-20 ml portions of aqueous potassium carbonate solution. The organic layer was dried over magnesium sulfate, concentrated and the residue was purified by chromatography (silica gel, methylene chloride ether) to provide 2.09 g of the anilino urethane.

d) A solution of the anilino urethane from part c (4.54 g, 0.021 mol) in a mixture of concentrated hydrochloric acid (4.5 mL) and water (20 mL) was chilled to −10° C. while a solution of sodium nitrite (1.66 g, 0.02 mol) in water (4 mL) was slowly added with mechanical stirring. The mixture became thick and difficult to stir so dimethoxyethane (15 mL) was added to facilitate the stirring. After another hour of stirring at 0° C., the mixture was extracted with benzene, the extracts dried over magnesium sulfate and concentrated to yield 5.05 g of the nitroso urethane.

e) A suspension of zinc dust (5.30 g, 0.08 mol) in water (15 mL) was magnetically stirred and cooled to 15° C. while a solution of the nitroso urethane from part d (5.05 g, 0.021 mol) in glacial acetic acid (12 mL) was introduced at a rate so as to maintain the internal temperature in the 15°-20° C. range. External cooling was removed and the reaction mixture was stirred at room temperature during which time the internal temperature spontaneously rose to 55° C. After one hour of additional stirring, the reaction was diluted with water (100 mL) and methylene chloride (100 mL) and treated with 15% sodium hydroxide solution to pH 6. The layers were decanted from the zinc residue and the organic layer separated and dried over magnesium sulfate. Removal of the solvent provided the crude hydrazino compound (4.28 g).

f) A solution of the hydrazino compound from part e (4.28 g, 0.019 mol) in methylene chloride (25 mL) was chilled to −25° C. while a 2M solution of ethylmagnesium bromide in tetrahydrofuran (12.5 ml,0.025 mol) was added dropwise with stirring and under an atmosphere of nitrogen. The reaction mixture was gently warmed (45° C.)for two days, treated with ice and water, adjusted to pH 3-4 with 6N hydrochloric acid and the layers separated. A portion of the product was isolated at this point by filtration while the remainder was isolated by evaporation of the methylene chloride layer. The combined solids were crystallized from ethanol to provide 1.15 g of the title compound.

m.p. 238°-240° C.

1H NMR (300 MHz, DMSO-d$_6$) 1.00 (3H, d, J=6.0 Hz), 2.89 (1H, dd, J=15, 10.5 Hz), 3.25 (1H, m), 4.03 (1H, dd, J=13.5, 4.5 Hz), 6.68 (1H, s), 6.86 (1H, t, J=7.5 Hz), 7.03 (2H, d, J=7.5 Hz), 7.25 (2H, t, J=7.5 Hz), 8.42 (1H, d, J=1.5 Hz).

Mass spectrum (M+H)$^+$=192

Anal Calc'd for C$_{10}$H$_{13}$N$_3$O: C, 62.81; H, 6.85; N, 21.97.

Anal.

Found: C, 63.27; H, 6.86; N, 22.11.

EXAMPLE 82

D,L-5-i-propyl-1-phenyl-2H,4H-tetrahydro-1,2,4-triazin-3-one

Formula V, R$_1$=phenyl, R$_2$=i-propyl, R$_4$=H

The title compound was prepared according to Scheme VI in an analogous manner as Example 81 except using D,L-2-amino-3-methyl-1-butanol instead of D,L-2-amino-1-propanol.

m.p.=181°–182° C.

1H NMR (300 MHz, DMSO-d$_6$) 0.85 (6H, d, J=7.5 Hz), 1.64 (1H, m), 2.96–3.12 (2H, m), 4.00 (1H, d, J=7.5 Hz), 6.56 (1H, br s), 6.86 (1H, t, J=7.5 Hz), 7.03 (2H, d, J=7.5 Hz), 7.26 (2H, t, J=7.5 Hz), 8.44 (1H, d, J=1.5 Hz).

Mass spectrum: (M+H)$^+$=220

Anal. Calc'd for C$_{12}$H$_{17}$N$_3$O: C, 65.73; H, 7.81; N, 19.16. Anal. Found: C, 65.86; H, 7.77; N, 18.42.

EXAMPLE 83

D,L-5-n-butyl-1-phenyl-2H,4H-tetrahydro-1,2,4-triazin-3-one

Formula V, R$_1$=phenyl, R$_2$=n-butyl, R$_4$=H

The title compound was prepared according to Scheme VI in an analogous manner as Example 81 except using D,L-2-amino-1-hexanol instead of D,L-2-amino-1-propanol.

m.p.=153°–155° C.

1H NMR (300 MHz, DMSO-d$_6$) 0.83 (3H, t, J=7.5 Hz), 1.10–1.50 (6H, m), 2.99 (1H, dd, J=15, 10.5 Hz), 3.09–3.19 (1H, m), 4.03 (1H, dd, J=13.5, 4.5 Hz), 6.62 (1H, s), 6.86 (1H, t, J=7.5 Hz), 7.04 (2H, d, J=7.5 Hz), 7.26 (2H, t, J=7.5 Hz), 8.42 (1H, d, J=1.5 Hz).

Mass spectrum: (M+H)$^+$=234

Anal calc'd for C$_{13}$H$_{19}$N$_3$O: C, 66.92; H, 8.21; N, 18.01.

Anal Found: C, 66.17; H, 8.05; N, 17.47.

EXAMPLE 84

D,L-5-methyl-1-(3-methylphenyl)-2H,4H-tetrahydro-1,2,4-triazin-3-one

Formula V, R$_1$=3-methylphenyl, R$_2$=methyl R$_4$=H

The title compound was prepared according to Scheme VI in an analogous manner as example 81 using 3-toluidine in part c instead of aniline.

m.p.=228°–229° C.

1H NMR (300 MHz, DMSO-d$_6$) 1.0 (3H, d, J=6 Hz), 2.26 (3H, s), 2.86 (1H, dd, J=13, 10 Hz), 3.21–3.31 (1H,m), 4.03 (1H, dd, J=13, 4.5 Hz), 6.57–6.62 (2H, m), 6.8–6.87 (2H, m), 7.13 (1H, t, J=7.5 Hz), 8.39 (1H, br s).

Mass spectrum: (M)$^+$=206

Anal calc'd for C$_{11}$H$_{15}$N$_3$O: C, 64.37; H, 7.37; N, 20.47.

Anal Found: C, 64.05; H, 7.43; N, 20.38.

EXAMPLE 85

D,L-5-methyl-1-(3-chlorophenyl)-2H,4H-tetrahydro-1,2,4-triazin-3-one

Formula V, R$_1$=3-chlorophenyl, R$_2$=methyl, R$_4$=H

The title compound was prepared according to Scheme VI in an analogous manner as example 81 using 3-chloroaniline in part c instead of aniline.

m.p.=246°–247° C.

1H NMR (300 MHz, DMSO-d$_6$) 1.02 (3H, d, J=7 Hz), 2.92 (1H, dd, J=13, 10 Hz), 3.22–3.33 (2H, m), 4.08 (1H, dd, J=13, 4 Hz), 6.77 (1H, br s), 6.88 (1H, d, J=7.5 Hz), 7.01 (1H, dd, J=7.5, 1.0 Hz), 7.27 (1H, t, J=7.5 Hz), 8.53 (1H, d, J=1 Hz).

Mass spectrum: (M)$^+$=226

Anal calc'd for C$_{11}$H$_{12}$ClN$_3$O: C, 53.22; H, 5.36; N, 18 62.

EXAMPLE 86

D,L-5-ethyl-1-phenyl-2H,4H-tetrahydro-1,2,4-triazin-3-one

Formula V, R$_1$=phenyl, R$_2$=ethyl, R$_4$=H

The title compound was prepared according to Scheme VI in an analogous manner as example 81 using D,L-2-amino-1-butanol in part a instead of D,L-2-amino-1-propanol.

m.p.=205° C.

1H NMR (300 MHz, DMSO-d$_6$) 0.82 (3H, t, J=7 Hz), 1.3–1.45 (2H, m), 2.99 (1H, dd, J=12, 10 Hz), 3.03–3.12 (2H, m), 4.04 (1H, dd, J=13, 3 Hz), 6.68 (1H, br s), 6.85 (1H, t, J=7.5 Hz), 7.03 (2H, d, J=7.5 Hz), 7.25 (2H, t, J=7.5 Hz), 8.39 (1H, br s).

Mass spectrum: (M)$^+$=206

Anal calc'd for C$_{11}$H$_{15}$N$_3$O: C, 64.37; H, 7.37; N, 20.47.

Anal Found: C, 64.05; H, 7.39; N, 20.46.

EXAMPLE 87

5,5-dimethyl-1-phenyl-2H,4H-tetrahydro-1,2,4-triazin-3-one

Formula V, R$_1$=phenyl, R$_2$=5,5-dimethyl, R$_4$=H

The title compound was prepared according to Scheme VI in an analogous manner as example 81 using 2-amino-2-methyl-1-propanol in part a instead of D,L-2-amino-1-propanol.

m.p.=273° C.

1H NMR (300 MHz, DMSO-d$_6$) 0.95 (6H, s), 3.58 (2H, s), 6.72 (1H, t, J=7.5 Hz), 6.81(1H, br s), 7.01 (2H, d, J=7.5 Hz), 7.2 (2H, t, J=7.5 Hz), 8.39 (1H, br s).

Mass spectrum: (M)$^+$=206

Anal calc'd for C$_{11}$H$_{15}$N$_3$O: C, 64.37; H, 7.37; N, 20.47.

Anal Found: C, 64.39; H, 7.34; N, 20.55.

c) Scheme VII

Triazinone compounds of Formula VI can be prepared by the method illustrated in scheme VII, which involves the reaction of a haloethyl isocyanate (25) with a substituted hydrazine (26) in an appropriate solvent to provide the semicarbazide intermediate (27). Substituted isocyanates (25), are prepared and manipulated by methods known to one skilled in the art. The intermediate (27) is subjected to conditions to effect intramolecular cyclization to the triazinone structure as in Formula VI.

As the intermediate (27) forms, it separates from the solution as a solid, and if desired, can be isolated by filtration, for example. The reaction will proceed at room temperature and it may be heated to the reflux temperature depending on the solvent employed. The hydrazine intermediate (27) is then cyclized in the presence of a polar aprotic solvent such as, dimethylformamide (DMF), dimethylsulfoxide, or hexamethylphosphoric triamide to form the triazinone VI. A preferred solvent is DMF. Cyclization is preferably conducted at elevated temperatures, from about 70° C. to about 100° C. Most preferred is the temperature range from about 70° C. to about 75° C. A preferred cyclization reaction which allows for increased yields at lower temperatures takes place in the presence of sodium iodide. The foregoing may be better understood from the following examples, which are presented for the purposes of illustration, and are not intended to limit the scope of the inventive concepts disclosed herein.

Scheme VII

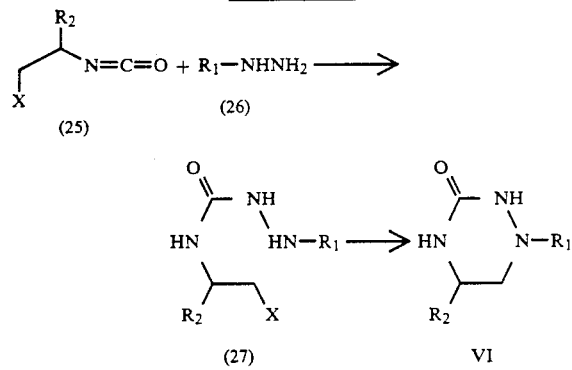

EXAMPLE 88

1-(3-fluorophenyl)-2H,4H-tetrahydro-1,2,4-triazin-3-one

Formula VI, $R_1$=3-flurophenyl, $R_2$=H a). To a stirred suspension of 3-fluorophenylhydrazine hydrochloride salt (4.06 g, 25 mmol) in dichloromethane (150 mL) was added triethylamine (2.5 g, 25 mmol). The mixture was stirred for 15 min. after which 2-chloroethylisocyanate (2.6 g, 25 mmol) was added dropwise. The mixture was stirred for 2 hours after which water was added (100 mL). The organic layer was separated, washed with aqueous saturated NaCl, dried over MgSO$_4$, filtered, and evaporated to give a solid (5.03 g).

b). The residue from part a (2.3 g, 10 mmol) was dissolved in dry dimethylformamide (20 mL) and NaI (2.99 g, 20 mmol) was added. The mixture was stirred at 75° C. for 48 h after which the mixture was allowed to cool to room temperature. Water (10 mL) was added and the iodine color was removed by adding a saturated solution of NaHSO$_3$. The pH of the mixture was adjusted to 8-9 by adding 2N NaOH. The mixture was evaporated to give an oil which was purified by chromatography (silica gel, 7% methanol in dichloromethane) to provide the title compound (0.8 g).

m.p.=194°-196° C.

1H NMR (300 MHz, DMSO-d$_6$) 2.17-2.23 (2H, m), 2.8 (2H, t, 6 Hz), 5.79 (1H, dt, J=8, 1.5 Hz), 5.85 (1H, br s), 5.94-6.04 (2H, m), 6.36-6.44 (1H, m), 7.76 (1H, br s).

Mass spectrum: $(M+H)^+$=196

Anal calc'd for C$_9$H$_{10}$FN$_3$O: C, 55.38; H, 5.16; N, 21.53.

Anal Found: C, 55.67; H, 5.12; N, 21.61.

EXAMPLE 89

1-(3-nitrophenyl)-2H,4H-tetrahydro-1,2,4-triazin-3-one

Formula VI, $R_1$=3-nitrophenyl, $R_2$=H

The title compound was prepared according to Scheme VII in an analogous manner as Example 88 using 3-nitrophenyl-hydrazine in part a instead of phenylhydrazine.

m.p.=205°-208° C.

1H NMR (300 MHz, DMSO-d$_6$) 3.06-3.14 (2H, m), 3.79 (2H, t, J=5 Hz), 6.82 (1H, br s), 7.49-7.59 (2H, m),7.68-7.74 (1H, m), 7.83 (1H, t, J=2 Hz), 8.73 (1H, br s).

Mass spectrum: $(M+NH_4)^+$=240

Anal calc'd for C$_9$H$_{10}$N$_4$O$_3$: C, 48.65; H, 4.54; N, 25.22.

Anal Found: C, 49.23; H, 4.76; N, 24.61.

EXAMPLE 90

1-(2-pyridyl)-2H,4H-tetrahydro-1,2,4-triazin-3-one

Formula VI, $R_1$=2-pyridyl, $R_2$=H

The title compound was prepared according to Scheme VII in an analogous manner as Example 88 using 2-pyridylhydrazine in part a instead of phenylhydrazine.

m.p.=174°-176° C.

1H NMR (300 MHz, DMSO-d$_6$) 3.06-3.13 (2H, m), 3.87 (2H, t, J=6 Hz), 6.77 (1H, br s), 6.80-6.85 (1H, m), 7.03 (1H, d, J=7.5 Hz), 7.64-7.7 (1H, m), 8.15-8.2 (1H, m), 8.63 (1H, br s).

Mass spectrum: $(M+H)^+$=179

Anal calc'd for C$_8$H$_{10}$N$_4$O: C, 53.92; H, 5.66; N, 31.44.

Anal Found: C, 53.49; H, 5.72; N, 30.80.

EXAMPLE 91

1-(2-benzothiazolyl)-2H,4H-tetrahydro-1,2,4-triazin-3-one

Formula VI, $R_1$=2-benzothiazolyl, $R_2$=H

The title compound was prepared according to Scheme VII in an analogous manner as Example 88 using 2-hydrazino-benzothiazole in part a instead of phenylhydrazine.

m.p.=249°-252° C.

1H NMR (300 MHz, DMSO-d$_6$) 3.31-3.36 (2H, m), 3.53-3.6 (2H, t, J=7 Hz), 7.09 (1H, dt, J=7.5 , 1 Hz),7.15 (1H, br s), 7.27 (1H, dt, J=7.5, 1 Hz), 7.45 (1 H, d, J=7.5 Hz) 7.75 (1H, d, J=7.5 Hz), 9.75 (1H, br s).

Mass spectrum: $(M+H)^+$=235

Anal calc'd for C$_{10}$H$_{10}$N$_4$OS: C, 51.27; H, 4.30; N, 23.92.

Anal Found: C, 51.19; H, 4.47; N, 23.53.

EXAMPLE 92

1-(3-quinolyl)-2H,4H-tetrahydro-1,2,4-triazin-3-one

Formula VI, $R_1$=3-quinolyl, $R_2$=H

The title compound was prepared according to Scheme VII in an analogous manner as Example 88 using 3-hydrazino-quinoline in part a instead of phenylhydrazine.

m.p.=184°-186° C.

1H NMR (300 MHz, DMSO-d6) 3.1-3.17 (2H, m), 3.83 (2H, t, J=5 Hz), 6.82 (1H, br s), 7.5-7.6 (2H, m), 7.73 (1H, d, J=3.0 Hz), 7.84-7.87 (1H, m), 7.91-7.96 (1H, m), 8.67 (1H, d, J=1.5 Hz), 9.87 (1H, d, J=3 Hz).

Mass spectrum: (M+H)+ =229

Anal calc'd for C12H12N4O: C, 63.18; H, 5.30; N, 24.55.

Anal Found: C, 62.64; H, 5.44; N, 24.32.

EXAMPLE 93

1-(2-benzoxazolyl)-2H,4H-tetrahydro-1,2,4-triazin-3-one

Formula VI, R1 = 2-benzoxazolyl, R2 = H

The title compound was prepared according to Scheme VII in an analogous manner as Example 88 using 2-hydrazino-benzoxazole in part a instead of phenylhydrazine.

m.p.=240°-241° C.

1H NMR (300 MHz, DMSO-d6) 3.28-3.34 (2H, m), 3.83 (2H, t, J=5 Hz), 7.08 (1H, br s), 7.16 (1H, dt, J=7.5, 1.5 Hz), 7.25 (1H, dt, J=7.5, 1.5 Hz), 7.45 (1H, d, J=7.5 Hz), 7.55 (1H, d, J=7.5 Hz), 9.05 (1H, br s).

Mass spectrum: (M+H)+ =219

Anal calc'd for C10H10N4O: C, 55.04; H, 4.62; N, 25.68.

Anal Found: C, 54.23; H, 4.49; N, 25.17.

d) Scheme VIII

A process for the preparation of triazinone compounds with substitution at the 5-position is outlined in Scheme VIII. Treatment of an appropriately substituted chloramine derivative (28, R2=CO2CH3) with phosgene or similar equivalent provides an isocyanate intermediate 29 which was not isolated but subsequently treated with an arylhydrazine, (of the formula R1N2H3) which in this example phenylhydrazine is shown to illustrate the process, and provides the intermediate semicarbazide 30. Intramolecular cyclization of 30 by heating in an appropriate solvent such as dimethylformamide (DMF) in the presence of NaI provides the triazinone 31. The carboxyester group at position 5 in the triazinone 31 can be in turn converted into various other derivatives such as a hydroxy group by reduction or an amide group by substitution reactions with an amine. Thus, 31 can serve as a useful intermediate to other 5-substituted triazinone compounds by one skilled in the art.

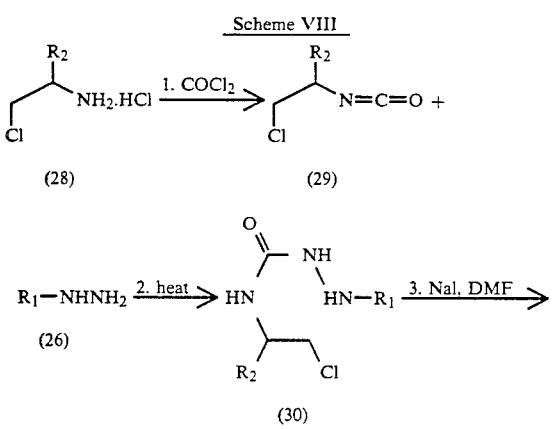

Scheme VIII

-continued
Scheme VIII

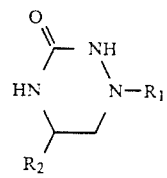

VI

EXAMPLE 94

D,L-5-carbomethoxy-1-phenyl-2H-tetrahydro-1,2,4-triazin-3-one

Formula VI, R1 = phenyl, R2 = 5-carbomethoxy a). D,L-2-Amino-3-chloropropionic acid methyl ester hydrochloride (28). The title compound was prepared in 85% yield from DL-serine methyl ester hydrochloride according to the method of Plattner, et al., Helv Chim Acta, 40, 1531 (1957).

m.p.126°-130° dec (lit. m.p. 134°-136°).

b). 4-[(1-carbomethoxy-2-chloro)ethyl]-1-phenyl-semicarbazide (30). A suspension of D,L-2-amino-3-chloropropionic acid methyl ester hydrochloride (26.8 g, 0.15 mol) in toluene (250 mL) was stirred at reflux temperature while a solution of phosgene in toluene (160 mL of a 1.93 M solution, 0.309 mol) was introduced dropwise in 40 mL portions at 30 minute intervals. The nearly clear, yellow-orange reaction mixture was heated at reflux for 30 minutes longer and then kept at room temperature overnight. The mixture was filtered to remove solids and the filtrate was concentrated in vacuo, to provide the crude isocyanate which was taken up in dry ether (250 mL) and added dropwise at room temperature under nitrogen to a stirred solution of phenylhydrazine (12.9 g, 0.12 mol) in dry ether (250 mL). The mixture was stirred overnight under a nitrogen atmosphere at room temperature, filtered and the filtrate washed three times with 1N HCl to remove any remaining phenyl hydrazine. After drying over magnesium sulfate, the ether layer provided, upon concentration, the title compound (31.7 g) which was of sufficient purity to be used directly without further purification.

c). D,L-5-carbomethoxy-1-phenyl-2H-tetrahydro-1,2,4-triazin-3-one (31). A solution of the previously described semicarbazide (31.7 g) in dry dimethylformamide (140 mL) was treated with sodium iodide (35.0 g, 0.23 mol) and the mixture was stirred for two days at 75°-80° C. under a nitrogen atmosphere. The mixture was allowed to cool, was treated with saturated aqueous sodium bisulfite (10 mL) and diluted with water (150 mL). Aqueous NaOH (6N) was added to adjust the solution to pH 7-8 and the mixture was filtered to isolate a portion of the crystalline title compound which was washed several times with water. The aqueous DMF filtrate was concentrated in vacuo at 50°-55° C. to remove most of the water and the residue was distilled at 50°-60° C. and 0.1 mm-Hg to remove most of the DMF. The residue was partitioned between water (100 mL) and ethyl acetate (200 mL). After drying over magnesium sulfate, the ethyl acetate layer was concentrated and the residue was triturated in dichloromethane (20 mL). The remaining portion of the title compound was collected by filtration and washed free of all color with portions of dichloromethane. The total yield was 4.65 g. Decomposition at 209°-212° C. with gas evolution.

1H NMR (300 MHz, DMSO-$d_6$) 3.40 (3 H, s), 3.77-3.90 (1H, m), 3.90-4.02 (2 H, m), 6.81-6.94 (2 H, m), 7.02 (2H,d,J=7.5 Hz),7.25 (2H, t, J=7.5 Hz), 8.66 (1 H, d, J=2.0 Hz).

Mass spectrum: (M+H)+ =236

Anal. Calc'd for $C_{11}H_{13}N_3O_3$: C, 56.16; H, 5.57; N, 17.86. Anal. found: C, 55.70; H, 5.58; N, 17.88.

The carboxy ester group at position - 5 on the triazinone ring can be converted to various other derivatives such as a hydroxy group by reduction or an amide group by a substitution reaction with an amine. Thus compounds of Formula VI may be useful intermediates to prepare other 5-subsituted triazinone compounds.

The following example illustrates the utility of Example 94 as an intermediate.

EXAMPLE 95

D,L-5-(1-hydroxy-1-methylethyl)-1-phenyl-2H,4H-tetrahydro-1,2,4-triazin-3-one.

Formula VI, $R_1$=phenyl, $R_2$=1-hydroxy-1-methylethyl

A suspension of the title compound of Example 94 (0.118 g, 0.5 mmol) in dry tetrahydrofuran (10 mL) was cooled to −20° C. and treated with a solution of methylmagnesium bromide (1.1 mL of a 2.9 M solution in ether, 3.2 mmol). The mixture was stirred for 1 h, allowed to warm to room temperature, and saturated aqueous NH4Cl (2.0 mL) was added. The mixture was adjusted to pH=2 with 3N HCl and the organic layer was separated and concentrated. The residue was purified by chromatography (silica gel, methanol-dichloromethane 1:20) to give the title compound (103 mg).

m.p.=224°-226° dec.

1H NMR (300 MHz, DMSO-$d_6$) 1.06 (6H, s), 2.94-3.13 (2H, m), 4.09 (1H, dd, J=4.5,13.5 Hz), 4.62 (1H, s), 5.98 (1H, br s), 6.87 (1H, t, J=7.5 Hz), 7.04 (2H, d, J=7.5 Hz), 7.28 (2H, t, J=7.5 Hz), 8.56 (1H, d, J=1.5 Hz).

Mass spectrum: (M+H)+ =236

Anal. Calc'd for $C_{12}H_{17}N_3O_2$: C, 61.26; H, 7.28; N, 17.86. Anal. found: C, 60.85; H, 7.27; N, 17.64.

The following compounds shown in Table 6 are prepared according to the method of Scheme VIII in an analogous manner as Example 94 except substituting the appropriate chloroamine derivative for 28 and the appropriate aryl or heteroaryl hydrazine for phenylhydrazine.

TABLE 6

| | Formula VI compounds | |
|---|---|---|
| Example | $R_1$ = | and $R_2$ = |
| a | meta-chlorophenyl | —CONH$_2$ |
| b | meta-methylphenyl | —CN |
| c | meta-chlorophenyl | —CH$_2$OCH$_2$CO$_2$H |
| d | meta-chlorophenyl | —CH$_2$OCH$_2$CH$_2$OH |
| e | meta-phenoxy | —CH$_2$OCH$_2$CH$_2$CH$_2$CO$_2$H |
| f | 4-pyridyl | —CH$_2$OCH$_2$CH$_2$OCH$_3$ |
| g | meta-chlorophenyl | —CON(OH)CH$_3$ |
| h | 4-pyridyl | —CH$_2$NHCH$_2$CO$_2$H |
| i | 2-pyridyl | —CH$_2$NHCH$_2$CO$_2$CH$_3$ |
| j | 3-pyridyl | —CH$_2$NHCH$_2$CO$_2$H |
| k | 5-pyrimidyl | —CH$_2$NHCO$_2$CH$_3$ |
| l | 4-pyridyl | —CH$_2$NHCONH$_2$ |
| m | meta-chlorophenyl | —COCH$_3$ |
| n | meta-chlorophenyl | —C=NOCH$_3$ |
| o | meta-methylphenyl | —CH$_2$OCH$_2$CH=CH$_2$ |
| p | meta-chlorophenyl | —CH$_2$OCH$_2$C≡CH |

TABLE 6-continued

| | Formula VI compounds | |
|---|---|---|
| Example | $R_1$ = | and $R_2$ = |
| q | 2-benzothiazole | —COCH$_2$CH$_2$CH$_2$CH$_3$ |
| r | 2-quinolyl | —CO$_2$CH$_3$ |
| s | 3-(2-furanyl)phenyl | —CO$_2$CH$_3$ |
| t | 3-(2-thiophenyl)phenyl | —CO$_2$CH$_3$ |
| u | 3-(4-pyridyl)phenyl | —CO$_2$CH$_3$ |
| v | 3-(5-pyrimidyl)phenyl | —CO$_2$CH$_3$ |
| w | 3-(3-pyridazinyl)phenyl | —CO$_2$CH$_3$ |
| v | 3-(2-benzothiophenyl)phenyl | —CO$_2$CH$_3$ |
| w | 3-(2-quinolinyl)phenyl | —CO$_2$CH$_3$ |
| x | 3-(2-thiazolyl)phenyl | —CO$_2$CH$_3$ |
| y | 3-(5-tetrazole)phenyl | —CO$_2$CH$_3$ | e) Scheme IX

Triazinone compounds of Formula VI substituted at the 5-position can be readily prepared as outlined in Scheme IX. The reaction of a substituted alkene (31) with iodine isocyanate provides an intermediate isocyanate (32) (the use of iodine isocyanate is a known method, Hassner, A.; Lorber, M. E.; Heathcock, C. J. Org. Chem. 1967, 32, 540.) which is not isolated but directly reacted with a substituted hydrazine (26) to provide the semicarbazide intermediate (33) which is subsequently cyclized to triazinone compounds of Formula VI as previously demonstrated.

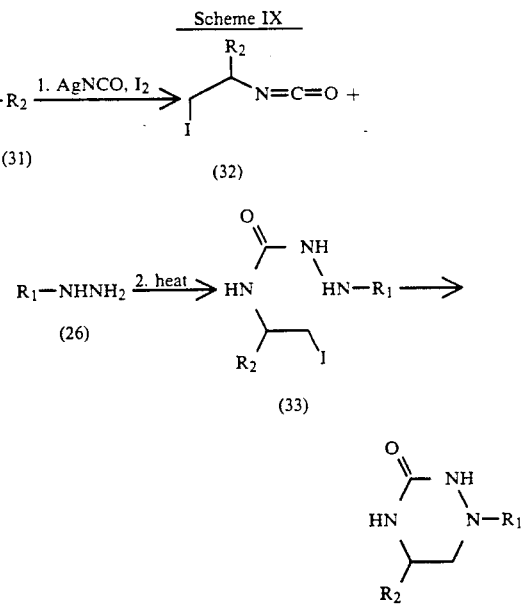

Scheme IX

EXAMPLE 96

5-(2-methoxyethoxymethyl)-1-phenyl-2H,4H-tetrahydro-1,2,4-triazin-3-one.

Formula VI, $R_1$=phenyl, $R_2$=2-methoxethoxy-methyl a). Iodine (2.54 g, 10 mmol) was dissolved in anhydrous ether (20mL) and treated with AgNCO (2 g, 13 mmol) at room temperature under nitrogen. The mixture was cooled to 0° C. and 3-(2-methoxyethoxy) propene (1.16 g, 10 mmol) was added over 30 min. The mixture was stirred at room temperature for 2 h, filtered through Celite. The filtrate solution was used directly in the next step.

b). The filtrate from part a was added dropwise to a stirred solution of phenylhydrazine (1.08 g, 10 mmol) in ether (50 mL) at room temperature. The mixture was concentrated to give a crude residue which was purified by chromatography (silica gel, dichloromethane/methanol, 19:1) to provide the iodosemicarbazide intermediate (1.6 g).

c). The iodosemicarbazide intermediate (1.05 g, 2.67 mmol) was dissolved in ethanol (10 mL) and heated to reflux for 5 hours. The solvent was evaporated and the residue was dissolved in dichloromethane (10 mL) and ether was added to induce crystallization to give the desired product (228 mg).

m.p.=118°–120° C.

1H NMR (300 MHz, DMSO-$d_6$) 3.35 (3H, s), 3.44–3.96 (9H, m), 5.42 (1H, m), 6.85 (2H, d, J=7.5 Hz), 6.92 (1H, t, J=7.5 Hz), 7.28 (2H, t, J=7.5 Hz), 8.50 (1H, s).

Mass spectrum: $(M+H)^+ = 266$

The following compounds shown in Table 7 may be prepared according to the method of Scheme IX in an analogous manner as Example 96 except substituting the appropriate olefin (31) and the appropriately substituted aryl or heteroaryl hydrazine (26).

TABLE 7

Formula VI compounds

| Example | $R_1$ = | $R_2$ = |
|---|---|---|
| a | meta-chlorophenyl | —$CH_2CH_2CH_2CH_2CO_2CH_3$ |
| b | meta-methylphenyl | —$CH_2CH_2CO_2H$ |
| c | 2-pyridyl | —$CH_2CH_2CH_2CH_2CO_2H$ |
| d | 4-pyridyl | —$CH_2CH_2CH_2OH$ |
| e | 3-(2-pyridyl)phenyl | —$CH_2CH_2CH_2CO_2CH_3$ |
| f | meta-chlorophenyl | —$CH_2CH_2CH_2CH(NH_2)CO_2H$ |
| g | 2-benzothiazole | —$CH_2CH_2CH_2CH_2CH_2CO_2CH_3$ |
| h | 2-benzoxazole | —$CH_2CH_2CH_2CH_2OH$ |
| i | 3-pyridyl | —$CH_2CH_2CH_2CH_2NHCOCH_3$ |
| j | meta-chlorophenyl | -para —$CH_2OC_6H_4CO_2H$ |
| k | meta-chlorophenyl | —$CH_2OCH_2CH_2OCH_3$ |
| l | 2-pyridyl | —$CH_2OCH(CH_3)CON(OH)CH_3$ |
| m | 3-(2-furanyl)phenyl | —$CH_2OCH_2CO_2H$ |
| n | 3-(2-pyridyl)phenyl | —$CH_2CH_2CH_2CH_2NHCOCH_3$ |
| o | 4-pyridyl | —$CH_2CH_2CH_2CH_2NHCO_2CH_3$ |
| p | meta-methylphenyl | —$CH_2CH_2NHCONH_2$ |
| r | meta-methylphenyl | —$CH_2CH_2NHC(=NH)NH_2$ |
| s | 2-pyridyl | —$CH_2CH_2CH_2C(=NOH)CH_3$ |
| t | 2-pyridyl | $CH_2CH_2CH_2C(CH_3)N(OH)COCH_3$ |
| u | 2-pyridyl | —$CH_2CH_2CH_2C(CH_3)N(OH)CONH_2$ |
| v | 3-chlorophenyl | —$CH_2CH_2CH_2CH_2SO_2CH_3$ |
| w | 3-methylphenyl | —$CH_2CH_2SO_2CH_3$ |
| x | 2-pyridyl | —$CH_2CH_2SOC_6H_5$ | f) Scheme X

Triazinone compounds with a substituent group at the 5-position can also be prepared from amino acid derivatives as outlined in Scheme X. The corresponding ester of an amino acid 34 is treated with an aryl or heteroaryl amine 1 in the presence of ethylmagnesium bromide to provide the corresponding aryl or heteroaryl amide 35 which is then reduced to the amino compound 36 with a suitable reducing reagent such as lithium aluminum hydride. Treatment of the intermediate 36 with a chloroformate such as methyl chloroformate in the presence of triethylamine provides the carbamate 37. Nitrosation of 37 leads to the N-nitroso intermediate 38 which is then reduced to the corresponding hydrazine intermediate 39 with a reducing reagent such as zinc in acetic acid. Cyclization to the triazinone of Formula VI is accomplished as previously described. This method is illustrated by Example 97 utilizing the methyl ester hydrochloride salt of DL-serine. This method provides access to either of the two enantiomers of 5-substituted triazinones using D- or L-amino acid starting materials.

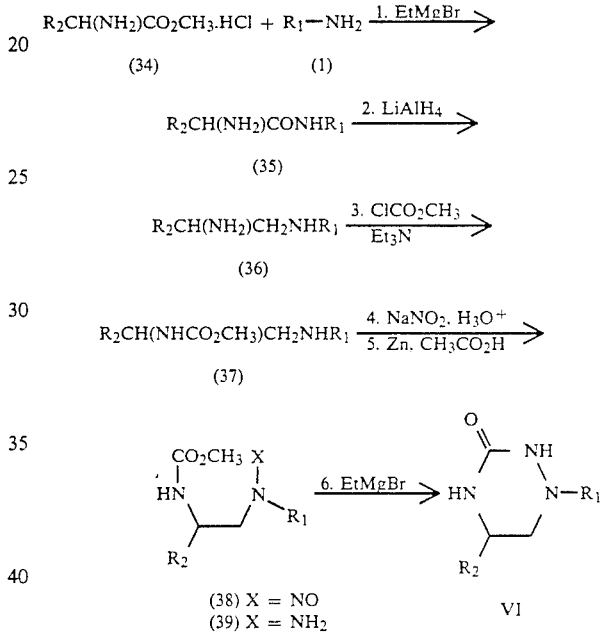

Scheme X

EXAMPLE 97

D,L-5-hydroxymethyl-1-phenyl-2H,4H,tetrahydro-1,2,4-triazin-3-one

Formula VI, $R_1$=phenyl, $R_2$=hydroxymethyl a). A solution of aniline (2.79 g, 0.03 mol) in dichloromethane (10 mL) was cooled to 0° C. and stirred under nitrogen and a 2N solution of ethylmagnesium bromide in tetrahydrofuran (15.0 ml, 0.03 mol) was added dropwise. The mixture was stirred for 30 min. followed by portionwise addition of DL-serine methyl ester hydrochloride (1.56 g, 0.01 mol) over a 1 h period. The thick reaction mixture was diluted with additional dichloromethane (10 mL) and heated at reflux for three days. After being allowed to cool, the mixture was treated with a saturated aqueous NH$_4$Cl (5 mL) and extracted twice with dichloromethane (100 mL). The dichloromethane layer was dried over MgSO$_4$, concentrated and the residue titrated in pentane-ether (1:1) to give a solid product, m. p. 116°–118° C.

b). The product from part a (1.96 g, 0.01 mol) was dissolved in dry tetrahydrofuran (50 mL) and added dropwise to a suspension of lithium aluminum hydride (0.836 g, 0.022 mol) in dry tetrahydrofuran (35 mL)

with stirring at room temperature under a nitrogen atmosphere. The mixture was stirred at reflux overnight, cooled and quenched by dropwise addition of water (0.9 mL), then followed by 15% NaOH solution (0.9 mL) and water (2.7 mL). The mixture was stirred for 3 h, filtered and the filtrate was concentrated. The residue, which began to solidify within a short time, was triturated in ether (10 mL) and the solid collected to give a solid product (1.2 g), m. p. 89°-92° C.

c). A mixture of the product from part b (1.20 g, 0.007 mol) and triethylamine (0.73 g, 0.007 mol) in dry tetrahydrofuran (50 mL) was stirred at −5° C. while a solution of methyl chloroformate (0.68 g, 0.007 mol) in dry tetrahydrofuran (15 mL) was slowly introduced. The mixture was stirred at −5° C. for two hours, allowed to warm to room temperature and filtered. The filtrate was concentrated to give a carbamate intermediate (1.73 g).

d). A mixture of the product from part c (1.73 g, 0.0077 mol), concentrated hydrochloric acid (2.0 mL), water (10 mL) and dimethoxyethane (6 mL) was stirred at 0° C. and a solution of sodium nitrite (0.59 g, 0.0085 mol) in water (1.0 mL) was added dropwise. The mixture was stirred at 0° C. for 1 hour, extracted with dichloromethane (100 mL) and the extract concentrated to give a residue (1.78 g).

e). To a stirred suspension of zinc dust (1.80 g, 0.027 mol) in water (5.3 mL) cooled to 15° C., was gradually added a solution of the residue from part d (1.78 g, 0.007 mol) in glacial acetic acid (4.5 mL). After the addition, the cooling bath was removed and the mixture was stirred at room temperature for 1 h. Dichloromethane (10 mL) was added and the mixture was adjusted to pH 6 with 15% NaOH. The organic and aqueous layers were decanted from the zinc residue which was extracted with a fresh portion (10 mL) of dichloromethane. The combined organic layers were dried over MgSO4 and concentrated to yield the hydrazine intermediate (1.53 g).

f). The hydrazine from part e (1.53 g, 0.006 mol) was dissolved in dichloromethane (10 mL), chilled to −30° C. and treated with a 2M solution of ethylmagnesium bromide in tetrahydrofuran (12.0 mL, 0.024 mol). The mixture was heated at 45°-50° C. for four days, cooled and treated with a solution of concentrated hydrochloric acid (2.0 mL) in methanol (25 mL). The mixture was concentrated and the residue extracted with 10% methanol in dichloromethane (4×25 mL). The extracts were dried over MgSO4, concentrated and the residue purified by chromatography (silica gel, dichloromethane-methanol), to give the title compound.

m.p.=223°-224° C. dec.

1H NMR (300 MHz, DMSO-d6) 3.08-3.30 (4H, m), 4.01 (1H, d, J=10.5 Hz), 4.77 (1H, t, J=6.0 Hz), 6.46 (1H, br s), 6.86 (1H, t, J=7.5 Hz), 7.02 (2H, d, J=7.5 Hz), 7.26 (2H, t, J=7.5 Hz), 8.47 (1H, d, J=1.5 Hz).

Mass spectrum: $(M+H)^+ = 208$

Anal calc'd for $C_{10}H_{13}N_3O_2$: C, 57.96; H, 6.32; N, 20.28.

Anal. Found: C, 57.54; H, 6.28; N 19.87.

Another preferred embodiment of this reaction scheme is by starting with an intermediate such as (36), for instance when $R_1$ is phenyl and $R_2=H$. Treatment of phenylethylenediamine with ethylchloroformate and triethylamine produces the carbamate intermediate (37). The carbamate (37) is reacted with sodium nitrate in the presence of an acid to produce the N-nitroso intermediate which is reduced with a zinc catalyst to provide the hydrazine intermediate (39). The hydrazine intermediate (39) is cyclized with ethylmagnesium bromide to produce triazinone compounds of Formula VI as illustrated in the following example.

EXAMPLE 98

1-phenyl-2H,4H-tetrahydro-1,2,4-triazin-3-one

Formula VI, $R_1$=phenyl, $R_2$=H a) Ethyl chloroformate (70.6 mL, 0.735 mole) was slowly added to a cooled (0°-5° C.) solution of N-phenylethylenediamine (100 g, 0.735 mole) and triethylamine (104 mL, 0.735 mole) in dichloromethane (500 mL) while stirring under nitrogen and maintaining the reaction temperature below 5° C. The mixture was stirred one hour, after which saturated aqueous NH4Cl was added (200 mL) and the pH was adjusted to 6.5 with 3N HCl. The layers were separated, and the aqueous layer was extracted with dichloromethane (2×200 mL). The combined organic extracts were washed with saturated aqueous NaCl, dried over MgSO4, filtered and evaporated to provide a residue (150 g).

b) The residue from part a (150 g, 0.721 mole) was suspended in a cold (5° C.) mixture of water (100 mL) and conc. HCl (160 mL). With mechanical stirring a cold (5° C.) solution of NaNO2 (52 g, 0.72 mole) in water (160° mL) was added slowly. The mixture was stirred for 30 min. and dichloromethane (500 mL) was added. The layers were separated, the organic layer was washed with saturated aqueous NaCl, dried over MgSO4, filtered and evaporated to give a residue (150 g).

c) The residue from part b (150 g, 0.63 mole) was dissolved in acetic acid (220 mL) and with mechanical stirring was added dropwise to a suspension of zinc (164 g, 2.5 mole) in water (400 mL). The temperature of the reaction was maintained between 10°-15° C., and after the addition the mixture was allowed to warm to room temperature for 45 minutes. Dichloromethane (500 mL) was added and the mixture was filtered. The solids (excess zinc) were washed with dichloromethane (2×50 mL), and the combined organic extract was washed with 10% aqueous Na2CO3, saturated aqueous NaCL, dried over MgSO4, filtered and evaporated to provide a residue (135 g).

d) The residue from part c (135 g, 0.60 mole) was dissolved in dicholormethane (500 mL) and cooled to −20° C. under nitrogen. Ethylmagnesium bromide (310 mL, 2M in tetrahydrofuran) was added slowly. The mixture was refluxed for two days. The mixture was allowed to cool and ice chips (200 g) were added whereupon a precipitate formed in the aqueous layer. The mixture was acidified to pH 3 with 3N HCl. More dicholormethane (400 mL) was added, and the mixture was shaken for 5 minutes after which, a new precipitate formed in the dicholormethane layer. The organic layer together with suspended precipitate was separated from the aqueous layer and then cooled at 5° C. for 1-2 hours. The mixture was filtered while cold using a sintered funnel to provide a solid (52.5 g). This material was dissolved in a mixture of 10% methanol in chloroform and then washed with in HCl (100 mL) and evaporated to give a solid. This material was washed with dichloromethane (50 mL) and dried in vacuo to provide the desired product (47 g, 44%), mp 211°-213° C.

1H NMR (300 MHz, DMSO d6) 3.02 (2H, m), 3.62 (2H, t), 6.65 (1H, br s), 6.83-7.23 (5H, m), 8.42 (1H, s).

Mass spectrum: $M+ = 178$

Anal Calc'd. for $C_9H_{11}N_3O$ : C, 61.00; H, 6.26; N, 23.71.

Anal. Found : C, 60.83; H, 6.29; N, 23.72.

A more preferred route to the products of example 98 is provided by the method of Scheme VII in an analogous manner as example 88.

g) Scheme XI

Triazinone compounds with a substituent group at the 4-position can be prepared as outlined in Scheme XI. Acylation of a diamine starting material 40, where the choice of the carboxylic acid chloride will determine the nature of the substituent $R_4$, provides the intermediate aminoamide 42. Reduction of 42 with a reducing agent such as lithium aluminum hydride provides the substituted diamine 43 which is reacted with a chloroformate such as methyl chloroformate in the presence of a base such as triethylamine to provide the intermediate carbamate 44. The sequence of reactions involving nitrosation to the N-nitroso intermediate 45, reduction to the hydrazine 46, and cyclization as prevously described, provides triazinone compounds of Formula V.

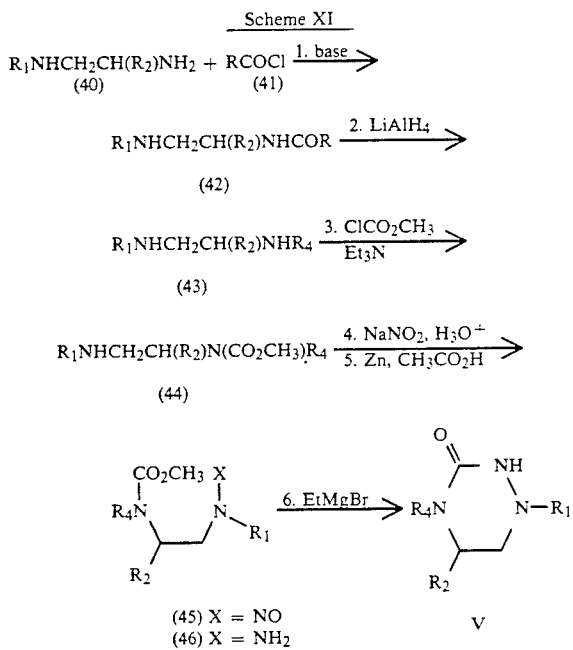

Scheme XI

EXAMPLE 99

4-Benzyl-1-phenyl-2H,4H-tetrahydro-1,2,4-triazin-3-one

Formula V, $R_1$=phenyl, $R_4$=benzyl a). A mixture of N-phenylethylenediamine (24.4 g, 0.179 mol) and triethylamine (18.1 g, 0.179 mol) in dichloromethane (100 mL) was stirred and cooled in a ice-salt mixture while a solution of benzoyl chloride (25.2 g, 0.179 mol) in dichloromethane (50 mL) was introduced dropwise at a rate so as to keep the internal temperature below 6° C. After being kept at room temperature overnight, the reaction mixture was washed with 5% NH$_4$Cl (2×75 mL), the organic layer was dried over MgSO$_4$ and concentrated in vacuo to yield 37.8 g of product which could be crystallized from benzene. m. p. 125°–127° C.

b). To a suspension of LiAlH$_4$ (3.80 g, 0.10 mol) in dry tetrahydrofuran (100 mL) was added dropwise with stirring a solution of the compound prepared in part a (12.02 g, 0.05 mol) in tetrahydrofuran (50 mL). The mixture was stirred at reflux overnight under a nitrogen atmosphere. After careful addition of water (3.8 mL), followed by 15% sodium hydroxide solution (3.8 mL) and water (11.3 mL), the mixture was stirred at room temperature for 1.5 hr and filtered. Evaporation of the filtrate provided the N-benzyl compound.

c). The intermediate from part b (11.29 g, 0.049 mol) was treated with methyl chloroformate (4.68 g, 0.049 mol) and triethylamine (5.00 g, 0.049 mol) in dichloromethane (100 mL) in a manner identical to part a to give the carbamate (13.8 g).

d). The carbamate from part c (13.8 g, 0.048 mol) dissolved in dimethoxyethane (20 mL) was treated with concentrated hydrochloric acid (9.1 mL) in water (45 mL) and cooled to 5° C. while a solution of sodium nitrite (3.33 g, 0.048 mol) in water (6 mL) was slowly introduced with stirring. The product which separated as a heavy oil was extracted into dichloromethane, dried over MgSO$_4$ and concentrated to give the nitroso intermediate.

e). A solution of the intermediate from part d (17.0 g, 0.054 mol) in glacial acetic acid (30 mL) was introduced dropwise into a mechanically stirred suspension of zinc dust (14.2 g) in water (35 mL) which was cooled in ice water during the addition so that the internal termperature remained in the 15°–20° C. range. The cooling bath was removed and the stirring continued for another hour during which time the internal temperature reached 37° C. within 10 min. The reaction mixture was treated with dichloromethane (200 mL) and water (100 mL) and filtered to remove zinc residue. The filtrate was treated with 6 N sodium hydroxide solution to pH 6 and the layers were separated. The organic extract was dried over MgSO$_4$ and concentrated to give the crude hydrazine (16.0 g).

f). The hydrazine from part e (15.0 g, 0.05 mol) was dissolved in dichloromethane (50 mL) and treated at −30° C. with 2M ethylmagnesium bromide in tetrahydrofuran (31.0 mL, 0.062 mol) under nitrogen. The mixture was gently warmed at 45° C. for three days, cooled, treated with ice and 3N hydrochloric acid to pH 4–5 and the layers separated. The organic layer was dried over MgSO$_4$, concentrated and the residue triturated in ether. The crude product was crystallized from benzene to give 3.79 g of the title compound.

m.p.=164°–166° C.

$^1$H NMR (300 MHz, DMSO-d$_6$) 3.02 (2H, t, J=6.0 Hz), 3.75 (2H t J=6.0 Hz) 4.42 (2H s) 6.89 (1H, t, J=7.5 Hz), 7.02–7.15 (4H, m), 7.17–7.34 (5H, m), 8.71 (1H, s).

Mass spectrum: $(M+H)^+ = 268$

Anal Calc'd for $C_{16}H_{17}N_3O$: C, 71.89; H, 6.41; N, 15.72.

Anal Found: C, 71.82; H, 6.50; N, 15.72.

EXAMPLE 100

4-Ethyl-1-phenyl-2H,4H-tetrahydro-1,2,4-triazin-3-one

Formula V, $R_1$=phenyl, $R_4$=ethyl

The title compound was prepared according to Scheme XI in an analogous manner as Example 99 except acetyl chloride was used in part a instead of benzoyl chloride.

m.p.=152.5°–154.5° C.

¹H NMR (300 MHz, DMSO-d₆) 0.94 (3H, t, J=7.5 Hz), 3.11 (2H, t, J=6.0 Hz), 3.18 (2H, q, J=7.5 Hz), 3.73 (2H, t, J=6.0 Hz), 6.87 (1H, t, J=7.5 Hz), 7.03 (2H, d, J=7.5 Hz), 7.26 (2H, t, J=7.5 Hz), 8.43 (1H, s)

Mass spectrum: $(M+H)^+ = 206$

Anal. Calc'd for $C_{11}H_{15}N_3O$: C, 64.37; H, 7.37; N, 20.47.

Anal. Found: C, 64.22; H, 7.39; N, 20.36.

EXAMPLE 101

4-Methyl-1-phenyl-2H,4H-tetrahydro-1,2,4-triazin-3-one

Formula V, $R_1$=phenyl, $R_4$=methyl

The title compound was prepared according to Scheme XI in an analogous manner as Example 99 except methyl chloroformate was used in part a instead of benzoyl chloride.

m.p.=174°–178° C.

¹H NMR (300 MHz, DMSO-d₆) 2.73 (3H, s), 3.11 (2H, t, J=6.0 Hz), 3.74 (2H, t, J=6.0 Hz), 6.87 (1H,t,J=7.5 Hz), 7.02 (2H, d, J=7.5 Hz), 7.26 (2H,t, J=7.5 Hz), 8.49 (1H, s)

Mass spectrum: $(M+H)^+ = 192$

Anal. Calc'd. for $C_{10}H_{13}N_3O$: C, 62.81; H, 6.85; N, 21.97.

Anal. Found: C, 62.54; H, 6.87; N, 21.82.

The following compounds of general Formula V shown In Table 8 are prepared according to the method of Scheme XI in an analogous manner as Example 99 except substituting the appropriate diamine 40 and acyl chloride 41.

TABLE 8

| | Formula V compounds | | |
|---|---|---|---|
| Example | $R_1$ | $R_2$ = | $R_4$ = |
| a | meta-chlorophenyl | —CH₂CH₃ | CH₂C₆H₅ |
| b | 2-pyridyl | —CH₃ | CH₂OCH₂C₆H₅ |
| c | 4-pyridyl | —CH₂(CH₃)₂ | CH₂C₆H₅ |
| d | 4-pyridyl | —CH₃ | CH₂C₆H₅ |
| e | 2-pyridyl | —CH₃ | CH₂C₆H₅ |
| f | 2-benzothiophenyl | —CH₃ | CH₂C₆H₅ |
| g | 3-(2-pyridyl)phenyl | —CH₃ | CH₂C₆H₅ |
| h | 4-pyridyl | —CH₃ | (CH₂)₃CH₃ |
| i | 2-quinoyl | —CH₃ | CH₂C₆H₅ |
| j | 2-benzothiazole | —CH₃ | (CH₂)₃CH₃ |
| k | 2-benzoxazole | —CH₃ | (CH₂)₃CH₃ |
| l | 3-pyridyl | —CH₃ | CH₂C₆H₅ |
| m | 3-(2-furanyl)phenyl | —CH₃ | CH₂C₆H₅ |

Triazinone and pyridazinone compounds of formula I with A=CO can be converted to the corresponding thiocarbonyl analogs of Formula I with A=CS by treatment with a suitable reagent such as Lawesson's Reagent (2,4-bis(4-methoxy-phenyl)-1,3-dithia-2,4-diphosphetane-2,4-disulfide). The following examples illustrate this method.

EXAMPLE 102

1-Phenyl-2H,4H-tetrahydro-1,2,4-triazin-3-thione.

Formula I, A=CS, B=NH, $R_1$=phenyl, $R_2$=Z=H.

To a suspension of 1-phenyl-2H, 4H-triazin-3-one (4.0 g, 23 mmol) in toluene (150 mL) was added Lawesson's Reagent (2,4-bis(4-methoxyphenyl)-1,3-dithia-2,4-diphosphetane-2,4-disulfide, 10,0 g). The mixture was heated at 80° C. for 15 h, then cooled and a mixture of methanol and dichloromethane (1:1, 50 mL) and water (100 mL) was added. The organic layer was collected and concentrated to provide a residue which was purified by chromatography (silica gel, 5% methanol in dichloromethane) to provide the title compound (1.8 g).

m.p.=180° C.

1H NMR (300 MHz, DMSO-d₆) 2.95–3.02 (2H, m), 3.63 (2H, t, J=5 Hz), 6.91–7.01 (3H, m), 7.30 (2H, t, J=7.5 Hz), 8.39 (1H, br s), 9.97 (1H, br s).

Mass spectrum $(M+H)^+ = 194$

Anal. Calc'd for $C_9H_{11}N_3S$: C, 55.93; H, 5.74; N, 21.74.

Anal found: C, 55.16; H, 5.66; N, 21.04.

EXAMPLE 103

1-(3-Chlorophenyl)-2H,4H-tetrahydro-1,2,4-triazin-3-thione

Formula I, A=CS, B=NH, $R_1$=3chlorophenyl, $R_2$=Z=H

The title compound was prepared according in an analogous manner as Example 102, except 1-(3-chlorophenyl)-2H,4H-tetrahydro-1,2,4-triazin-3-one was used instead of 1-phenyl-2H,4H-triazin-3-one.

m.p.=204°–205 ° C.

1H NMR (300 MHz, DMSO-d₆) 2.97–3.05 (2H, m), 3.69 (2H, t, J=5 Hz), 6.95–7.04 (3H, m), 7.32 (1H, t, J=7.5 Hz), 8.5 (1H, br s), 10.1 (1H, br s).

Mass spectrum $(M+H)^+ = 228$

Anal. Calc'd for $C_9H_{10}ClN_3S$: C, 47.47; H, 4.43; N, 18.45.

Anal. found: C, 46.46; H, 4.11; N, 17.13.

EXAMPLE 104

1-phenyl-2H-tetrahydropyridazin-3-thione

Formula I, A=CS, B=CH₂, $R_1$=C₆H₅, $R_2$=Z=H

The title compound was prepared in an analogous manner, as in Example 102 except that 1-phenyl-2H-tetrahydropyridazin-3-one was used instead of the 1,2,4-triazin-3-one.

mp. 108° C.

¹H NMR (300 MHz, CDCL3) 1.90 (2H, n), 2.90 (@h, t, J=7 Hz), 3.65 (2H, t, JH=7 Hz), 7.02 (2H, m), 7.35 (3H, m) 9.2 (1H, br s).

Mass spectrum M $+ = 192$

EXAMPLE 105

1-(3'-fluorophenyl-2H-tetrahydro-pyridazin-3-thione

Formula I, A=CS, B=CH₂, $R_1$=3-fluorophenyl, $R_2$=Z=H

The title compound was prepared in an analogous manner as in Example 102 except that 3'-fluorophenyl-2H-tetrahydropyridazin-3-one was used instead of the 1,2,4-triazin-3-one.

mp. 108° C.

¹H NMR (300 MHz, CDCl₃) 1.98 (2H, m), 3.65 (2H, t, J=6 Hz), 6.73 (3H, m), 7.23–7.28 (1H, d, J=6 Jz), 9.25 (1H, br s).

Mass spectrum: M+ =210

EXAMPLE 106

1-(3'-methylphenyl)-2H-tetrahydro-pyridazin-3-thione

Formula I, A=CS, B=CH₂, $R_1$=3 -methylphenyl, $R_2$=Z=H

The title compound was prepared in an analogous manner as Example 102 except that 1-(3'methylphenyl)-2H-tetrahydropyridazin-3-one was used instead of the 1,2,4-triazin-3-one.

mp 124½

¹H NMR (300 MHz, CDCl 1.88 (2H, m), 2.34 (3H, s), 2.93 (2H, t, J=7.5 Hz), 7.22 (1H, m), 9.24 (1H, br s).

Mass spectrum: M+=206

The following compounds of Formula I listed in Table 9, can be prepared in an analogous manner as described for Example 102.

TABLE 9
| Formula I compounds |
| --- |
| 1-(3'-ethylphenyl)-2H,4H-tetrahydro-1,2,4-triazin-3-thione |
| Formula I, A = CS, B = NH, R1 = 3-ethylphenyl, R2 = Z = H |
| 1-(4'-phenoxyphenyl)-5-methyl-2H,4H-tetrahydro-1,2,4-triazin-3-thione |
| Formula I, A = CS, B = NH, R1 = 4-phenoxyphenyl, R2 = 5-CH3, Z = H |
| 1-(3-methoxyphenyl)-4-methyl-2H-tetrahydro-1,2,4-triazin-3-thione |
| Formula I, A = CS, B = NCH3, R1 = 3-methoxyphenyl, R2 = Z = H |
| 4-phenyl-3H-trihydro-1,3,4-oxadiazin-2-thione |
| Formula I, A = CS, B = O, R1 = phenyl, R2= Z = H |

The following compounds shown in Table 10 are prepared in an analogous manner as Example 102 by applying the method to the appropriate triazinones of Formula V

TABLE 10
Formula I, A = CS, B = NR4, Z = H, compounds

| Example | R1 | R2 = | R4 = |
| --- | --- | --- | --- |
| a | meta-chlorophenyl | —CH2CH3 | CH2C6H5 |
| b | 2-pyridyl | —CH3 | CH2OCH2C6H5 |
| c | 4-pyridyl | —CH2(CH3)2 | CH2C6H5 |
| d | 4-pyridyl | —CH3 | CH2C6H5 |
| e | 2-pyridyl | —CH3 | CH2C6H5 |
| f | 2-benzothiophenyl | —CH3 | CH2C6H5 |
| g | 3-(2-pyridyl)phenyl | —CH3 | CH2C6H5 |
| h | 4-pyridyl | —CH3 | (CH2)3CH3 |
| i | 2-quinoyl | —CH3 | CH2C6H5 |
| j | 2-benzothiazole | —CH3 | (CH2)3CH3 |
| k | 2-benzoxazole | —CH3 | (CH2)3CH3 |
| l | 3-pyridyl | —CH3 | CH2C6H5 |
| m | 3-(2-furanyl)phenyl | —CH3 | CH2C6H5 |

| example | R1 | R2 | R4 = H |
| --- | --- | --- | --- |
| n | 4-pyridyl | —CH2CH2CH2OH | |
| o | 2-benzoxazole | —CH2CH2CH2CH2OH | |
| p | meta-chlorophenyl | —CH2OCH2CH2OCH3 | |
| q | meta-methylphenyl | —CH2CH2NHC(=NH)NH2 | |
| r | 2-pyridyl | —CH2CH2CH2C(=NOH)CH3 | |
| s | 3-chlorophenyl | —CH2CH2CH2CH2SO2CH3 | |
| t | 3-methylphenyl | —CH2CH2SO2CH3 | |
| u | 2-pyridyl | —CH2CH2SOC6H5 | |
| v | meta-methylphenyl | —CN | |
| w | meta-chlorophenyl | —CH2OCH2CH2OH | |
| x | meta-chlorophenyl | —C=NOCH3 | |
| y | meta-methylphenyl | —CH2OCH2CH=CH2 | |
| z | meta-chlorophenyl | —CH2OCH2C≡CH | |
| aa | 2-benzothiazole | —COCH2CH2CH2CH3 | | h) Scheme XII

Triazinone compounds of the Formula VI can be converted to the 4-substituted analogs of Formula V as outlined in Scheme XII. Treatment of a triazinone with an acylating reagent such as a carboxylic anhydride in the presence of a suitable base provides the intermediate47. Selective hydrolysis of the 2-acyl substituent provides the triazinones of Formula V. The intermediates 47 can be converted in vivo to the corresponding triazinones V and therefore they can serve as prodrug precursors to active inhibitors of 5-lipoxygenase.

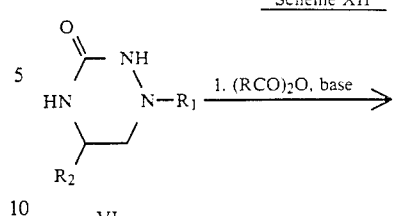
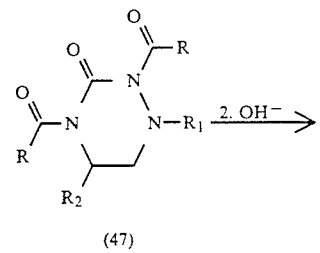
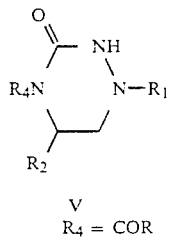

Scheme XII

EXAMPLE 107

4-Acetyl-1-phenyl-2H,4H-tetrahydro-1,2,4-triazin-3-one

Formula V, R1=phenyl, R4=acetyl, R2=H a). 1-Phenyl-2H,4H-tetrahydro-1,2,4-triazin-3-one (3.24 g, 0.018 mole) was added to a stirred suspension of sodium hydride (60% in mineral oil, 1.70 g, 0.04 mol) in dry benzene (250 mL). The mixture was stirred at room temperature for 15 min. and then acetic anhydride (4.10 g, 0.04 mole) was added. The mixture was stirred at 110° C. for 24 hrs., cooled and poured into dichloromethane (300 mL). A saturated aqueous solution of NH$_4$Cl (75 mL) was added, the organic layer was dried over MgSO$_4$, concentrated and the residue titrurated in ether-hexane to give the diacetyl derivative (2.47 g).

m. p.=82°-85° C.

$^1$H NMR (300 MHz, DMSO-d$_6$) 2.27 (3H, s), 2.44 (3H, s), 3.44-3.83 (3H, m), 4.41 (1H, br s), 6.88-6.97 (3H, m), 7.25-7.35 (2H, t, J=9.0 Hz).

Mass spectrum: (M+H)$^+$=262

Anal. Calc'd for C$_{13}$H$_{15}$N$_3$O$_3$: C, 59.76; H, 5.79; N, 16.08

Anal. Found: C, 59.47; H, 5.90; N, 16.19 b). The diacetyl derivative from part a (1.93 g, 0.007 mole) was treated with methanol (40 mL), water (8 mL) and sodium bicarbonate (0.10 g). The mixture was stirred at room temperature for 24 h followed by concentration in vacuo. The residue was extracted with dichloromethane (50 mL), the extract was dried over MgSO$_4$ and concentrated. The resulting crude product was purified by chromatography (silica gel, CH$_2$Cl$_2$—Et$_2$O, (1:1) then CH$_2$Cl$_2$—CH$_3$OH, 9:1) to give 0.75 g of the monoacetyl product.

m. p.=144°-147° C.

$^1$H NMR (300 MHz, DMSO-d$_6$) 2.36 (3H, s), 3.49 (2H, t, J=6.0 Hz), 3.87 (2H, t, J=6.0 Hz), 6.92 (1H, t, J=7.5 Hz), 7.05 (2H, d, J=7.5 Hz), 7.29 (2H, t, J=7.5 Hz), 9.67 (1H, s).

Mass spectrum: (M+H)$^+$=220

Anal. Calc'd for C$_{11}$H$_{13}$N$_3$O$_2$: C, 60.26; H, 5.98; N, 19.17.

Anal. Found: C, 59.95; H, 5.98; N, 19.06.

EXAMPLE 108

4-Acetyl-5-methyl-1-phenyl-2H,4H-tetrahydro-1,2,4-triazin-3-one

Formula V, R$_1$=phenyl, R$_4$=acetyl, R$_2$=methyl

The title compound was prepared according to Scheme XII in an analogous manner as Example 107, except 5-methyl-1-phenyl-2H,4H-tetrahydro-1,2,4-triazin-3-one was used in part a instead of 1-phenyl-2H,4H-tetrahydro-1,2,4-triazin-3-one.

m.p.=93°-97° C.

$^1$H NMR (300 MHz, DMSO-d$_6$) 1.08 (3H, d, J=6.0 Hz), 2.18 (3H, s), 3.41 (1H, m), 4.24-4.40 (2H, m), 6.86 (1H, t, J=7.5 Hz), 7.03 (2H, d, J=7.5 Hz), 7.26 (2H, t, J=7.5 Hz), 9.92 (1H, s).

Mass spectrum: (M+H)$^+$=234

Anal. Calc'd. for C$_{12}$H$_{15}$N$_3$O$_2$: C, 61.79; H, 6.48; N, 18.01.

Anal. Found: C, 61.91; H, 6.61; N, 18.06.

EXAMPLE 109

4-Isobutyryl-1-phenyl-2H,4H-tetrahydro-1,2,4-triazin-3-one

Formula V, R$_1$=phenyl, R$_4$=isobutyryl, R$_2$=H

The title compound was prepared according to Scheme XII in an analogous manner as Example 107 except isobutyric anhydride was used in part a instead of acetic anhydride.

m.p.=125°-126° C.

$^1$H NMR (300 MHz, DMSO-d$_6$) 0.95 (6H, d, J=6 Hz), 3.48 (2H, t, J=7.0 Hz), 3.66-3.72 (1H, m), 3.87 (2H, t, J=7.0 Hz), 6.89-7.92 (1H, m), 7.03 (2H, d, J=5 Hz), 7.29 (2H, t, J=5 Hz), 9.69 (1H, s).

Mass spectrum: M+=248

Anal. Calc'd. for C$_{13}$H$_{17}$N$_3$O$_2$: C, 63.14; H, 6.93; N, 16.99.

Anal. Found: C, 63.17; H, 7.08; N, 16.48.

EXAMPLE 110

4-Propionyl-1-phenyl-2H,4H-tetrahydro-1,2,4-triazin-3-one

Formula V, R$_1$=phenyl, R$_4$=propionyl, R$_2$=H

The title compound was prepared according to Scheme XII in an analogous manner as Example 107 except propionic anhydride was used in part a instead of acetic-anhydride.

m.p.=125°-126° C.

$^1$H NMR (300 MHz, DMSO-d$_6$) 0.98 (3H, t, J=7.5 Hz), 2.81 (2H, q, J=7 Hz), 3.5 (2H, t, J=6 Hz), 3.87 (2H, t, J=6 Hz), 6.91 (1H, t, J=7.5 Hz), 7.04 (2H, d, J=7 Hz), 7.28 (2H, t, J=8 Hz), 9.63 (1H, br s).

Mass spectrum: M+=234

Anal Calc'd. for C$_{12}$H$_{14}$N$_3$O$_2$: C, 62.05; H, 6.08; N, 18.09.

Anal. Found: C, 62.33; H, 6.62; N, 18.03.

EXAMPLE 111

4-Acetyl-1-(3-chlorophenyl)-2H,4H-tetrahydro-1,2,4-triazin-3-one

Formula V, R$_1$=3-chlorophenyl, R$_4$=acetyl, R$_2$=H

The title compound was prepared according to Scheme XII in an analogous manner as Example 107 except 1-(3-chlorophenyl)-2H,4H-tetrahydro-1,2,4-triazin-3-one was used in part a instead of 1-phenyl-2H,4H-tetrahydro-1,2,4-triazinone.

m.p.=162° C.

$^1$H NMR (300 MHz, DMSO-d$_6$) 2.35 (3H, s), 3.52 (2H, t, J=6 Hz), 3.92 (2H, t, J=6 Hz), 6.95 (1H, d, J=7.0 Hz), 7.03 (1H, d, J=7.0 Hz), 7.1 (1H, s), 7.3 (1H, t, J=7.5 Hz), 9.75 (1H, s).

Mass spectrum: M+=254

Anal. Calc'd for C$_{11}$H$_{12}$Cl$_1$N$_3$O$_2$: C, 52.08; H, 4.77; N, 16.56.

Anal. Found: C, 51.68; H, 4.63; N, 16.46.

The following compounds of general Formula V shown in Table 11 may be prepared according to the method of scheme XII in an analagous manner as Example 107 by applying the method to the appropriate triazinone of Formula VI.

TABLE 11

| | Formula V compounds. | | |
|---|---|---|---|
| Example | R$_1$ | R$_2$ | R$_4$ |
| a | meta-chlorphenyl | CH$_3$ | CH$_2$C$_6$H$_5$ |
| b | 2-pyridyl | CH$_3$ | CH$_2$OCH$_2$C$_6$H$_5$ |
| c | 4-pyridyl | CH$_2$(CH$_3$)$_2$ | CH$_3$ |
| d | 4-pyridyl | CH$_3$ | CH$_3$ |
| e | 2-pyridyl | CH$_3$ | CH(CH$_3$)$_2$ |
| f | 2-benzothiophenyl | CH$_3$ | CH$_2$C$_6$H$_5$ |
| g | 3-(-2-pyridyl)phenyl | CH$_3$ | CH$_2$C$_6$H$_5$ |
| h | 4-pyridyl | CH$_3$ | (CH$_2$)$_3$CH$_3$ |
| i | 2-quinoyl | CH$_3$ | CH$_2$C$_6$H$_5$ |
| j | 2-benzothiazole | CH$_3$ | CH$_3$ |
| k | 2-benzoxazole | CH$_3$ | CH$_3$ |
| l | 3-pyridyl | CH$_3$ | OCH$_3$ |
| m | 3-(2-furanyl)phenyl | CH$_3$ | OCH$_3$ |
| n | 4-pyridyl | CH$_3$ | (CH$_2$)$_2$CO$_2$H |
| o | meta-chlorophenyl | CH$_3$ | (CH$_2$)$_4$CO$_2$H |
| p | 2-benzothiophenyl | CH$_3$ | (CH$_2$)$_4$CO$_2$H |
| q | meta-chlorophenyl | CH$_3$ | (CH$_2$)$_4$CO$_2$H |

TABLE 11-continued

| | Formula V compounds. | | |
|---|---|---|---|
| Example | R₁ | R₂ | R₄ |
| r | meta-chlorophenyl | CH₃ | CH₂OH |
| s | 4-pyridyl | CH₃ | (CH₂)₃CH₂OH |

III. Oxapyridazinone Synthesis

Oxapyridazinone compounds of this invention having the general Formula VII can be prepared according to Scheme XIII. The aryl hydrazine (48) is reacted with a substituted 2-bromoethanol derivative (49) and diisopropylethylamine to produce the hydroxyhydrazine intermediate (50). The hydroxyhydrazine (50) is heated with acid and then neutralized to provide the hydroxyhydrazine which is reacted with carbonyl diimidazole (CO(IM)₂) or phosgene to produce the oxapyridazinone (VII).

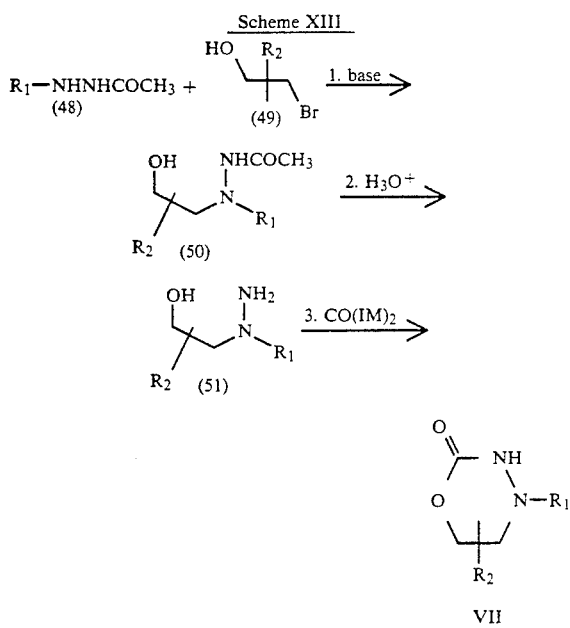

Scheme XIII

EXAMPLE 112

4-phenyl-3H-trihydro-1,3,4-oxadiazin-2-one

Formula VII, R₁=phenyl, R₂=H a) Acetyl-2-(2'-hydroxy)ethyl-2-phenyl hydrazine

A solution of acetyl 2-phenylhydrazine (75.3 g, 0.5 mole), 2-bromoethanol (64.0 g, 0.55 mole) and diisopropylethylamine (68.0 g, 0.55 mole) in toluene (300 mL) was refluxed with stirring for 48 hours under nitrogen. The mixture was allowed to cool to room temperature and dichloromethane (500 mL) and water (250 mL) were added. The organic layer was washed with water (2×250 mL), dried over MgSO₄, filtered and evaporated to give a brown oil. This residue was purified by column chromatography (silica gel, 10% methanol in dichloromethane) to provide the desired intermediate (30.4 g).

b) 1-(2'-hydroxy)ethyl-1-phenylhydrazine

The product from part a (13.5 g, 0.07 mole) in 6N HCl (50 mL) was refluxed under nitrogen for 2 hours. The mixture was cooled in an ice bath, and 6N KOH was added until the solution was neutral (pH 7). The mixture was extracted with ethyl acetate (5×100 mL) and the combined organic extract was dried over MgSO₄, filtered and evaporated to give the desired intermediate (10.2 g).

c) 4-phenyl-3H-trihydro-1,3,4-oxadiazin-2-one

To the product of part b (10.2 g, 0.067 mole) dissolved in tetrahydrofuran (50 mL) was added carbonyl diimidazole (10.9 g, 0.067 mole), and the mixture was stirred at room temperature under nitrogen for 3 hours. Dichloromethane (100 mL) was added, and the organic solution was washed with water (2×50 mL) and aqueous saturated NaCl (50 mL), dried over MgSO₄, filtered and evaporated to give a thick oil (9.4 g). The residue was purified by column chromatography (silica gel, 7% methanol in dichloromethane) followed by recrystallization from ether to provide the desired product (2.28 g), mp 99°-100° C.

NMR (300 MHz,CDCl₃) 3.74 (2H, t, J=10 Hz), 4.29 (2H t, J=10 Hz), 7.08 (3H, m), 7.23 (1H, br), 7.33 (2H, m).

Mass spectrum: M+ =178.

The following compounds of general Formula VII, listed in Table 12, may be prepared according to Scheme XIII in an analogous manner as described for Example 112.

TABLE 12

| Formula VII compounds |
|---|
| 4-(3'-ethylphenyl)-3H-trihydro-1,3,4-oxadiazin-2-one |
| Formula VII, R₁ = 3-ethylphenyl, R₂ = H |
| 4-(4'-phenoxyphenyl)-3H-trihydro-1,3,4-oxadiazin-2-one |
| Formula VII, R₁ = 4-phenoxyphenyl, R₂ = H |
| 4-(phenyl)-6-methyl-3H-trihydro-1,3,4-oxadiazin-2-one |
| Formula VII, R₁ = phenyl, R₂ = 6-methyl |
| 4-(phenyl)-6-butyl-3H-trihydro-1,3,4-oxadiazin-2-one |
| Formula VII, R₁ = phenyl, R₂ = 6-butyl |
| 4,6-diphenyl-3H-trihydro-1,3,4-oxadiazin-2-one |
| Formula VII, R₁ = phenyl, R₂ = phenyl |

IV Synthesis of Compound Containing Metabolically Cleaveable Groups

Pyridazinone, triazinone, and oxapyridazinone compounds of this invention of the general Formula I with Z being a metabolically cleaveable group can be prepared from compounds of the general Formula I with Z=H. A compound of Formula I is condensed with an electrophile Z-X (where X is a leaving group such as halogen, carbonyl, acyl chloride, or an alkyl or aryl formyl chloride, or the like) in the presence of a suitable base to produce a compound of Formula I. The following examples illustrate the above method.

EXAMPLE 113

1-phenyl-2-benzyloxymethyl-2H-tetrahydropyridazin-3-one

Formula I, R₁=phenyl, R₂=H, Z=CH₂OCH₂C₆H₅, A=CO, B=CH₂

To a solution of 1-phenyl-2H-tetrahydropyridazin-3-one (1.76 g, 0.01 mole) in tetrahydrofuran (50 mL) at −78° C. under nitrogen was added with stirring a solution of tert-butyllithium (7 mL of 1.6M pentane solution, 0.011 mole). The mixture was allowed to warm to 5° C. after which benzyl chloromethyl ether (1.6g, 0.011 mole) was added. The mixture was stirred at 5° C. for two hours and 10% aqueous sodium bicarbonate (20 mL) was added followed by dichloromethane (50 mL). The organic layer was separated, dried over MgSO₄, filtered and evaporated to give a residue. Purification by column chromatography (silica gel, 105 ether in dichloromethane) gave the desired product (2.0 g)

$^1$H NMR (300 MHz, CDCl$_3$) 2.07 (2H, m), 2.36 (2H, t, J=7.5 Hz), 3.74 (2H, t, J=6.5 Hz), 4.72 (2H, s), 5.03 (2H, s), 6.92 (3H, m), 7.32 (7H, m).

Mass spectrum: M+ =296

EXAMPLE 114

1-phenyl-2-benzyl-2H-tetrahydropyridazin-3-one

Formula I, R$_1$=phenyl, R$_2$=H, Z=CH$_2$C$_6$H$_5$, A=CO, B=CH$_2$

The title compound was prepared in an analogous manner as Example 113 except benzylbromide was used instead of benzyl chloromethyl ether.

$^1$H NMR (300 MHz, CDCl$_3$) 1.96 (2H, m), 2.36 (2H, t, J=7.5 Hz), 3.42 (2H, t, J=7 Hz), 4.67 (2H, s), 6.87 (2H, d, J=8 Hz), 6.96 (1H, t, J=7.5 Hz), 7.24–7.42 (7H, m).

Mass spectrum: M+ =266

EXAMPLE 115

1-phenyl-2-carbomethoxy-2H-tetrahydropyridazin-3-one

Formula I, R$_1$=phenyl, R$_2$=H, Z=COOCH$_3$, A=CO, B=CH$_2$

The title compound was prepared in an analogous manner as Example 113 except methoxy chloroformate was used instead of benzyl chloromethyl ether.

$^1$H NMR (300 MHz, CDCl$_3$) 2.20 (2H, m), 2.37 (2H, m), 3.88 (5H, m), 6.84 (2H, m), 6.94 (1H, m), 7.30 (2H, m).

Mass spectrum: M+ =234

EXAMPLE 116

1-phenyl-2-propionyl-2H-tetrahydropyridazin-3-one

Formula I, R$_1$=phenyl, R$_2$=H, Z=COCH$_2$CH$_3$, A=CO, B=CH$_2$

The title compound was prepared in an analogous manner as Example 113 except propionyl chloride was used instead of benzyl chloromethyl ether.

$^1$H NMR (300 MHz, CDCl$_3$) 1.19 (3H, t, J=7.5 Hz), 2.05 (2H, m), 2.35 (2H, m), 2.84 (2H, m), 3.46 (1H, m), 4.17 (1H, m), 6.78 (2H, m), 6.92 (1H, m), 7.29 (2H, m).

Mass spectrum: M+ =233

EXAMPLE 117

1-phenyl-2-benzoyl-2H-tetrahydropyridazin-3-one

Formula I, R$_1$=phenyl, R$_2$=H, Z=COC$_6$H$_5$, A=CO, B=CH$_2$

The title compound was prepared in an analogous manner as Example 113 except benzoyl chloride was used instead of benzyl chloromethyl ether.

$^1$H NMR (300 MHz, CDCl$_3$) 2.28 (2H, m), 2.46 (2H, t, J=7.5 Hz), 3.73 (2H, m), 6.94 (3H, m), 7.30 (2H, m), 7.42 (2H, m), 7.52 (1H, m), 7.69 (2H, m).

Mass spectrum: M+ =280

EXAMPLE 118

1-phenyl-2-methoxycarbonylmethyl-2H-tetrahydropyridazin-3-one

Formula I, R$_1$=phenyl, R$_2$=H, Z=CH$_2$CO$_2$CH$_3$, A=CO, B=CH$_2$

The title compound was prepared in an analogous manner as Example 113 except methyl bromoacetate was used instead of benzyl chloromethyl ether.

$^1$H NMR (300 MHz, CDCl$_3$) 2.04 (2H, m), 2.43 (2H, t, J=7.5 Hz), 3.76 (3H, s), 3.89 (2H, m), 4.31 (2H, s), 6.88 (2H, m), 6.98 (1H, m), 7.32 (2H, m).

Mass spectrum: M+ =248

EXAMPLE 119

1-(3'-benzyloxymethylphenyl)-2-benzyl-2H-tetrahydropyridazin-3-one

Formula I, R$_i$=3-benzyloxymethylphenyl, R$_2$=H, Z=CH$_2$C$_6$H$_5$, A=CO, B=CH$_2$ The title compound was prepared in an analogous manner as Example 113 except 1-(3'-benzyloxymethylphenyl)-2H-tetrahydropyridazin-3-one and benzyl bromide were used instead of 1-phenyl-2H-tetrahydropyridazin-3-one and benzyl chloromethyl ether.

$^1$H NMR (300 MHz, CDCl$_3$) 1.83–1.94 (2H, m), 2.22 (2H, t, J=7.5 Hz), 3.49 (2H, m), 4.49 (2H, s), 4.52 (2H, s), 4.59 (2H, s), 6.80–6.95 (3H, m), 7.20–7.42 (11H, m).

Mass spectrum: M+ =386

The following compounds of general Formula I listed in Table 13, may be prepared in an analogous manner as described for Example 113.

TABLE 13

| Formula I compounds |
|---|
| 1-(3'-ethylphenyl)-2-benzoyl-4-methyltetrahydropyridazin-3-one |
| Formula I, R$_1$ = 3-ethylphenyl, R$_2$ = H, Z = COC$_6$H$_5$, A = CO, B = CHCH$_3$ |
| 1-(4'-phenoxyphenyl)-2-propionyl-5-methyltetrahydropyridazin-3-one |
| Formula I, R$_1$ = 4-phenoxyphenyl, R$_2$ = 5-CH$_3$, Z = —COCH$_2$CH$_3$, A = CO, B = CH$_2$ |
| 1-(4'-phenoxyphenyl)-2-methoxymethyl-4-benzyltetrahydropyridazin-3-one |
| Formula I, R$_1$ = 4-phenoxyphenyl, R$_2$ = H, Z = CH$_2$OCH$_3$, A = CO, B = CHCH$_2$C$_6$H$_5$ |
| 1-(3-methoxyphenyl)-2-thiophenylmethyltetrahydropyridazin-3-one |
| Formula I, R$_1$ = 3-methoxyphenyl, R$_2$ = H, Z = CH$_2$SC$_6$H$_5$, A = CO, B = CH$_2$ |
| 4-phenyl-3-benzoyltrihydro-1,3,4-oxadiazin-2-one |
| Formula I, R$_1$ = phenyl, R$_2$ = H, Z = COC$_6$H$_5$, A = CO, B = O |
| 4-(3'-ethylphenyl)-3-benzyl-6-methyltrihydro-1,3,4-oxadiazin-2-one |
| Formula I, R$_1$ = 3-ethylphenyl, R$_2$ = 6-CH$_3$, Z = CH$_2$C$_6$H$_5$, A = CO, B = O |
| 1-phenyl-2-benzoyl-4-methyltetrahydro-1,2,4-triazin-3-one |
| Formula I, R$_1$ = phenyl, R$_2$ = H, Z = COC$_6$H$_5$, A = CO, B = NCH$_3$ |
| 1-(3'-ethylphenyl)-2-benzyl-4-ethyltetrahydro-1,2,4-triazin-3-one |
| Formula I, R$_1$ = 3-ethylphenyl, R$_2$ = H, Z = CH$_2$C$_6$H$_5$, A = CO, B = NCH$_2$CH$_3$ |

INHIBITION OF 5-LIPOXYGENASE

Inhibition of 5-lipoxygenase activity was determined using the 20,000×g supernatant from homogenized RBL-1 cells in a similiar manner as that described by Dyer and coworkers (Dyer, R. D.; Haviv., F.; Hanel, A. M.; Bornemeier, D. A.; Carter, G. W. Fed. Proc., Fed.Am.Soc. Exp. Biol. 1984, 43, 1462a). Inhibitory potencies for representative examples of this invention are listed in Table 14. IC$_{50}$ values (concentration of compound producing 50% enzyme inhibition) were calculated by linear regression analysis of percentage inhibition versus log inhibitor concentration plots.

TABLE 14

In vitro 5-lipoxygenase inhibitory potency of compounds of this invention.

| Example | IC$_{50}$ ($\mu$M) | Example | IC$_{50}$ ($\mu$M) |
|---|---|---|---|
| 1 | 11 | 3 | 6 |
| 6 | 2 | 8 | 5 |
| 10 | 3 | 15 | 6 |
| 16 | 5 | 24 | 3 |
| 26 | 1 | 38 | 0.6 |
| 40 | 0.5 | 46 | 2.5 |
| 51 | 10 | 85 | 3 |
| 68 | 21 | 86 | 7 |
| 70 | 15 | 87 | 7 |
| 73 | 5 | 88 | 19 |
| 74 | 13 | 90 | 26 |
| 75 | 14 | 99 | 8 |
| 76 | 17 | 102 | 17 |
| 78 | 6 | 103 | 5 |
| 79 | 1 | 106 | 1 |
| 80 | 12 | 107 | 3 |
| 81 | 11 | 109 | 1 |
| 82 | 7 | 111 | 1 |
| 83 | 2 | 113 | 71 |

INHIBITION OF LEUKOTRIENE BIOSYNTHESIS

Inhibition of the biosynthesis of leukotrienes in vivo after oral administration of compound was determined using a rat peritoneal anaphylaxis model in a similiar manner as that described by Young and coworkers (Young, P. R.; Dyer, R. D.; Carter, G. W. Fed. Proc., Fed. Am Soc.Exp. Biol. 1985, 44 1185). In this model rats were injected intraperitoneally (ip) with rabbit antibody to bovine serum albumin (BSA) and three hours later injected ip with BSA to induce an antigen-antibody response. Rats were sacrificed 15 minutes after this challenge and the peritoneal fluids were collected and analyzed for leukotriene levels. Test compounds were administered by gavage one hour prior to the antigen challenge. Inhibitory potencies for representative examples of this invention are listed in Table 15. Percent inhibition values were determined by comparing the treatment group to the mean of the control group. From the results of this assay it is demonstrated that compounds of this invention are orally effective in preventing the in vivo biosynthesis of leukotrienes.

TABLE 15

In Vivo inhibition of leukotriene biosynthesis by oral administration

| Example | % inhibition at 200 micro mol/kq/oral dose |
|---|---|
| 68 | 85 |
| 70 | 66 |
| 73 | 46 |
| 74 | 58 |
| 75 | 73 |
| 78 | 80 |
| 81 | 84 |
| 111 | 74 |

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, tosylate, mesylate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl., and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula

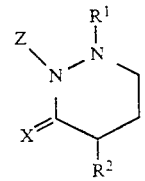

wherein X is oxygen or sulfur;
R$^1$ is selected from the group consisting of
benzofuranyl,
2-benzoxazolyl;
dibenzofuranyl,
dibenzopyrrolyl, optionally substituted with alkyl of from one to four carbon atoms,
fluorenyl,
indanyl,
N-morpholinyl,
tetrahydronaphthyl,
2-, 3- or 4-pyridyl, optionally substituted by alkyl of from one to four carbon atoms and nitro,
pyrimidyl;
quinolinyl;
thianaphthyl,
phenyl; and
phenyl substituted by
alkyl of from one to twelve carbon atoms,
alkoxy of from one to twelve carbon atoms,
alkoxycarbonyl of from two to six carbon atoms,
benzyl,
cyano, halogen,
hydroxymethyl,
methylsulfonyl,
methylthio,
phenoxy,
trifluoromethyl, and

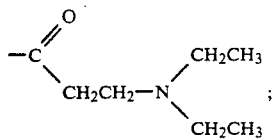

R² is selected from the group consisting of
  hydrogen,
  alkyl of from one to twelve carbon atoms, optionally substituted with
    hydroxy,
    alkoxy of from one to four carbon atoms,
    benzoxy,
    alkylthio of from one to four carbon atoms,
    phenylthio,
    alkanoyl of from two to four carbon atoms, or
    dialkylamino,
  alkylenyl of from two to four carbon atoms,
  alkanoyl of from one to four carbon atoms,
  benzoyl,
  alkoxy of from one to twelve carbon atoms,
  cyano,
  phenyl,
  benzyl, and
  thienyl; and
Z is selected from the group consisting of
  hydrogen,
  a pharmaceutically acceptable cation, and
  a metabolically cleavable group selected from
    acetyl,
    methoxycarbonyl,
    benzoyl,
    —COR,
    —COOR,
    —CH₂COOR,
    —C(O)NRR,
    —CH₂C(O)NRR,
    —CH₂OR, and
    —CH₂SR,
  where R is selected at each occurrence from
    alkyl of from one to twelve carbon atoms,
    phenyl, and phenyl substituted with halogen,
    alkyl of from one to twelve carbon atoms, or
    alkoxy of from one to twelve carbon atoms.

2. A compound of the formula

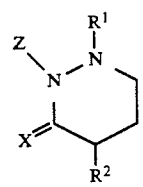

where X is oxygen or sulfur;
  R¹ is selected from the group consisting of
    phenyl; and
    phenyl substituted by
      alkyl of from one to twelve carbon atoms,
      alkoxy of from one to twelve carbon atoms,
      alkoxycarbonyl of from two to six carbon atoms,
      benzyl,
      cyano,
      halogen,
      hydroxymethyl,
      methylsulfonyl,
      methylthio,
      phenoxy,
      trifluoromethyl, and

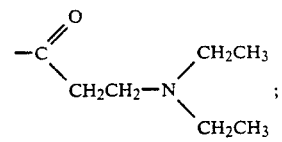

R² is selected from the group consisting of
  hydrogen,
  alkyl of from one to twelve carbon atoms, optionally substituted with
    hydroxy,
    alkoxy of from one to four carbon atoms,
    benzoxy,
    alkylthio of from one to four carbon atoms,
    phenylthio,
    alkanoyl of from two to four carbon atoms, or
    dialkylamino,
  alkylenyl of from two to four carbon atoms,
  alkanoyl of from one to four carbon atoms,
  benzoyl,
  alkoxy of from one to twelve carbon atoms,
  cyano,
  phenyl,
  benzyl, and
  thienyl; and
Z is selected from the group consisting of
  hydrogen,
  a pharmaceutically acceptable cation, and
  a metabolically cleavable group selected from
    acetyl,
    methoxycarbonyl,
    benzoyl,
    —COR,
    —COOR,
    —CH₂COOR,
    —C(O)NRR,
    —CH₂C(O)NRR,
    —CH₂OR, and
    —CH₂SR,
  where R is selected at each occurrence from
    alkyl of from one to twelve carbon atoms,
    phenyl, and phenyl substituted with halogen,
    alkyl of from one to twelve carbon atoms, or
    alkoxy of from one to twelve carbon atoms.

3. A compound of the formula

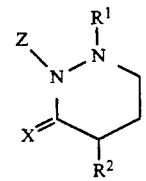

where X is oxygen or sulfur;
  R¹ is selected from the group consisting of
    benzofuranyl, 2-benzoxazolyl;
dibenzofuranyl,
dibenzopyrrolyl, optionally substituted with alkyl of from one to four carbon atoms,
fluorenyl,
indanyl,
N-morpholinyl,
tetrahydronaphthyl,
2-, 3- or 4-pyridyl optionally substituted by alkyl of from one to four carbon atoms and nitro,
pyrimidyl;
quinolinyl;
thianaphthyl;

$R^2$ is selected from the group consisting of
hydrogen,
alkyl of from one to twelve carbon atoms, optionally substituted with
hydroxy,
alkoxy of from one to four carbon atoms,
benzoxy,
alkylthio of from one to four carbon atoms,
phenylthio,
alkanoyl of from two to four carbon atoms, or
dialkylamino,
alkylenyl of from two to four carbon atoms,
alkanoyl of from one to four carbon atoms,
benzoyl,
alkoxy of from one to twelve carbon atoms,
cyano,
phenyl,
benzyl, and
thienyl; and Z is selected from the group consisting of
hydrogen,
a pharmaceutically acceptable cation, and
a metabolically cleavable group selected from
acetyl,
methoxycarbonyl,
benzoyl,
—COR,
—COOR,
—CH$_2$COOR,
—C(O)NRR,
—CH$_2$C(O)NRR,
—CH$_2$OR, and
—CH$_2$SR,
where R is selected at each occurrence from alkyl of from one to twelve carbon atoms, phenyl, and phenyl substituted with halogen, alkyl of from one to twelve carbon atoms, or alkoxy of from one to twelve carbon atoms.

4. A pharmaceutical composition useful for inhibiting lipoxygenase activity in humans and lower mammals comprising a lipoxygenase inhibiting effective amount of a compound as defined by claim 1 in combination with a pharmaceutically acceptable carrier.

5. A method of inhibiting lipoxygenase activity in a human or lower mammal in need of such treatment comprising administering an effective amount of a compound as defined by claim 1.

* * * * *